US012797080B2

(12) United States Patent
Chana

(10) Patent No.: US 12,797,080 B2
(45) Date of Patent: Nov. 17, 2026

(54) APPARATUS FOR USE IN SURGERY

(71) Applicant: Gursharan Singh Chana, Birmingham (GB)

(72) Inventor: Gursharan Singh Chana, Birmingham (GB)

( * ) Notice: Subject to any disclaimer, the term of this patent is extended or adjusted under 35 U.S.C. 154(b) by 101 days.

(21) Appl. No.: 18/437,966

(22) Filed: Feb. 9, 2024

(65) Prior Publication Data

US 2024/0285326 A1 Aug. 29, 2024

Related U.S. Application Data

(63) Continuation-in-part of application No. PCT/GB2022/052076, filed on Aug. 9, 2022.

(60) Provisional application No. 63/231,867, filed on Aug. 11, 2021.

(51) Int. Cl.

| | |
|---|---|
| ***A61B 17/14*** | (2006.01) |
| ***A61B 17/88*** | (2006.01) |
| ***A61B 17/92*** | (2006.01) |
| ***A61F 2/46*** | (2006.01) |

(52) U.S. Cl.

CPC ........ *A61B 17/149* (2016.11); *A61B 17/8861* (2013.01); *A61B 17/92* (2013.01); *A61F 2/4607* (2013.01); *A61F 2002/4619* (2013.01)

(58) Field of Classification Search

CPC ... A61B 17/149; A61B 17/92; A61B 17/1604; A61B 17/8861; A61B 17/1659; A61B 17/1668; A61F 2/4607; A61F 2002/4619; A61F 15/02

USPC .................................................... 606/105.05

See application file for complete search history.

(56) References Cited

U.S. PATENT DOCUMENTS

| | | | | |
|---|---|---|---|---|
| 4,943,255 | A * | 7/1990 | Klundt | A63H 33/28 446/15 |
| 5,725,530 | A | 3/1998 | Popken | |
| 2013/0211406 | A1 * | 8/2013 | Chavarria | A61F 2/4612 606/79 |
| 2014/0053414 | A1 * | 2/2014 | Ling | B26B 27/002 30/278 |

FOREIGN PATENT DOCUMENTS

| | | | | |
|---|---|---|---|---|
| EP | 0056656 A1 | | 7/1982 | |
| WO | WO-2005042213 A1 | * | 5/2005 | A61B 17/149 |
| WO | WO-2009052776 A1 | * | 4/2009 | A61F 2/4607 |
| WO | 2011045568 A2 | | 4/2011 | |
| WO | WO-2016126043 A1 | * | 8/2016 | A61B 17/14 |
| WO | 2017032993 A1 | | 3/2017 | |
| WO | 2019224561 A1 | | 11/2019 | |

OTHER PUBLICATIONS

Machine translation of WO 2009/052776 (Year: 2025).*
International Search Report and Written Opinion corresponding to PCT/GB2022/052076; Mailed Oct. 31, 2022, (12 pages).

* cited by examiner

*Primary Examiner* — Amy R Sipp
(74) *Attorney, Agent, or Firm* — Myers Bigel, P.A.

(57) ABSTRACT

The invention provides a wire delivery device, suitable for use in removing bony ingrowth from an implant such as a femoral implant. The wire delivery device comprises first and second elongate bodies and holds and provides cutting wire in the form of medial and lateral cutting wire arcs. The cutting wire can be used to cut by pushing the first and second elongate bodies in an alternating motion in the desired direction of cutting.

20 Claims, 25 Drawing Sheets

301a
300
302

300
305

300
100°
305

302
309
308

753
750
752
754
751

APPARATUS FOR USE IN SURGERY

CROSS-REFERENCE TO RELATED APPLICATIONS

This application is a Continuation-in-Part of International Application No. PCT/GB2022/052076, filed Aug. 9, 2022, which claims the benefit of U.S. Provisional Patent Application No. 63/231,867, filed Aug. 11, 2021, the disclosures of which are incorporated by reference herein in their entireties.

This invention relates to methods of removing implants embedded in surrounding tissue material and to associated apparatus for use in removing implants. More particularly, this invention relates to methods and apparatus for removing implants, such as femoral implants, from surrounding tissue material, e.g., in a human or animal body.

DESCRIPTION OF THE PRIOR ART

It is often necessary to remove implants that have previously been inserted, for example, where the implant has become loose, or the tissue surrounding the implant is infected. The failure rate of femoral implants, necessitating removal and insertion of a new implant, is believed to be about 10%.

Implants may generally be cemented or uncemented into position. For uncemented implants bony ingrowth is encouraged, which serves to secure the implant. Fibrous tissue may grow and encapsulate the implant.

A disadvantage of many known approaches is that to remove the implant any cement and bony ingrowth around the implant needs to be removed. In practice this results in large amounts of surrounding tissue (e.g., bone) being taken out, with a significantly larger cavity being left behind. The surgery is therefore relatively invasive and more expensive. In addition, the recovery from the surgery takes longer, and the patient cannot load bear through the new implant for some time after the surgery. For uncemented implant removal, in the majority of cases an extended trochanteric osteotomy has to be carried out to remove the implant. This has to be wired up to secure the revision implant.

Common approaches to removing implants involve the use of standard osteotome devices. Approaches are also described in WO2011/045568, WO2017/032993 and WO2019/224561, each of which use a drill guide or targeting device to carry out a method of removing an implant, e.g., a femoral implant, that has previously been inserted in a human or animal body. The content of each of these documents is incorporated in its entirety by reference.

It can still be difficult to remove collared implants, however. In the situation where the implant is collared, the collar can restrict the access that can be achieved by devices. Specifically, the presence of a collar on the medial side at the shoulder, which usually extends from the medial border of the shoulder to halfway laterally, will prevent the clearance of the medial surface of the implant using the medial-lateral clearance device of WO2019/224561.

In addition, for both collared and collarless implants, there is still a need to make the removal of the implant easier and more accurate. It is desirable to have as much control as possible, to reduce the chance of damage to the femur.

SUMMARY OF THE INVENTION

The present invention provides a new piece of apparatus that can be used in the known approaches, such as those described in WO2011/045568, WO2017/032993 and WO2019/224561, to improve the final step of releasing the implant before removal.

In this regard, the present invention provides a wire delivery device that can be used to clear at least the medial aspect of an implant. It may optionally and usefully also be utilised to clear the lateral aspect of the implant.

The wire delivery device of the invention can, in particular, be useful for clearing at least the medial aspect of a collared implant, but it is not limited to this use. In one embodiment the device is used for a collarless implant.

The wire delivery device can be used in a method of removing an implant, especially a femoral implant, from the surrounding tissue, the method comprising:

- creating access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant, wherein the anterior access tunnel is spaced from and substantially parallel to the anterior surface of the implant and the posterior access tunnel is spaced from and substantially parallel to the posterior surface of the implant;
- using the anterior access tunnel to access and remove bony ingrowth located between the implant and the femur in the anterior aspect, and using the posterior access tunnel to access and remove bony ingrowth located between the implant and the femur in the posterior aspect;
- clearing the lateral aspect of the implant by removing bony ingrowth located at the antro-lateral edge of the implant and at the postro-lateral edge of the implant; and
- clearing the medial aspect of the implant by removing bony ingrowth located at the antro-medial edge of the implant and at the postro-medial edge of the implant.

The wire delivery device of the invention is suitably used in at least the step of clearing the medial aspect of the implant by removing bony ingrowth located at the antro-medial edge of the implant and at the postro-medial edge of the implant.

In one embodiment, the method of removing an implant comprises:

1) placing a targeting device, which may optionally but preferably be a targeting device according to WO2019/224561, on the implant and locking it on the shoulder of the implant;
2) checking the alignment of the targeting device using a medial targeting device, which may optionally but preferably be a medial targeting device according to WO2019/224561;
3) checking the alignment of the targeting device using an external targeting device, which may optionally but preferably be an external targeting device according to WO2019/224561;
4) creating at least one access tunnel anteriorly and creating at least one access tunnel posteriorly, wherein these tunnels are created using a tool such as a drill or chisel, which may optionally but preferably be a chevron chisel according to WO2019/224561;
5) removing the targeting device from the implant;
6) optionally increasing the size of the access tunnels using a tool, which may optionally but preferably be a chevron chisel according to WO2019/224561 and/or a chevron osteotome device according to WO2019/224561;

7) using a curette, which may optionally but preferably be a curette according to WO2019/224561, to remove bony ingrowth located between the implant and the femur in the anterior aspect, and to remove bony ingrowth located between the implant and the femur in the posterior aspect;

8) using a medial-lateral clearance device, which may optionally but preferably be a medial-lateral clearance device according to WO2019/224561, to clear the lateral aspect of the implant by removing bony ingrowth located at the antro-lateral edge of the implant and at the postro-lateral edge of the implant; and 9) using a wire delivery device according to the present invention to clear at least the medial aspect of the implant by removing bony ingrowth located at the antro-medial edge of the implant and at the postro-medial edge of the implant.

Step 6) is optional. The access tunnels as formed in step 4) may already be wide enough to move onto step 7) after step 5), especially if the access tunnels are made using a chevron chisel.

Optionally, and in many cases preferably, step 9) may be used to clear the lateral aspect of the implant as well as the medial aspect of the implant. Thus step 9) may additionally use a wire delivery device according to the present invention to clear the lateral aspect of the implant by removing bony ingrowth located at the antro-lateral edge of the implant and at the postro-lateral edge of the implant.

Thus, in some embodiments, step 8) may be omitted and step 9) may be used to clear the lateral aspect of the implant as well as the medial aspect of the implant.

In one embodiment, the brace targeting device as shown in FIGS. 10*c*-10*e* and as described herein is used instead of the external targeting device according to WO2019/224561. This can be used to create access tunnels anteriorly and posteriorly, using a chevron chisel as described herein.

In one embodiment, the method of removing an implant comprises:

a) placing a targeting device, which may optionally but preferably be a targeting device according to WO2019/224561, on the implant and locking it on the shoulder of the implant;

b) checking the alignment of the targeting device using a medial targeting device, which may optionally but preferably be a medial targeting device according to WO2019/224561;

c) checking the alignment of the targeting device an external targeting device, which may optionally but preferably be an external targeting device according to WO2019/224561;

d) using a chevron chisel, which may optionally but preferably be a chevron chisel according to WO2019/224561, to create an access tunnel anteriorly, and using a chevron chisel, which may optionally but preferably be a chevron chisel according to WO2019/224561, to create an access tunnel posteriorly, wherein these access tunnels may optionally but preferably have a depth of about 1 to 2 mm (e.g. about 1 mm) and may optionally but preferably have a width of about 4 to 12 mm (e.g. about 4 to 10 mm);

e) removing the targeting device from the implant;

f) if desired, using a chisel, which may optionally but preferably be a chevron chisel according to WO2019/224561, to increase the size of the access tunnels;

g) using a curette, which may optionally but preferably be a curette according to WO2019/224561, to remove bony ingrowth located between the implant and the femur in the anterior aspect, and to remove bony ingrowth located between the implant and the femur in the posterior aspect;

h) using a medial-lateral clearance device, which may optionally but preferably be a medial-lateral clearance device according to WO2019/224561, to clear the lateral aspect of the implant by removing bony ingrowth located at the antro-lateral edge of the implant and at the postro-lateral edge of the implant;

i) using a wire delivery device according to the present invention to clear the medial aspect of the implant by removing bony ingrowth located at the antro-medial edge of the implant and at the postro-medial edge of the implant.

Alternatively, step h) may be omitted and in step i) the wire delivery device may be used to clear the lateral aspect of the implant as well as the medial aspect of the implant.

In one embodiment, step 4) or step d) creates initial access tunnels, anteriorly and posteriorly, and step 6) or step f) creates a sub access tunnel within each initial access tunnel. The sub access tunnel may be deeper than the initial access tunnel but less wide than the initial access tunnel. Each sub access tunnel may be sized to facilitate use of the wire delivery device in step 9) or step i) and therefore each may suitably be sized to receive one of the elongate bodies of the wire delivery device.

It may be that the initial access tunnels each have a maximum depth of about 1 to 2 mm, such as about 1 mm and they may optionally but preferably have a maximum width of about 4 to 12 mm, such as about 10 mm. It may be that the sub access tunnels each have a maximum depth of about 1.5 to 2 mm, such as about 1.5 mm and they may optionally but preferably have a maximum width of about 4 to 7 mm, such as about 5 mm.

In one embodiment, the brace targeting device as shown in FIGS. 10*c*-10*e* and as described herein is used instead of the external targeting device according to WO2019/224561. This can be used to create access tunnels anteriorly and posteriorly, using a chevron chisel as described herein.

In one embodiment, the method of removing an implant comprises:

a) placing a targeting device, which may optionally but preferably be a targeting device according to WO2019/224561, on the implant and locking it on the shoulder of the implant;

b) checking the alignment of the targeting device using a medial targeting device, which may optionally but preferably be a medial targeting device according to WO2019/224561;

c) checking the alignment of the targeting device an external targeting device, which may optionally but preferably be an external targeting device according to WO2019/224561;

d) using a chevron chisel, which may optionally but preferably be a chevron chisel according to WO2019/224561, to create an access tunnel anteriorly and using a chevron chisel, which may optionally but preferably be a chevron chisel according to WO2019/224561, to create an access tunnel posteriorly, wherein these access tunnels may optionally but preferably have a depth of about 1 to 2 mm (e.g. about 1 mm) and may optionally but preferably have a width of about 4 to 12 mm (e.g. about 10 mm);

e) removing the targeting device from the implant;

f) using a chisel, which may optionally but preferably be a chevron chisel according to WO2019/224561, and which may be about 1.5 to 2 mm thick and about 4 to 7 mm wide, to increase the size of the access tunnels, e.g. to create sub access tunnels which are deeper than but less wide than the respective initial access tunnel formed in step d);

g) using a curette, which may optionally but preferably be a curette according to WO2019/224561, to remove bony ingrowth located between the implant and the femur in the anterior aspect, and to remove bony ingrowth located between the implant and the femur in the posterior aspect;

h) using a medial-lateral clearance device, which may optionally but preferably be a medial-lateral clearance device according to WO2019/224561, to clear the lateral aspect of the implant by removing bony ingrowth located at the antro-lateral edge of the implant and at the postro-lateral edge of the implant;

i) using a wire delivery device according to the present invention to clear the medial aspect of the implant by removing bony ingrowth located at the antro-medial edge of the implant and at the postro-medial edge of the implant.

Alternatively, step h) may be omitted and in step i) the wire delivery device may be used to clear the lateral aspect of the implant as well as the medial aspect of the implant.

In one embodiment, the brace targeting device as shown in FIGS. 10*c*-10*e* and as described herein is used instead of the external targeting device according to WO2019/224561. This can be used to create access tunnels anteriorly and posteriorly, using a chevron chisel as described herein.

In one embodiment of any of the above-disclosed methods of removing an implant, only cutting devices with a thickness of 2 mm or less (or 1.5 mm or less) are used. This can be beneficial in terms of minimising loss of tissue around the implant.

The present invention provides the novel wire delivery device individually. The present invention also provides a kit comprising the novel wire delivery device together with any one or more of the above-mentioned apparatus/devices, for example with any two or more, or any three or more, or any four or more such devices. In one embodiment there is a kit comprising all of the above-mentioned apparatus/devices.

In one embodiment two or more, such as three or more, of the devices have the same or similar width at their proximal end. It may be that all of the devices in the kit have the same or similar width at their proximal end. This provides the option that a universal handle could be used which would fit onto multiple devices. In one embodiment, the width at the proximal end for each device is relatively narrow, e.g. from 5 to 10 mm. This has the benefit of being able to slide the same brace onto for multiple devices in the kit; therefore a re-useable brace could be used.

In one embodiment, one or more or two or more, such as three or more, of the devices may be provided as single-use pre-packed sterilised devices. The skilled person will appreciate that useful forms of sterilisation include gamma (irradiation) sterilisation or ethylene oxide (EtO) sterilisation. This is in particular foreseen for the devices within the kit that are cutting devices. It may usefully be that all cutting devices are provided as single-use pre-packed sterilised devices.

Further parts of the kit may optionally be provided as single-use pre-packed sterilised products, e.g. a brace sleeve may be. provided as a single-use pre-packed sterilised product.

In particular, in one embodiment the novel wire delivery device is provided in combination with a chevron chisel according to WO2019/224561 and/or with a curette according to WO2019/224561 and/or with a medial-lateral clearance device according to WO2019/224561.

The novel wire delivery device of the invention comprises:

a first elongate body that extends from a first elongate edge to a second elongate edge and that has an inner face and an outer face, the elongate body having a proximal end that can be provided with a handle and a distal end that may optionally be blunt, wherein there is a wire receiving portion provided in a spaced relationship with the distal end, wherein cutting wire can be located and secured in the wire receiving portion;

a second elongate body that extends from a first elongate edge to a second elongate edge and that has an inner face and an outer face, the elongate body having a proximal end that can be provided with a handle and a distal end that may optionally be blunt, wherein there is a wire receiving portion provided in a spaced relationship with the distal end, wherein cutting wire can be located and secured in the wire receiving portion;

such that, in use, the elongate bodies can be positioned in a spaced apart and opposite but aligned configuration, and wherein a first length of cutting wire can be secured so as to extend from a location in the wire receiving portion of the first elongate body to a location in the wire receiving portion of the second elongate body, to provide a medial cutting wire arc extending between the first elongate body and the second elongate body, and wherein a second length of cutting wire can be secured so as to extend from a location in the wire receiving portion of the first elongate body to a location in the wire receiving portion of the second elongate body, to provide a lateral cutting wire arc extending between the first elongate body and the second elongate body, whereby the medial and lateral cutting wire arcs can then be used to cut, by pushing the first and second elongate bodies in an alternating motion in the desired direction of cutting.

The first length of cutting wire and second length of cutting wire can be a single piece of wire, such that the medial and lateral cutting wire arcs together form a closed wire loop. Alternatively, the first length of cutting wire and second length of cutting wire can be separate pieces of wire. The wire is suitably annealed wire, e.g., medical grade titanium or titanium alloy or stainless steel.

It may be that the wire delivery device is provided in a form where the first and second lengths of cutting wire are provided as part of the device, e.g., as a kit. In one preferred embodiment the first and second lengths of cutting wire are provided as part of the device and are secured in place, such that the medial and lateral cutting wire arcs are provided, each extending between the first elongate body and the second elongate body.

When using the wire delivery device of the invention, the medial and lateral cutting wire arcs can be used to cut by:

locating the first and second elongate bodies in the anterior and posterior access tunnels, locating the medial cutting wire arc on the medial side of the implant and locating the lateral cutting wire arc on the lateral side of the implant, pushing the first and second elongate bodies in an alternating motion in the desired direction of cutting, into the space that has already been created by the previous steps, to cause the medial cutting wire arc to cut through the medial part of the femur, beneath the medial shoulder and to cause the lateral cutting wire arc to cut through the lateral part of the femur, beneath the lateral shoulder.

If the implant is collared, it will be appreciated that the medial loop must be located on the medial side of the implant in a position inferior to the collar, e.g., it may be hooked over the collar.

The wire arcs will not be directly exposed to the bone because they are secured in the wire receiving portions and these are spaced from the distal end. The distal end is therefore usefully blunt, to protect the bone from the wire. However, it is also envisaged that the distal ends of the first and second elongate bodies may be chisel like, e.g. with a 45 degree chisel angle. This can be advantageous in terms of facilitating an easy transition into the bone-implant interface. Also, it will assist with keeping the wire delivery device pushed against the implant.

The first and second elongate bodies are pushed in an alternating motion to cause the wire arcs to cut, directing the force distally. As the medial cutting wire arc traverses distally, it will clear the bone-implant interface medially. As the lateral cutting wire arc traverses distally, it will clear the bone-implant interface laterally. The distal movement of the first and second elongate bodies may be carried out manually, e.g., using a hammer, or a reciprocating mechanism (e.g. reciprocating saw) could be used to drive each of the first and second elongate bodies.

In a preferred first embodiment, the novel wire delivery device of the invention comprises:

a first elongate body that extends from a first elongate edge to a second elongate edge and that has an inner face and an outer face, the elongate body having a proximal end that can be provided with a handle and a distal end that may optionally be blunt, wherein there is a first wire receiving slot provided in a spaced relationship with the distal end and located towards the first elongate edge, wherein the first wire receiving slot runs from an open entrance to a closed end, and wherein there is a second wire receiving slot provided in a spaced relationship with the distal end and located towards the second elongate edge, wherein the second wire receiving slot runs from an open entrance to a closed end;

a second elongate body that extends from a first elongate edge to a second elongate edge and that has an inner face and an outer face, the elongate body having a proximal end that can be provided with a handle and a distal end that may optionally be blunt, wherein there is a first wire receiving slot provided in a spaced relationship with the distal end and located towards the first elongate edge, wherein the first wire receiving slot runs from an open entrance to a closed end, and wherein there is a second wire receiving slot provided in a spaced relationship with the distal end and located towards the second elongate edge, wherein the second wire receiving slot runs from an open entrance to a closed end;

a first length of cutting wire extending from a first end to a second end, wherein the first end is secured in the first wire receiving slot of the first elongate body and the second end is secured in the first wire receiving slot of the second elongate body;

a second length of cutting wire extending from a first end to a second end, wherein the first end is secured in the second wire receiving slot of the first elongate body and the second end is secured in the second wire receiving slot of the second elongate body;

such that, in use, the elongate bodies can be positioned in a spaced apart and opposite but aligned configuration, so that the first length of cutting wire provides a medial cutting wire arc, extending from the open entrance of the first wire receiving slot of the first elongate body to the open entrance of the first wire receiving slot of the second elongate body, and so that the second length of cutting wire provides a lateral cutting wire arc, extending from the open entrance of the second wire receiving slot of the first elongate body to the open entrance of the second wire receiving slot of the second elongate body, whereby the medial and lateral cutting wire arcs can then be used to cut, by pushing the first and second elongate bodies in an alternating motion in the desired direction of cutting.

As noted above, in one preferred embodiment sub access tunnels have been formed for receiving the first and second elongate bodies, and therefore in one preferred embodiment the first and second elongate bodies are located in and pushed along these sub access tunnels.

The cutting wire arcs will not be directly exposed to the bone because they are secured in the wire receiving slots and these are spaced from the distal end. The distal end is therefore usefully blunt, to protect the bone from the wire. However, it is also envisaged that the distal ends of the first and second elongate bodies may be chisel like, e.g. with a 45 degree chisel angle. This can be advantageous in terms of facilitating an easy transition into the bone-implant interface. Also, it will assist with keeping the wire delivery device pushed against the implant.

The first and second elongate bodies are pushed in an alternating motion to cause the cutting wire arcs to cut, directing the force distally. As the medial cutting wire arc traverses distally, it will clear the bone-implant interface medially. As the lateral cutting wire arc traverses distally, it will clear the bone-implant interface laterally. The distal movement of the first and second elongate bodies may be carried out manually, e.g., using a hammer, or a reciprocating mechanism (e.g. reciprocating saw) could be used to drive each of the first and second elongate bodies.

In an alternative second embodiment, the novel wire delivery device of the invention comprises:

a first elongate body that extends from a first elongate edge to a second elongate edge and that has an inner face and an outer face, the elongate body having a proximal end that can be provided with a handle and a distal end that may optionally be blunt, where there is a first wire guidance channel provided in a spaced relationship with the distal end and located within the first elongate body, wherein the first wire guidance channel runs from an entrance at the first elongate edge to an exit at the second elongate edge, and wherein either the inner face or the outer face includes a first mouth portion to access the first wire guidance channel and a first engagement protrusion adjacent to the first mouth portion for engaging with a first part of a wire loop and securing this part of the wire loop within the first wire guidance channel;

a second elongate body that extends from a first elongate edge to a second elongate edge and that has an inner face and an outer face, the elongate body having a proximal end that can be provided with a handle and a distal end that may optionally be blunt, where there is a second wire guidance channel provided in a spaced relationship with the distal end and located within the second elongate body, wherein the second wire guidance channel runs from an entrance at the first elongate edge to an exit at the second elongate edge, and wherein either the inner face or the outer face includes a second mouth portion to access the second wire guidance channel and a second engagement protrusion adjacent to the second mouth portion for engaging with a second part of a wire loop and securing this part of a wire loop within the second wire guidance channel;

such that, in use, a wire loop can be provided and a first part of the wire loop can be fed into the first wire guidance channel via the first mouth portion and secured therein by engagement with the first engagement protrusion and a second part of the wire loop can be fed into the second wire guidance channel via the second mouth portion and secured therein by engagement with the second engagement protrusion, and the elongate bodies can be positioned in a spaced apart and opposite but aligned configuration, so that the wire loop provides a medial cutting wire arc from the exit of the first wire guidance channel to the entrance of the second wire guidance channel and provides a lateral cutting wire arc from the exit of the second wire guidance channel to the entrance of the first wire guidance channel, whereby the cutting wire arcs can then be used to cut by pushing the first and second elongate bodies in an alternating motion in the desired direction of cutting.

When using the second wire delivery device of the invention, once the wire loop is located and secured in the first and second wire guidance channels, the cutting wire arcs can be used to cut by:

- locating the wire loop around the implant, with the first and second elongate bodies in the anterior and posterior access tunnels, and
- pushing the first and second elongate bodies in an alternating motion in the desired direction of cutting, into the space that has already been created by the previous steps, to cause the medial cutting wire arc to cut through the medial part of the femur, beneath the medial shoulder, and optionally to cause the lateral cutting wire arc to cut through the lateral part of the femur, beneath the lateral shoulder.

As noted above, in one preferred embodiment sub access tunnels have been formed for receiving the first and second elongate bodies, and therefore in one preferred embodiment the first and second elongate bodies are located in and pushed along these sub access tunnels.

The wire loop will not be directly exposed to the bone because it is secured in the wire guidance channels and these are spaced from the distal end. The distal end is therefore usefully blunt, to protect the bone from the wire. However, it is also envisaged that the distal ends of the first and second elongate bodies may be chisel like, e.g. with a 45 degree chisel angle. This can be advantageous in terms of facilitating an easy transition into the bone-implant interface. Also, it will assist with keeping the wire delivery device pushed against the implant.

The first and second elongate bodies are pushed in an alternating motion to cause the wire arcs to cut, directing the force distally. As the wire traverses distally, it will clear the bone-implant interface medially (and optionally laterally as well). The distal movement of the first and second elongate bodies may be carried out manually, e.g., using a hammer, or a reciprocating mechanism (e.g. reciprocating saw) could be used to drive each of the first and second elongate bodies.

In one embodiment, the brace targeting device as shown in FIGS. 10*c*-10*e* and as described herein can be used to provide and position the wire targeting device of the invention, as described in the detailed description below.

DETAILED DESCRIPTION OF THE INVENTION

The present invention permits an implant, especially a femoral implant, to be more readily removed from the surrounding tissue and with significantly less loss of tissue around the implant. The procedure is less invasive and generally will involve loss of tissue around the implant of the order of about 0.6 mm-1 mm, or even only about 0.6 mm, or even less, in each direction.

As the skilled reader will appreciate, a femoral implant has a tapered body. This extends from a broader proximal end, which provides a shoulder portion, to a narrower distal end. A neck extends from the proximal end, and a head extends from the neck.

The procedure generally involves firstly creating two access tunnels in the surrounding tissue, one at the anterior of the implant and one at the posterior of the implant, with each access tunnel extending from an access point at the proximal surface of the surrounding tissue, which can be accessed by a person carrying out the procedure, to a point in the surrounding tissue that is located beyond the distal end of the implant (e.g. at a distance of about 0.3 to 1.2 cm beyond the distal end, and preferably 0.5 to 1 cm beyond the distal end). The anterior access tunnel is spaced from and substantially parallel to the anterior surface of the implant and the posterior access tunnel is spaced from and substantially parallel to the posterior surface of the implant.

The anterior access tunnel is preferably spaced from the anterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm and especially such as from 0.5 to 1 mm (preferably 0.5 mm).

The posterior access tunnel is preferably spaced from the posterior surface of the implant by a distance of from 0.1 to 10 mm, such as from 0.1 to 8 mm or from 0.1 to 6 mm; in one preferred embodiment the distance is less than 5 mm, preferably less than 4 mm, or less than 3 mm, or less than 2 mm, such as from 0.1 to 2 mm. Most preferably the distance is less than 1 mm, such as from 0.3 mm to 1 mm and especially such as from 0.5 to 1 mm (preferably 0.5 mm).

The access tunnels may be any shape in cross section, provided they are elongate. It will be appreciated that their dimension that extends substantially perpendicular to the anterior surface or the posterior surface should be relatively small, so as to minimise unnecessary removal of surrounding tissue, e.g. from 0.5 mm to 5 mm. However, their dimension that extends substantially parallel to the anterior surface or the posterior surface can be larger, if desired, because the method is seeking to create a space that extends over the width of the anterior surface and the posterior surface of the implant. Therefore this dimension can be larger than 5 mm without leading to unnecessary removal of surrounding tissue.

The access tunnels may be elongate bores with round cross sections, e.g. substantially circular cross sections. The diameter of the access tunnels may suitably be from 0.5 mm to 5 mm, preferably from 1 mm to 4 mm, e.g. from 2 mm to 4 mm or from 2.5 mm to 3.5 mm. However, other cross sectional shapes can be envisaged for the access tunnels, e.g. rectangular or square. The dimension that extends substantially perpendicular to the anterior surface or the posterior surface may suitably be from 0.5 mm to 5 mm, preferably from 1 mm to 4 mm, e.g. from 2 mm to 4 mm or from 2.5 mm to 3.5 mm. Thus the minimum diameter of the access tunnels (i.e. the smallest distance, when considered as a straight line, from one point on the perimeter to another point on the perimeter via the centrepoint) should fall within this range.

The skilled reader will appreciate that in order to make the procedure as minimally invasive as possible, the tunnel as formed should have a dimension that extends substantially perpendicular to the anterior surface or the posterior surface that is as small as possible. However, there is also a desire to remove as much material as possible in a direction substantially parallel to the anterior surface or the posterior surface, to make subsequent steps easier. Therefore the use of two or more tunnels parallel to one another on the anterior surface and/or the posterior surface can be beneficial, because these can each have smaller diameters, and therefore minimise the intrusion into surrounding tissue, but overall these combine to remove more material in a direction substantially parallel to the anterior surface or the posterior surface.

For essentially the same reasons, the use of an access tunnel that has an elongate rather than a circular cross section can be beneficial. In this regard, the cross section should be such that the smallest dimension is in the direction that extends substantially perpendicular to the anterior surface or the posterior surface, whilst the largest direction is in the direction that extends substantially parallel to the anterior surface or the posterior surface. The access tunnel can, for example, have a rectangular shaped cross section.

The present invention also provides a method in which at least the wire delivery device of the invention is used.

First Stage

The first stage of the procedure is suitably effected using a targeting device, which ensures the access tunnels are created at the required locations on the anterior and posterior of the implant. It will be appreciated that the angle of the tunnels is important, because it is desired that the tunnels run all the way along the implant and converge at a location beyond the distal end of the implant.

The access tunnels may be created using conventional tools, such as a drill and drill bits, or a chisel, or a reciprocating saw, or a K-wire. Of course, the tool used could be bespoke instead. The key feature is that the tool is elongate and has at least one edge that is sufficiently sharp that when the tool is operated it can be used to create access tunnels on the anterior and posterior of the implant. Preferably, a chevron chisel according to WO2019/224561 is used.

The targeting device may, in one embodiment, be a drill guide of the type described in WO2011/045568. Such a drill guide is suitably secured on a projection of a femoral implant.

The targeting device may, in another embodiment, be a targeting kit of the type described in WO2017/032993. Such a targeting kit is suitably secured on the head or neck of a femoral implant. If such as targeting kit is used, the first and second guide members may have bores that have any shape cross section, but in particular may have a circular cross section, a square cross section or a rectangular cross section.

However, in a preferred embodiment, the targeting device is a targeting kit of the type described in WO2019/224561, which is suitable for being secured on the shoulder of a femoral implant. As the skilled person will appreciate, it is standard for the shoulder of a femoral implant to have a recess portion, which may optionally have female screw threads provided inside. This recess is provided in implants as standard, so that the distal end of an impactor can engage (e.g. by threaded engagement) into the recess to push and impact the femoral implant into the pre-prepared proximal part of the patient's femur, to the correct depth. The targeting device of WO2019/224561 makes use of this recess portion to engage with the femoral implant.

The targeting device of WO2019/224561, which may be used in the present invention, comprises:

an anterior guide member, which comprises a first elongate body provided with a first angled channel therein, running from an entrance at the proximal end of the guide member to an exit at the distal end of the guide member, and where the first elongate body has a first contact element at its distal end for contacting the anterior surface of the shoulder of the femoral implant and for distancing the exit from the anterior surface of the shoulder of the implant, a posterior guide member, which comprises a second elongate body provided with a second angled channel therein, running from an entrance at the proximal end of the guide member to an exit at the distal end of the guide member, and where the second elongate body has a second contact element at its distal end for contacting the posterior surface of the shoulder of the implant and for distancing the exit from the posterior surface of the shoulder of the implant, an engagement member for locating and engaging the targeting device on the shoulder of the implant, which comprises a third elongate body with an engagement protrusion at its distal end, whereby the engagement protrusion can be received in a recess portion on the shoulder of the implant, and whereby the third elongate body can be located between and aligned with the first elongate body and the second elongate body, such that the elongate axes of the first, second and third elongate bodies are substantially aligned, and with the first and second angled channels converging in the direction of the distal end, a first pair of parallel connector rails, wherein each connector rail can slideably connect the anterior guide member and the posterior guide member via the engagement member, with the connector rails being received in connection bores in the anterior guide member and the posterior guide member, an adjustment system which can adjust the distance between the first elongate body and the third elongate body, so as to move the anterior guide member between a release position and a holding position, and which can adjust the distance between the second elongate body and the third elongate body, so to move the posterior guide member between a release position and a holding position;

wherein when the anterior guide member and the posterior guide member are connected by the first pair of connector rails, via the engagement member, the elongate axes of the elongate bodies are substantially aligned and the angled channels converge in the direction of the distal end, with the convergence angle of the angled channels being in the range of from 2 to 7 degrees or 2 to 6 degrees, such as from 2 to 5 degrees, e.g. 4 or 6 degrees, such that the engagement protrusion can be located in a recess portion on the shoulder of the implant, with the anterior guide member and the posterior guide member in their release positions, and then the adjustment system can be used to move the anterior guide member towards its holding position until the first contact element contacts the shoulder of the implant, with the exit of the first angled channel lying spaced from the anterior surface of the implant, and to move the posterior guide member towards its holding position until the second contact element contacts the shoulder of the implant, with the exit of the second angled channel lying spaced from the posterior surface of the implant.

The convergence between the anterior angled channel and the posterior angled channel may be in the range of 2 to 7 degrees, e.g. from 2 to 6 degrees, preferably 4 or 6 degrees. This is the actual angle of convergence between the anterior angled channel and the posterior angled channel when the targeting device is secured onto the implant.

Preferably the arrangement of the angled channels is symmetrical. In one embodiment, each has a fixed angle, with reference to the elongate axis of the elongate body in which the channel is provided, which is in the range of from 1 to 4 degrees, e.g. from 2 to 4 degrees, such as 2 or 3 degrees.

The first contact element at the distal end of the anterior guide member may be a lip or a leg that extends from the distal end of the elongate body. Likewise, the second contact element at the distal end of the posterior guide member may be a lip or a leg that extends from the distal end of the elongate body.

The engagement member comprises an elongate body with an engagement protrusion at its distal end. This engagement protrusion is sized and shaped to be received in a recess portion on the shoulder of the implant. The skilled person will appreciate that a femoral implant will, as standard, include a recess portion on the shoulder which receives an impactor when the implant is being implanted. This recess is located on the shoulder at the proximal end of the central axis. Therefore the engagement protrusion ensures central alignment for the targeting device on the femoral implant.

Each connector rail slideably connects the anterior guide member and the posterior guide member via the engagement member. Each connector rail is received in a connection bore in the anterior guide member and a connection bore in the posterior guide member. Each connector rail may optionally be provided with a spring or other biasing means that serves to bias the anterior guide member and the posterior guide member into their release positions. The biasing force of the spring or other biasing means can be overcome by use of the adjustment system to move the anterior guide member and the posterior guide member into their holding positions.

The adjustment system may comprise a threaded adjustment member, such as a screw. The threaded adjustment member may suitably have a diameter of from 4 to 6 mm. It may, in one embodiment, have a 1 mm thread. In particular, it is preferred that the adjustment system comprises a double ended screw, also known as a left- and right-screw or a right- and left-screw. As the skilled reader will appreciate, such a screw has a first end portion with a right-hand screw thread and a second end portion with a left-hand screw thread, and a non-threaded section in the middle, between the two threaded end portions. This is a beneficial system because it means that the anterior guide member and the posterior guide member move simultaneously. This is the case both for movement towards the engagement member and away from the engagement member.

Additional Checking Devices to be Used with the Targeting Device

Optionally the targeting device described above is used in combination with a medial targeting device, e.g. as described in WO2019/224561. This device can be used to double check the alignment of the targeting kit in the antero-posterior plane before the tunnels are drilled.

When a medial targeting device is used, the targeting device is provided with an alignment slot located at the proximal end of the engagement member. This alignment slot is in longitudinal alignment with the engagement protrusion of the engagement member.

Optionally the targeting device described above is used in combination with an external targeting device, e.g. as described in WO2019/224561. This device can be used to double check the alignment of the targeting kit in the anterior-posterior plane before the tunnels are drilled.

In one embodiment, the external targeting device may comprise:

a targeting device interlocking portion, an alignment portion, and a holding arrangement for holding and pivoting the alignment portion relative to the targeting device interlocking portion, wherein the targeting device interlocking portion comprises a planar support body provided with:

an anterior guide member interlocking component, which comprises a first locking pin that extends from the planar support body in the same plane and can be received in the first angled channel or a first receiving channel adjacent thereto and aligned therewith, and a posterior guide member interlocking component, which comprises a second locking pin that extends from the planar support body in the same plane and can be received in the second angled channel or a second receiving channel adjacent thereto and aligned therewith, wherein the alignment portion comprises a planar elongate body having an angled tip at the distal end, and wherein the holding arrangement holds the planar elongate body and the planar support body in the same plane, but permits the pivotal movement of the planar elongate body relative to the planar support body within that plane, such that the first locking pin can be received in the first angled channel of the targeting device or a first receiving channel adjacent thereto and aligned therewith, and the second locking pin can be received in second angled channel of the targeting device or a second receiving channel adjacent thereto and aligned therewith, such that the planar support body is aligned with the anterior-posterior plane in which the first and second angled channels lie, and such that the planar elongate body is consequently also aligned with the anterior-posterior plane in which the first and second angled channels lie, such that the planar elongate body can be pivoted relative to the planar support body until the angled tip is alongside the implant and the plane of the angled tip can be compared to the centreline in the anterior-posterior plane, as determined via x-ray.

If the plane of the angled tip is not aligned with the centreline in the anterior-posterior plane, the location of the targeting device can be adjusted until the angled tip does align with the centreline in the anterior-posterior plane.

Cutting Tools to be Used with the Targeting Device

The access tunnels may be created using a tool that is elongate and has at least one edge that is sufficiently sharp that when the tool is operated it can be used to create access tunnels on the anterior and posterior of the implant. It may be a conventional tool, such as a drill and drill bits, or a chisel, or a reciprocating saw, or a K-wire.

It may preferably be that a chevron chisel according to WO2019/224561 is used. This chevron chisel comprises:

- an elongate body in the form of a flat plate having an upper face and a lower face, wherein the elongate body extends from a first elongate edge to a second elongate edge and having a proximal end that can be provided with a handle and having a distal end; and
- a cutting portion located at the distal end which comprises a first cutting face and a second cutting face which meet at an angled cutting point, wherein the first cutting face extends at an angle of from 30 to 60 degrees, (e.g. from 30 to 50 degrees, or from 40 to 50 degrees, or from 40 to 60 degrees), from the first elongate edge when measured with respect to the elongate axis of the elongate body, and the second cutting face extends at an angle of from 30 to 60 degrees, (e.g. from 30 to 50 degrees, or from 40 to 50 degrees, or from 40 to 60 degrees), from the second elongate edge when measured with respect to the elongate axis of the elongate body, and wherein the first cutting face extends at an angle of from 30 to 60 degrees, (e.g. from 30 to 50 degrees, or from 40 to 50 degrees, or from 40 to 60 degrees), from the lower face to the upper face, and wherein the second cutting face extends at an angle of from 30 to 60 degrees, (e.g. from 30 to 50 degrees, or from 40 to 50 degrees, or from 40 to 60 degrees), from the lower face to the upper face.

Preferably the angled cutting point is located substantially centrally between the first elongate edge and the second elongate edge.

In one embodiment, it is envisaged that the distal end of the chevron chisel has a 40 to 60 degree chisel angle, e.g. a 45 degree chisel angle or a 60 degree chisel angle.

Second Stage

The optional second stage of the procedure involves removing bony ingrowth located adjacent to the anterior access tunnel, and removing bony ingrowth located adjacent to the posterior access tunnel and the posterior surface of the implant. The intention of this step is to extend the size of the access tunnels.

Of course, it may be that the first stage creates initial access tunnels that are of sufficient size that the second stage can be omitted.

It may be that the anterior access tunnel is broadened in a plane that is substantially parallel to the anterior surface of the implant (increased width) and/or in a plane that is substantially perpendicular to the anterior surface of the implant (increased depth).

It may be that the posterior access tunnel is broadened in a plane that is substantially parallel to the posterior surface of the implant (increased width) and/or in a plane that is substantially perpendicular to the posterior surface of the implant (increased depth).

This may be carried out using another chevron chisel according to WO2019/224561, as described above. For example, a chevron chisel that is larger in at least one dimension than the tool used to make the access tunnel may suitably be used.

Alternatively, this step may be carried out using a chevron osteotome device of WO2019/224561. The chevron osteotome device of WO2019/224561 comprises:

- an elongate body having a proximal end that can be provided with a handle and a distal end, wherein the elongate body includes a distal section extending from the distal end to a shoulder point, wherein the shoulder point is located closer to the distal end than the proximal end;
- a cutting portion extending outwardly from both sides of the elongate body at the shoulder point, the cutting portion having a first angled cutting side that extends outwardly from one side of the elongate body at the shoulder point, and a second angled cutting side that extends outwardly from the opposite side of the elongate body at the shoulder point, wherein the cutting portion has a front face and a back face which are connected by the first angled cutting side and the second angled cutting side, the front face being aligned with and a continuation of the elongate body, and the back face being aligned with and a continuation of the elongate body, such that the cutting portion has the same depth as the elongate body, and wherein the front face and the back face are blunt;

such that the distal end of the chevron osteotome device can be located in an access tunnel and chevron osteotome device can be pushed in the direction of the distal end of the implant so as to cut away bony ingrowth on both sides of the access tunnel with the first angled cutting side and the second angled cutting side.

In one embodiment, the first stage creates initial access tunnels, anteriorly and posteriorly, and the second stage creates a sub access tunnel within each initial access tunnel. The sub access tunnel may be deeper than the initial access tunnel but less wide than the initial access tunnel. Each sub access tunnel may be sized to facilitate use of the wire delivery device in the fifth stage and therefore each may suitably be sized to receive one of the elongate bodies of the wire delivery device.

It may be that the initial access tunnels each have a maximum depth of about 1 to 2 mm, such as about 1 mm and they may optionally but preferably have a maximum width of about 4 to 12 mm, such as about 10 mm. It may be that the sub access tunnels each have a maximum depth of about 1.5 to 2 mm, such as about 1.5 mm and they may optionally but preferably have a maximum width of about 4 to 7 mm, such as about 5 mm.

Third Stage

The third stage of the procedure involves removing bony ingrowth located between the implant and the femur in the anterior aspect, and removing bony ingrowth located between the implant and the femur in the posterior aspect. The intention of this step is to reduce the amount of bony ingrowth between the implant and the femur in the anterior aspect and to reduce the amount of bony ingrowth between the implant and the femur in the posterior aspect.

In one embodiment, this step may clear a space at the bone-implant interface to both the medial and lateral edges of the implant.

This third stage may be carried using the curette device of WO2019/224561 (or a set of two or more curette devices according to WO2019/224561). The curette device of WO2019/224561 comprises:

an elongate body in the form of a flat plate that extends from a first elongate edge to a second elongate edge and having a distal end and a proximal end that can be provided with a handle;

a first cutting portion located at or near the distal end which extends outwardly from a first elongate edge of the elongate body, the cutting portion having a blunt edge and a cutting edge which meet at an angled cutting point, wherein the blunt edge extends from a first location on the elongate body to the cutting point and the cutting edge extends from a second location on the elongate body to the cutting point, wherein the first location is closer to the distal end than the second location and wherein the cutting edge is at an angle to the elongate axis of the curette device of from 50 to 85 degrees;

such that the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

The elongate body of the curette device suitably has a diameter that is equal to or slightly less than the diameter of the now-widened access tunnel. For example its diameter may be less than the diameter of the access tunnel by 1 mm or less, e.g. from 0.1 to 0.5 mm.

The cutting edge is located towards the proximal end of the cutting portion, i.e. such that cutting occurs as the curette device is withdrawn from the tunnel rather than as it is pushed into the tunnel.

The cutting edge may be sharp along its length, such that all of the cutting edge can serve to cut away bony ingrowth located between the access tunnel and the surface of the implant. However, it will be appreciated that the device will also be effective if only some of the length of the cutting edge is sharp. In the present invention, it is only necessary that the cutting edge is sharp at its distal end, i.e. the cutting point. Therefore the cutting edge is sharp at the cutting point and is optionally sharp along some, most or all of the remainder of the cutting edge.

In a preferred embodiment the curette device comprises a second cutting portion, located between the second elongate edge and the distal end of the elongate body. For example, a second cutting portion may be provided on a curved or angled edge that extends between the second elongate edge and the distal end of the elongate body. The second cutting portion suitably comprises teeth. Alternatively or additionally, the second cutting portion may comprise a sharp edge.

Fourth Stage

The fourth stage of the procedure involves clearing the lateral aspect of the implant by removing bony ingrowth located at the antro-lateral edge of the implant and at the postro-lateral edge of the implant. Thus the lateral surface of the implant is cleared of bony ingrowth at or near to where it adjoins the anterior surface of the implant and at or near to where it adjoins the posterior surface of the implant.

This stage may be carried out using the medial-lateral clearance device of WO2019/224561 (or a set of two or more medial-lateral clearance devices according to WO2019/224561). The medial-lateral clearance device of WO2019/224561 comprises:

an elongate body having a proximal end that can be provided with a handle and having a distal end, the elongate body being in the shape of a flat plate that extends from a first elongate edge to a second elongate edge;

a cutting portion extending outwardly from the elongate body and located at or near the distal end, the cutting portion having an inner surface that is flat and which connects with the first elongate edge of the elongate body at a substantially 90 degree angle, and having an outer surface that comprises an angled cutting face that is located towards the distal end of the elongate body, wherein the inner surface meets the angled cutting face at a cutting edge, at an angle of from 20 to 70 degrees;

such that the distal end of the flat plate elongate body can be located in a space at the bone-implant interface, at or near to the shoulder portion of the implant, with the flat plate being parallel to either the anterior surface or the posterior surface, and with the flat inner surface of the cutting portion aligned with either the medial or lateral surface of the implant, such that the medial-lateral clearance device can then be pushed in the direction of the distal end of the implant, with the flat plate elongate body remaining alongside the respective anterior or posterior surface, in the space at the bone-implant interface, whilst the angled cutting face cuts away bony ingrowth located at said medial or lateral surface of the implant as the device is pushed towards the distal end of the implant.

The cutting portion has an inner surface that is flat and which connects with the first elongate edge of the elongate body at a substantially 90 degree angle, e.g. at an angle of from 90 to 100 degrees.

In one embodiment, the distal end of the medial-lateral clearance device is blunt, e.g. it may be curved. In another embodiment, the distal end of the medial-lateral clearance device is angled, e.g. it may have a chevron shape. In one such embodiment, the distal end of the medial-lateral clearance device comprises a first angled face and a second angled face which meet at an angled point, wherein the first angled face extends at an angle of from 30 to 60 degrees, (e.g. from 30 to 50 degrees, or from 40 to 50 degrees, or from 40 to 60 degrees), from the first elongate edge when measured with respect to the elongate axis of the elongate body, and the second angled face extends at an angle of from 30 to 60 degrees, (e.g. from 30 to 50 degrees, or from 40 to 50 degrees, or from 40 to 60 degrees), from the second elongate edge when measured with respect to the elongate axis of the elongate body.

In one embodiment, it is envisaged that the distal end of the medial-lateral clearance device has a 40 to 60 degree chevron angle, e.g. a 45 degree chevron angle or a 60 degree chevron angle.

The cutting portion may be formed as an integral part of the medial-lateral clearance device. Alternatively, the cutting portion may be formed as a separate part that is then attached to the elongate body, e.g. by laser welding. The cutting portion is attached to connect with the first elongate edge of the elongate body at a substantially 90 degree angle, e.g. at an angle of from 90 to 100 degrees.

This stage may, alternatively, be carried out using the wire delivery device according to the invention, as described below. In other words, in one embodiment the wire delivery device according to the invention is used to clear the medial aspect of the implant and to clear the lateral aspect of the implant.

Fifth Stage

The fifth stage of the procedure involves clearing the medial aspect of the implant by removing bony ingrowth located at the antro-medial edge of the implant and at the postro-medial edge of the implant. Thus the medial surface of the implant is cleared of bony ingrowth at or near to where it adjoins the anterior surface of the implant and at or near to where it adjoins the posterior surface of the implant.

This stage is carried out using a wire delivery device according to the invention.

The novel wire delivery device of the invention comprises:

- a first elongate body that extends from a first elongate edge to a second elongate edge and that has an inner face and an outer face, the elongate body having a proximal end that can be provided with a handle and a distal end that may optionally be blunt, wherein there is a wire receiving portion provided in a spaced relationship with the distal end, wherein cutting wire can be located and secured in the wire receiving portion;
- a second elongate body that extends from a first elongate edge to a second elongate edge and that has an inner face and an outer face, the elongate body having a proximal end that can be provided with a handle and a distal end that may optionally be blunt, wherein there is a wire receiving portion provided in a spaced relationship with the distal end, wherein cutting wire can be located and secured in the wire receiving portion;

such that, in use, the elongate bodies can be positioned in a spaced apart and opposite but aligned configuration, and wherein a first length of cutting wire can be secured so as to extend from a location in the wire receiving portion of the first elongate body to a location in the wire receiving portion of the second elongate body, to provide a medial cutting wire arc extending between the first elongate body and the second elongate body, and wherein a second length of cutting wire can be secured so as to extend from a location in the wire receiving portion of the first elongate body to a location in the wire receiving portion of the second elongate body, to provide a lateral cutting wire arc extending between the first elongate body and the second elongate body, whereby the medial and lateral cutting wire arcs can then be used to cut, by pushing the first and second elongate bodies in an alternating motion in the desired direction of cutting.

By having a cutting wire arc both medially and laterally, the device drives distally along the midline axis of the implant and femur. This therefore makes the device more stable and easy to use, and avoids the device being driven into the medial cortex of the femur.

Although the first elongate body and the second elongate body may be different, in a preferred embodiment they have the same size and shape.

In one embodiment, the first elongate body is in the form of a flat plate and the second elongate body is in the form of a flat plate. In one embodiment the depth (thickness) of the plate is from 0.2 to 3 mm, such as from 0.5 to 2.5 mm, preferably from 1 to 2 mm, such as from 1 to 1.5 mm, e.g. 1 mm or 1.2 mm or 1.5 mm.

The distal end of each elongate body is not intended to be a cutting end and therefore these ends may be blunt. In one embodiment, distal end of each elongate body is angled but blunt, i.e. with no sharp edges. In one embodiment, each elongate body may have a chisel like distal end, e.g. with a 45 degree chisel end. This can be advantageous in terms of facilitating an easy transition into the bone-implant interface. Also, it will assist with keeping the wire delivery device pushed against the implant.

Each elongate body may be provided with an integral handle at its proximal end or may be provided with a handle at its proximal end in use.

Each elongate body may be formed from any suitable medical grade metal or metal alloy, e.g. medical grade stainless steel.

First Embodiment of the Novel Wire Delivery Device

In a first embodiment, the novel wire delivery device of the invention comprises:

- a first elongate body that extends from a first elongate edge to a second elongate edge and that has an inner face and an outer face, the elongate body having a proximal end that can be provided with a handle and a distal end that may optionally be blunt, wherein there is a first wire receiving slot provided in a spaced relationship with the distal end and located towards the first elongate edge, wherein the first wire receiving slot runs from an open entrance to a closed end, and wherein there is a second wire receiving slot provided in a spaced relationship with the distal end and located towards the second elongate edge, wherein the second wire receiving slot runs from an open entrance to a closed end;
- a second elongate body that extends from a first elongate edge to a second elongate edge and that has an inner face and an outer face, the elongate body having a proximal end that can be provided with a handle and a distal end that may optionally be blunt, wherein there is a first wire receiving slot provided in a spaced relationship with the distal end and located towards the first elongate edge, wherein the first wire receiving slot runs from an open entrance to a closed end, and wherein there is a second wire receiving slot provided in a spaced relationship with the distal end and located towards the second elongate edge, wherein the second wire receiving slot runs from an open entrance to a closed end;
- a first length of cutting wire extending from a first end to a second end, wherein the first end is secured in the first wire receiving slot of the first elongate body and the second end is secured in the first wire receiving slot of the second elongate body;
- a second length of cutting wire extending from a first end to a second end, wherein the first end is secured in the second wire receiving slot of the first elongate body and the second end is secured in the second wire receiving slot of the second elongate body;

such that, in use, the elongate bodies can be positioned in a spaced apart and opposite but aligned configuration, so that the first length of cutting wire provides a medial cutting wire arc, extending from the open entrance of the first wire receiving slot of the first elongate body to the open entrance of the first wire receiving slot of the second elongate body, and so that the second length of cutting wire provides a lateral cutting wire arc, extending from the open entrance of the second wire receiving slot of the first elongate body to the open entrance of the second wire receiving slot of the second elongate body, whereby the medial and lateral cutting wire arcs can then be used to cut, by pushing the first and second elongate bodies in an alternating motion in the desired direction of cutting.

The length of each elongate body may, for example, be 200 mm or more, such as from 200 mm to 300 mm, e.g. from 225 mm to 250 mm.

The maximum width of each elongate body (not including any handle) may suitably be from 6 mm to 10 mm, especially from 7 mm to 9 mm, e.g. about 7.5 mm or about 7.75 mm.

In one embodiment, each elongate body includes a narrower portion towards the distal end. In particular, there may be a narrowing of the width of the elongate body at or near to the location where the wire receiving slots are provided. For example, each elongate body may include a tapered portion at or near to the location where the wire receiving slots are provided.

Each elongate body may, for example, include a narrower portion with a width of from 2.5 mm to 6 mm, e.g. from 3 mm to 5 mm.

In one embodiment, for each elongate body the first wire receiving slot is defined between a first elongate outer wall and the first elongate edge, and the second wire receiving slot is defined between a second elongate outer wall and the second elongate edge.

It may be that for each elongate body the first elongate outer wall is 0.3 mm to 1 mm thick, e.g. about 0.5 mm thick, and the second elongate outer wall is 0.3 mm to 1 mm thick, e.g. about 0.5 mm thick.

In one embodiment, for each elongate body the first wire receiving slot may be from 1 mm to 2 mm wide, e.g. about 1.6 mm wide and may be from 5 mm to 10 mm long, e.g. about 8 mm long. For each elongate body the second wire receiving slot may be from 1 mm to 2 mm wide, e.g. about 1.6 mm wide and may be from 5 mm to 10 mm long, e.g. about 8 mm long.

In one embodiment, for each elongate body the first wire receiving slot extends substantially parallel to the elongate axis of the elongate body. In one embodiment, for each elongate body the second wire receiving slot extends substantially parallel to the elongate axis of the elongate body. However, it could be envisaged that the first wire receiving slot and/or the second wire receiving slot extends at an angle to the elongate axis of the elongate body, such as an angle of up to 30°.

For each elongate body, the blunt distal end may be any suitable shape but in one embodiment it is tapered, e.g. it may taper to a curved end.

In one embodiment, for each elongate body the closed end of the first wire receiving slot may be 2 mm to 10 mm or more from the distal end, e.g. from 3 mm to 8 mm from the distal end, such as about 5.2 mm from the distal end. In one embodiment, for each elongate body the closed end of the second wire receiving slot may be 2 mm to 10 mm or more from the distal end, e.g. from 3 mm to 8 mm from the distal end, such as about 5.2 mm from the distal end.

Suitably, each elongate body may be laser cut. However, the invention is not limited to use of this manufacturing technique.

Suitably, each elongate body may be formed from medical grade stainless steel, such as stainless steel 420 hardened. Medical grade stainless steel is known in the art.

The dimensions of the wires may be chosen by the skilled person. The invention is not limited to any particular size.

The medial cutting wire arc and the lateral cutting wire arc are suitably formed from wire with a diameter of from 0.5 to 1 mm, preferably 0.6 mm to 1 mm, e g. from 0.7 mm to 0.8 mm.

The length of the medial cutting wire arc is suitably from 50 to 100 mm, such as from 50 to 90 mm or from 50 mm to 80 mm, e.g. from 60 to 70 mm or from 80 to 90 mm. The length of the lateral cutting wire arc is suitably from 50 to 100 mm, such as from 50 to 90 mm or from 50 mm to 80 mm, e.g. from 60 to 70 mm or from 80 to 90 mm.

The wire to be used for the medial cutting wire arc and the lateral cutting wire arc must be strong and not brittle. It is therefore useful for the wire to be annealed, allowing it to be flexible. It may suitably be cable rope wire formed from stainless steel or titanium or titanium alloy. Medical grade stainless steel and titanium and titanium alloy wires are known in the art. Examples of suitable wire include Grade I titanium annealed and stainless steel annealed, e.g. stainless steel 321 annealed, or alternatively 1×19 strand 316 stainless steel (ss) or 1×19 strand 304 ss or DPD 189A ss. These have the strength and flexibility that is necessary to carry out the procedure. Any other wire having similar properties can be used.

It is envisaged that in one embodiment the wire to be used for one or both of the medial cutting wire arc and the lateral cutting wire arc is Gigli wire (e.g. with a diameter in the range of from 0.8 mm to 1 mm). Gigli wire may be chosen due its improved priorities in cutting through bone. In one embodiment, the wire for the medial cutting wire arc and the lateral cutting wire arc is Gigli wire. In another embodiment, the wire for the medial cutting wire arc is Gigli wire and the wire for the lateral cutting wire arc is titanium, e.g. Grade I titanium annealed.

The ends of the medial cutting wire arc and the lateral cutting wire arc are suitably secured in the respective receiving slots by laser welding. However, other techniques for securing the wires in the slots can be contemplated.

Suitably, each end of the medial cutting wire arc and the lateral cutting wire arc is crimped in a ferrule. Ferrule crimping is well known in the art.

In one embodiment, a ferrule is positioned in each respective wire receiving slot and a first portion of the length of the ferrule (at the closed end of the wire receiving slot) is welded in place. A second portion of the length of the ferrule (located at or extending from the open entrance of the wire receiving slot) is not welded and thus its lumen remains open. Therefore, each end of the cutting wire arc is fed into the lumen of a respective second portion of the ferrule and can then be crimped. Therefore, the ferrule is secured in the wire receiving slot by welding, and the wire is secured in the ferrule by crimping. The ferrule clearly should be sized such that at least the first portion of its length fits in the respective wire receiving slot.

In another embodiment, each end of the cutting wire arc is fed into a ferrule and crimped, and the ferrule is welded in place in its respective wire receiving slot. The ferrule clearly should be sized such that, when crimped, the flat surface of crimped ferrule fits in the respective wire receiving slot.

The length of the ferrule may be chosen by the skilled person. The invention is not limited to any particular size.

In one embodiment, the length of the ferrule may be from 10 to 20 mm long, especially from about 12 to 19 mm, e.g. from about 14 mm to 18 mm long, such as about 16 or 17 mm long. It may be convenient for the length of the ferrule to be long enough that a first portion of the ferrule length is used for welding the ferrule into place in the wire receiving slot and a second portion of the ferrule length is used for receiving the wire. For example, the first portion of the ferrule length may be from about 5 to 12 mm long (e.g. from about 7 to 11 mm) and the second portion of the ferrule length may be from about 5 to 12 mm long (e.g. from about 6 to 10 mm).

In another embodiment, the length of the ferrule may be from 6 to 12 mm long, e.g. about 8 mm to 9 mm long. It may be convenient for the length of the ferrule to be about 1 mm more than the length of the respective wire receiving slot. Each end of the cutting wire arc can then be fed into a ferrule and crimped, and the ferrule is welded in place in its respective wire receiving slot.

In one embodiment, the cutting wire has a diameter of 0.7 mm to 0.8 mm and the ferrule is 18 gauge, with an outer diameter of 1.27 mm and an inner diameter of 0.84 mm.

In one embodiment, the cutting wire has a diameter of 0.8 mm to 1 mm and the ferrule is 18 gauge, with an outer diameter of 1.27 mm and an inner diameter of 1.07 mm.

When using the first wire delivery device of the invention, the medial and lateral cutting wire arcs can be used to cut by:

locating the first and second elongate bodies in the anterior and posterior access tunnels, locating the medial cutting wire arc on the medial side of the implant and locating the lateral cutting wire arc on the lateral side of the implant, pushing the first and second elongate bodies in an alternating motion in the desired direction of cutting, into the space that has already been created by the previous steps, to cause the medial cutting wire arc to cut through the medial part of the femur, beneath the medial shoulder and to cause the lateral cutting wire arc to cut through the lateral part of the femur, beneath the lateral shoulder.

If the implant is collared, it will be appreciated that the medial cutting wire arc must be located on the medial side of the implant in a position inferior to the collar, e.g. it may be hooked over the collar.

As noted above, in one preferred embodiment sub access tunnels have been formed for receiving the first and second elongate bodies, and therefore in one preferred embodiment the first and second elongate bodies are located in and pushed along these sub access tunnels.

The cutting wire arcs will not be directly exposed to the bone because they are secured in the wire receiving slots and these are spaced from the distal end. The distal end is therefore usefully blunt, to protect the bone from the wire. However, it is also envisaged that the distal ends of the first and second elongate bodies may be chisel like, e.g. with a 45 degree chisel angle. This can be advantageous in terms of facilitating an easy transition into the bone-implant interface. Also, it will assist with keeping the wire delivery device pushed against the implant.

The first and second elongate bodies are pushed in an alternating motion to cause the cutting wire arcs to cut, directing the force distally. As the medial cutting wire arc traverses distally, it will clear the bone-implant interface medially As the lateral cutting wire arc traverses distally, it will clear the bone-implant interface laterally. The distal movement of the first and second elongate bodies may be carried out manually, e.g., using a hammer, or a reciprocating mechanism (e.g. reciprocating saw) could be used to drive each of the first and second elongate bodies.

The first and second elongate bodies may, for example, be driven distally in an alternating motion 10 mm at a time until the tip of the device is at least 10 mm, preferably at least 30 mm, beyond the tip of implant. The first and second elongate bodies can suitably be driven distally using a hammer or power instruments e.g., a reciprocating saw-powered hand piece.

The implant will then be cleared of any bony ingrowth circumferentially around the implant. The implant is removed and then the wire delivery device can be removed.

Second Embodiment of the Novel Wire Delivery Device

In an alternative (second) embodiment, the novel wire delivery device of the invention comprises:

a first elongate body that extends from a first elongate edge to a second elongate edge and that has an inner face and an outer face, the elongate body having a proximal end that can be provided with a handle and a distal end that may optionally be blunt, where there is a first wire guidance channel provided in a spaced relationship with the distal end and located within the first elongate body, wherein the first wire guidance channel runs from an entrance at the first elongate edge to an exit at the second elongate edge, and wherein either the inner face or the outer face includes a first mouth portion to access the first wire guidance channel and a first engagement protrusion adjacent to the first mouth portion for engaging with a first part of a wire loop and securing this part of the wire loop within the first wire guidance channel;

a second elongate body that extends from a first elongate edge to a second elongate edge and that has an inner face and an outer face, the elongate body having a proximal end that can be provided with a handle and a distal end that may optionally be blunt, where there is a second wire guidance channel provided in a spaced relationship with the distal end and located within the second elongate body, wherein the second wire guidance channel runs from an entrance at the first elongate edge to an exit at the second elongate edge, and wherein either the inner face or the outer face includes a second mouth portion to access the second wire guidance channel and a second engagement protrusion adjacent to the second mouth portion for engaging with a second part of a wire loop and securing this part of a wire loop within the second wire guidance channel;

such that, in use, a wire loop can be provided and a first part of the wire loop can be fed into the first wire guidance channel via the first mouth portion and secured therein by engagement with the first engagement protrusion and a second part of the wire loop can be fed into the second wire guidance channel via the second mouth portion and secured therein by engagement with the second engagement protrusion, and the elongate bodies can be positioned in a spaced apart and opposite but aligned configuration, so that the wire loop provides a medial cutting wire arc from the exit of the first wire guidance channel to the entrance of the second wire guidance channel and provides a lateral cutting wire arc from the exit of the second wire guidance channel to the entrance of the first wire guidance channel, whereby the cutting wire arcs can then be used to cut by pushing the first and second elongate bodies in an alternating motion in the desired direction of cutting.

Each wire guidance channel is suitably located about 1 to 4 mm from the distal end. It may suitably be located substantially centrally in relation to the thickness of the plate but it may alternatively be off-centre. Each wire guidance channel may suitably have a depth of about 0.5 to 1.5 mm, or from 0.5 to 1 mm, e.g. about 0.7 mm or 0.8 mm; clearly the depth of the channel must be less than the depth (thickness) of the plate.

Each wire guidance channel runs from an entrance at the first elongate edge to an exit at the second elongate edge. If the channel is straight and runs perpendicular to the elongate axis of the elongate body, the length of the channel is the same as the distance between the first elongate edge and the second elongate edge (the width of the elongate body). However, it is also envisaged that the channel may be angled or curved or may comprise a combination of angled portions and/or curved portions and/or straight (perpendicular) portions. Therefore the length of the path travelled by the channel from the entrance to the exit may be greater than the width of the elongate body.

In relation to the wire guidance channel, the use of straight edges perpendicular to the elongate axis of the elongate body can be beneficial in terms of ease of manufacture. The use of angles (provided that these are not right angles) and/or curves can be beneficial in terms of reducing the risk of damage to the wire. It may be preferred that right angles are avoided, to reduce the risk of damage to the wire.

Each wire guidance channel may suitably have a height of from about 0.5 mm to 4 mm, such as 1 mm to 4 mm, e.g. about 2 mm.

The mouth portion that provides access to the wire guidance channel from the inner face or outer face must have a height that is at least equal to the diameter of the wire, so that the wire can be fed through the mouth portion into the wire guidance channel. In one embodiment, each mouth portion may have a height of from 0.5 mm to 1.5 mm or from 0.5 mm to 1 mm, e.g. about 0.6 mm or 0.7 mm or 0.8 mm.

Each mouth portion may be straight or may be curved or angled or combinations thereof. It may be straight and run perpendicular to the elongate axis of the elongate body. It may be angled or curved or may comprise a combination of angled portions and/or curved portions and/or straight (perpendicular) portions.

The use of straight edges perpendicular to the elongate axis of the elongate body can be beneficial in terms of ease of manufacture. The use of angles (provided that these are not right angles) and/or curves can be beneficial in terms of reducing the risk of damage to the wire.

Each engagement protrusion may be any suitable shape. It may, for example, be a shape that has straight edges, such as rectangular or square, or it may be a shape with angled edges, such as a triangle or a truncated triangle, or it may be a shape with curved edges, such as a tongue shape. It may include combinations of straight edges and/or, angled edges and/or curved edges. Each engagement protrusion may extend for part or all the distance from the first elongate edge to the second elongate edge. In one embodiment it extends across only part of width of the elongate body and is located substantially centrally between the first elongate edge and the second elongate edge. In another embodiment it extends across the full width of the elongate body.

In one embodiment, each channel is straight and runs perpendicular to the elongate axis of the elongate body. It may be that each mouth portion is also straight and runs substantially perpendicular to the elongate axis of the elongate body. Each mouth portion may, therefore, be rectangular in shape. Each corresponding engagement protrusion may also be a shape with straight edges and may have an edge that runs substantially perpendicular to the elongate axis of the elongate body. Each corresponding engagement protrusion may, therefore, be rectangular in shape and can be considered as a rectangular overhang. Each corresponding engagement protrusion may extend for part or all the distance from the first elongate edge to the second elongate edge; in one embodiment it extends across the full width of the elongate body. This design is beneficial in terms of case of manufacture.

In another embodiment, each channel is curved or includes a curved portion; it may, for example, include a "U" shape or a circular shape or other curved shape. It may be that each mouth portion is curved and may, for example, include a "U" shape or a Major arc or other curved shape. In one embodiment the "U" shape or Major arc or other curved shape is located substantially centrally between the first elongate edge and the second elongate edge. Each corresponding engagement protrusion may also be (or comprise) a curved shape and may, for example, be a tongue shaped overhang. Each corresponding engagement protrusion may extend for part or all the distance from the first elongate edge to the second elongate edge; in one embodiment it extends across only part of width of the elongate body and is located substantially centrally between the first elongate edge and the second elongate edge. This design is beneficial in terms of reducing the risk of damage to the wire.

In general, allowing the wire to lie in a curved channel means that there is smooth transference of loading of the wire as the instruments are driven down.

In another embodiment, each channel is angled or includes an angled portion; it may, for example, include a "V" shape or other angled shape. It may be that each mouth portion is angled and may, for example, include a "V" shape or other angled shape. In one embodiment the "V" shape or other angled shape is located substantially centrally between the first elongate edge and the second elongate edge. Each corresponding engagement protrusion may also be (or comprise) an angled shape and may, for example, be a triangular (or truncated triangular) shaped overhang. Each corresponding engagement protrusion may extend for part or all the distance from the first elongate edge to the second elongate edge; in one embodiment it extends across only part of width of the elongate body and is located substantially centrally between the first elongate edge and the second elongate edge.

In one embodiment, each channel includes a combination of curved and angled portions. In particular, it may be advantageous to have a central curved portion and an angled portion on each side of the central curved portion. It may be that each mouth portion includes a combination of curved and angled portions, e.g. a substantially central "U" shape or Major arc or other curved shape and an angled portion on each side. Each corresponding engagement protrusion may also be (or comprise) a curved shape and may, for example, be a tongue shaped overhang. Each corresponding engagement protrusion may extend for part or all the distance from the first elongate edge to the second elongate edge; in one embodiment it extends across only part of width of the elongate body and is located substantially centrally between the first elongate edge and the second elongate edge. This design is beneficial in terms of reducing the risk of damage to the wire.

Using a curved and/or angled configuration (without any right angles) reduces the risk of the wire being damaged, especially at the entry and exit points to the channel.

It will be appreciated that a range of shapes and sizes for each mouth portion and corresponding engagement protrusion could be used and that what is most important is that the wire can fit through the mouth portion to be fed into the wire guidance channel but that the wire can then engage with, and be secured in place by, the engagement protrusion.

Due to the fact that, in use, the wire delivery device will be pushed in the direction of the distal ends of the elongate bodies, it is preferred that the mouth portion is closer to the distal end than the engagement protrusion. This will facilitate the engagement protrusion keeping the wire in place during use.

The wire delivery device of the invention may suitably be provided together with a wire loop, although it will be appreciated that the user may obtain a wire loop independently.

The wire delivery device of the invention may be provided together with two or more wire loops (e.g. three or more wire loops) of different sizes and/or different materials to allow the user to select a suitable size or material. In particular, different size loops may be beneficial to allow the user to select a circumference of wire loop that fits over the implant in question. For example, circumferences of 70 mm, 85 mm and 100 mm could be provided.

In other words, there may be a wire delivery kit provided, comprising the wire delivery device of the invention together with one or more wire loop.

In general, the wire loop may have a circumference in the range of from 60 to 120 mm, such as from 70 to 100 mm. The wire loop is suitably provided in a form where it is already in a loop shape, but it may be that the loop is formed in situ. The user is capable of securing a wire into a loop shape when desired.

In one embodiment, the wire delivery device of the invention is provided with the wire loop already located and secured in the first and second wire guidance channels, so that the wire loop provides a medial cutting wire arc from the exit of the first wire guidance channel to the entrance of the second wire guidance channel and provides a lateral cutting wire arc from the exit of the second wire guidance channel to the entrance of the first wire guidance channel.

However, it will be appreciated that this is not essential, and the wire loop can be provided in a free-standing form and can then be located and secured in the first and second wire guidance channels by the user when desired.

The wire to be used in the wire loop must be strong and not brittle. It may suitably be cable rope wire formed from stainless steel or titanium or titanium alloy. Medical grade stainless steel and titanium and titanium alloy wires are known in the art. Examples of suitable wire include 1×19 strand 316 stainless steel (ss) or 1×19 strand 304 ss or DPD 189A ss or Grade I titanium annealed. These have the strength and flexibility that is necessary to carry out the procedure.

It is envisaged that in one embodiment the wire to be used is Gigli wire (e.g. with a diameter in the range of from 0.8 mm to 1 mm). Gigli wire may be chosen due its improved priorities in cutting through bone.

The cable rope wire may be 0.5 to 1.5 mm diameter, e.g. 0.8 to 1.5 mm diameter or 0.5 to 1 mm diameter. The thickness should be chosen taking into account the size and shape of the mouth portion and engagement protrusion because the wire must be able to fit through the mouth portion but also be secured in the channel by the engagement protrusion.

The wire loop is suitably formed by bringing together the two end sections of a length of medical grade wire and then crimping them to form a closed circle (wire loop). One or more metal ferrule may be used to enclose the two end sections before then crimping. Ferrule crimping is well known in the art.

If a single ferrule is used to enclose the two end sections, then the diameter of the ferrule used to crimp the ends should be such that it allows both ends of wire to slide past each other and protrude slightly on either side of the ferrule. Preferably, when crimped, the flat surface of crimped ferrule fits tightly proximally and distally and also medially and laterally in the wire guidance channel.

In one embodiment, in use, the crimped ferrule is located in a wire guidance channel. This assists with stability as the cutting action takes place and prevents the wire itself being damaged at the entry and exit points of the wire guidance channel during use. This is a suitable arrangement when the wire guidance channel is straight.

In one such embodiment, a second metal ferrule is provided on the wire loop, at a location diametrically opposite from the ferrule used for crimping the ends together. This has the benefit that one ferrule can be located in each wire guidance channel. This assists with stability as the cutting action takes place and prevents the wire itself being damaged at the entry and exit points of the wire guidance channel during use.

In another embodiment, in use, the crimped ferrule is located on the lateral side of the implant, i.e. in a location where the surface of the implant has already been cleared. This ensures that on the medial side, where cutting is taking place, there is a full arc of cutting wire uninterrupted by ferrule material.

As an alternative to enclosing the two end sections in a single metal ferrule before then crimping, each end section can be placed in a separate metal ferrule, each is then crimped, and then the ferrules with the crimped wire can be laser welded together. This allows a smaller diameter ferrule to be used and so in turn presents a smaller overall diameter of the crimped wires, which can be useful for ease of movement when cutting into the cancellous bone.

In general, the invention is not limited to the nature of the wire or how the wire loop is formed. It is within the skilled person's ability to select a suitable wire and form it into a loop.

It is also possible to use more than one wire loop at a time or to provide a wire loop that has a double thickness of wire forming the closed circle. The limiting factor is that the wire loop or loops must be able to fit in the wire guidance channel. If each section of wire used has too small a diameter it will not be strong enough. If the wire guidance channel is made bigger, to accommodate a greater diameter of wire, then the walls defining this channel within the elongate body will need to be made thinner in order to still keep the elongate bodies an overall size that can fit down the access tunnels as formed. This will be detrimental to the strength of the apparatus.

The first mouth portion can be located on the inner face or outer face of the first elongate body, and the second mouth portion can be located on the inner face or outer face of the second elongate body. For ease of use it is preferred that the same configuration is used for both elongate bodies, i.e. either: (a) the first mouth portion is located on the inner face of the first elongate body and the second mouth portion is located on the inner face of the second elongate body or (b) the first mouth portion is located on the outer face of the first elongate body and the second mouth portion is located on the outer face of the second elongate body.

In one embodiment, the first mouth portion is located on the outer face of the first elongate body and the second mouth portion is located on the outer face of the second elongate body. This can be beneficial in that as the first and second elongate bodies are pushed down the tunnels, the wire is additionally secured in place by the tunnel walls.

When using the wire delivery device of the second embodiment, once the wire loop is located and secured in the first and second wire guidance channels, the wire loop can be used to cut by:

- locating the wire loop around the implant, with the first and second elongate bodies in the anterior and posterior access tunnels, and
- pushing the first and second elongate bodies in an alternating motion in the desired direction of cutting, into the space that has already been created by the previous steps, to cause the medial cutting wire arc to cut through the medial part of the femur, beneath the shoulder.

As noted above, in one preferred embodiment sub access tunnels have been formed for receiving the first and second elongate bodies, and therefore in one preferred embodiment the first and second elongate bodies are located in and pushed along these sub access tunnels.

The wire loop will not be directly exposed to the bone because it is secured in the wire guidance channels and these are spaced from the distal end. The distal end is therefore usefully blunt, to protect the bone from the wire. However, it is also envisaged that the distal ends of the first and second elongate bodies may be chisel like, e.g. with a 45 degree chisel angle. This can be advantageous in terms of facilitating an easy transition into the bone-implant interface. Also, it will assist with keeping the wire delivery device pushed against the implant.

The first and second elongate bodies are pushed in an alternating motion to cause the wire loop to cut, directing the force distally. As the wire traverses distally, it will clear the bone-implant interface medially. The distal movement of the first and second elongate bodies may be carried out manually, or a reciprocating mechanism could be used to drive each of the first and second elongate bodies.

The first and second elongate bodies may, for example, be driven distally in an alternating motion 10 mm at a time until the tip of the device is 10 mm beyond the tip of implant. The first and second elongate bodies can suitably be driven distally using a hammer or power instruments e.g. a reciprocating saw-powered hand piece.

Optional Equipment

In one embodiment, a universal handle is provided which can be used as a handle for two or more of the devices described above, except for the targeting device which it will be appreciated does not require a handle. The universal handle may comprise a body having one or more grip portions at its proximal end and an engagement recess, such as a slot, at its distal end. The engagement recess is sized and shaped to receive the proximal end of the devices described above, except for the targeting device. In this regard, it will be appreciated that said devices may each be provided with a proximal end having the same size and shape, e.g. a flat plate, and the engagement recess of the universal handle is sized and shaped to receive this proximal end. In one embodiment, all of the devices included in the kit apart from the targeting device have the same size and shape of distal end, and thus the universal handle can be used as the handle for all of these devices.

In one embodiment, the universal handle has a block shaped head. It may, for example, be a cube or a cuboid shape. This can facilitate the use of a hammer to apply distal force to a device (e.g. a curette device, a medial-lateral clearance device, a chevron chisel, or a wire delivery device) via the handle. It will be appreciated that the handle could also be configured to be used with a reciprocating saw in order to provide the distal force via the handle. A reciprocating saw could usefully be used to apply distal force to a medial-lateral clearance device, a chevron chisel, or a wire delivery device.

In one embodiment, 10-30 mm, e.g. about 20 mm, of the elongate length of the cutting tool is located in the handle, e.g. in the block shaped head.

In one embodiment, a brace sleeve is provided which can be used to provide structural support for the elongate body of any of the devices described above, except for the targeting device which it will be appreciated does not have an elongate body. The brace sleeve may comprise two elongate faces which are joined at one elongate edge and are open at the opposite elongate edge and at the two ends, so as to create an elongate cavity between the two faces within which an elongate body can be received. The brace sleeve can slide onto and over an elongate body to provide additional strength and resistance to bending during use. The brace sleeve can cover some, most or all of the length of an elongate body of any of the devices described above.

One or more brace sleeve can alternatively or additionally be used to provide structural support for a handle located at the proximal end of the elongate body. One or more brace sleeves of different lengths can be used.

As noted above, in one embodiment, a hammer is used to apply distal force to a device (e.g. a curette device, a medial-lateral clearance device, a chevron chisel, or a wire delivery device) via the handle. In such embodiments, the universal handle may have a block shaped head; it may, for example, be a cube or a cuboid shape. The use of one or more brace sleeves on the handle is particularly beneficial in such embodiments, as it reduces the likelihood of the device bending on hammering the device to apply distal force.

In some embodiments there is a brace sleeve that extends over the boundary between the handle and the elongate body. This boundary can otherwise be a potential point of weakness. Therefore it can be beneficial to include a brace that covers some, most or all of the length of an elongate body of any of the devices described above and covers some, most or all of the length of handle attached to said elongate body.

In one embodiment, therefore, the brace sleeve is attached to the handle and is attached to the elongate body.

It may be that a set of brace sleeves of different lengths is provided. The brace sleeve that is initially used can then be exchanged for a shorter brace sleeve as the tool moves distally inside the patient's body, and thus the length of cutting tool that remains outside the patient's body gets shorter.

In one embodiment, for example, a brace sleeve of a first length (e.g. 185 mm long) can be attached to provide support for the handle and elongate body of a cutting tool. The tool can be hammered in distally until the exposed length of the cutting tool (e.g. 50-55 mm of cutting tool) has been hammered in. Then the brace is removed. A second brace sleeve having a second (shorter) length (e.g. 130 mm long) can then be attached to provide support for the handle and elongate body of the cutting tool. The tool can be hammered in distally until the exposed length of the cutting tool (e.g. 50-55 mm of cutting tool) has been hammered in. Then the brace is removed. A third brace sleeve having a third (shorter) length (e.g. 70 mm long) can then be attached to provide support for the handle and elongate body of the cutting tool.

DESCRIPTION OF THE DRAWINGS

The invention will now be further described with reference to the drawings, which are exemplary of the invention rather than limiting, and in which.

Figures 1A, 1B:
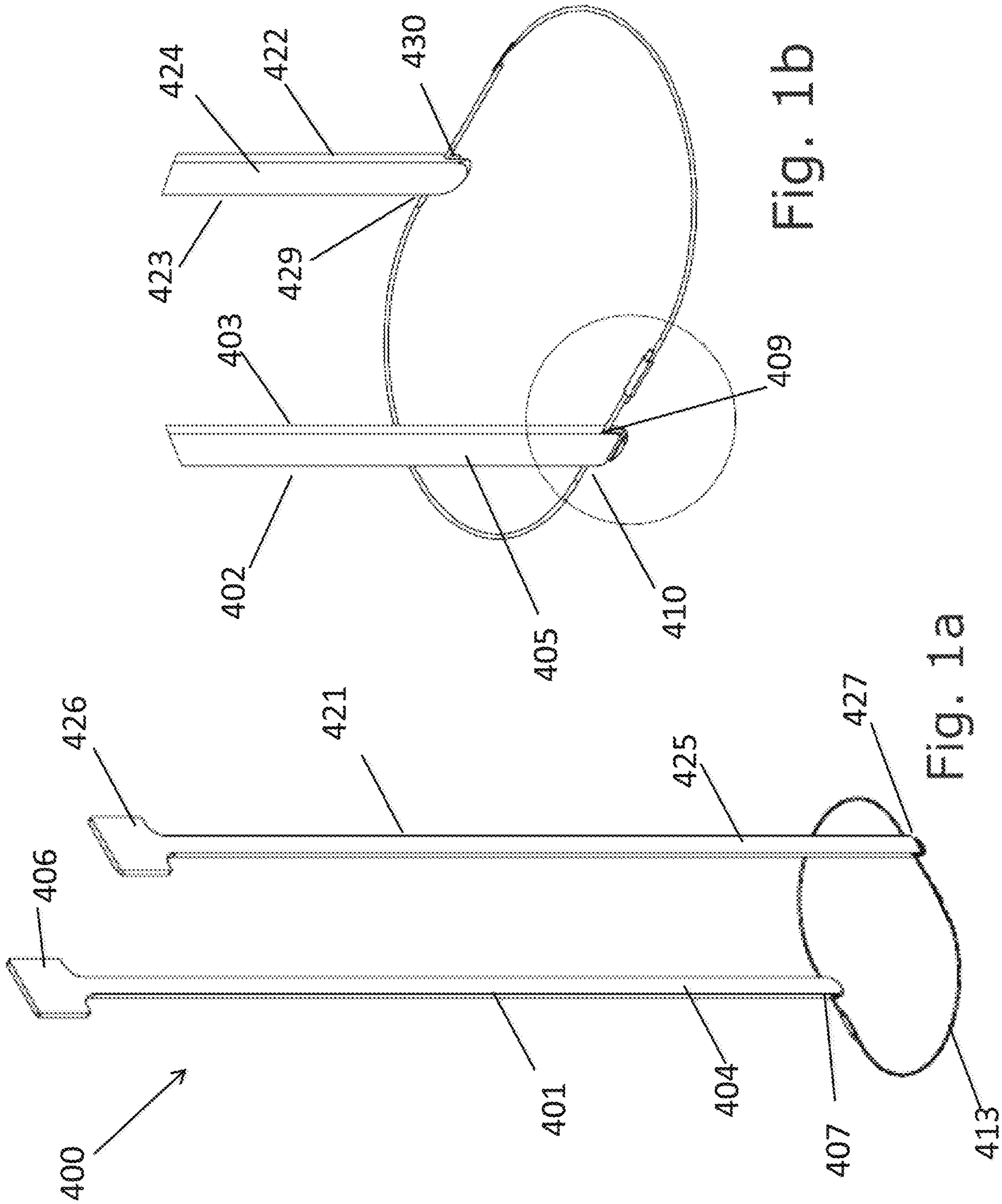
FIG. 1*a* is a perspective view of a wire delivery device of the invention
FIG. 1*b* is a close-up of the lower portion of the device shown in FIG. 1*a*

Various embodiments of the wire delivery device 400, 1400 of the invention are shown in FIGS. 1, 2, 13, 14 and 15. The device can be used in removing bony ingrowth from an implant, such as a femoral implant, and is in particular useful for collared implants—although not exclusively so.

The device has a first elongate body 401, 1401 that extends from a first elongate edge 402, 1402 to a second elongate edge 403, 1403 and that has an inner face 404, 1404 and an outer face 405, 1405. The elongate body has a proximal end 406, 1406 that can be provided with a handle and a distal end 407, 1407 that is blunt or that may be sharp.

There is also second elongate body 421, 1421 that extends from a first elongate edge 422, 1422 to a second elongate edge 423, 1423 and that has an inner face 424, 1424 and an outer face 425, 1425. The elongate body has a proximal end 426, 1426 that can be provided with a handle and a distal end 427, 1427 that is blunt or that may be sharp.

In the first embodiment, as shown in FIG. 15, the following applies.

The first elongate body 1401 is provided with a first wire receiving slot 1408*a* and a second wire receiving slot 1408*b*. The first wire receiving slot 1408*a* is provided in a spaced relationship with the distal end 1407 and it is located towards the first elongate edge 1402. The first wire receiving slot 1408*a* runs from an open entrance 1408*ai* to a closed end 1408*aii*. The second wire receiving slot 1408*b* is provided in a spaced relationship with the distal end 1407 and it is located towards the second elongate edge 1403. The second wire receiving slot 1408*b* runs from an open entrance 1408*bi* to a closed end 1408*bii*.

The second elongate body 1421 is provided with a first wire receiving slot 1428*a* and a second wire receiving slot 1428*b*. The first wire receiving slot 1428*a* is provided in a spaced relationship with the distal end 1427 and it is located towards the first elongate edge 1422. The first wire receiving slot 1428*a* runs from an open entrance 1428*ai* to a closed end 1428*aii*. The second wire receiving slot 1428*b* is provided in a spaced relationship with the distal end 1427 and it is located towards the second elongate edge 1423. The second wire receiving slot 1428*b* runs from an open entrance 1428*bi* to a closed end 1428*bii*.

Each elongate body includes a tapered portion 1435 near to the location where the wire receiving slots are provided.

For each elongate body the first wire receiving slot 1408*a*, 1428*a* is defined between a first elongate outer wall and the first elongate edge, and the second wire receiving slot 1408*b*, 1428*b* is defined between a second elongate outer wall and the second elongate edge.

There is a first length of cutting wire 1413*a* having its first end secured in the first wire receiving slot 1408*a* of the first elongate body and having its second end secured in the first wire receiving slot 1428*a* of the second elongate body.

There is a second length of cutting wire 1413*b* having its first end secured in the second wire receiving slot 1408*b* of the first elongate body and having its second end secured in the second wire receiving slot 1428*b* of the second elongate body.

Each end of the medial cutting wire 1413*a* and the lateral cutting wire 1413*b* is crimped in a ferrule 1440 and is laser welded into its respective wire receiving slot.

In the configuration shown in FIGS. 15*a-d*, the ferrule is only slightly longer than the wire receiving slot (e.g. about 1 mm longer). In this embodiment, each end of the cutting wire arc is fed into a ferrule and crimped, and the ferrule is welded in place in its respective wire receiving slot.

In the alternative configuration shown in FIGS. 15*g-j*, the ferrule is substantially longer than the wire receiving slot (e.g. about 5 mm to 10 mm longer). In this embodiment, a first portion of the length of the ferrule, which is within the wire receiving slot, is welded in place. A second portion of the length of the ferrule, which extends from the open entrance of the wire receiving slot, is not welded and thus its lumen remains open. Therefore, each end of the cutting wire arc is fed into the lumen of a respective second portion of the ferrule and can then be crimped. Therefore, the ferrule is secured in the wire receiving slot by welding, and the wire is secured in the ferrule by crimping.

In the alternative configuration shown in FIGS. 15*g-j*, the distal end 1407, 1427 of each elongate body 1401, 1421 is also shown as being chisel like, with a 45-degree angled end. However, it could be blunt, as shown in FIGS. 15*a-e*, if desired. A different angle other than 45 degrees could also be chosen, e.g. 60 degrees.

Likewise, whilst in the configuration shown in FIGS. 15*a-e* the distal end 1407, 1427 of each elongate body 1401, 1421 is shown as being blunt, it could be chisel like, e.g with a 45-degree angled end, as shown in FIGS. 15*g-j*, if desired. A different angle other than 45 degrees could also be chosen, e.g. 60 degrees.

In the first embodiment, as shown in FIG. 15, the elongate bodies can be positioned in a spaced apart and opposite but aligned configuration, so that the first length of cutting wire 1413*a* provides a medial cutting wire arc, extending from the open entrance of the first wire receiving slot of the first elongate body to the open entrance of the first wire receiving slot of the second elongate body, and so that the second length of cutting wire 1413*b* provides a lateral cutting wire arc, extending from the open entrance of the second wire receiving slot of the first elongate body to the open entrance of the second wire receiving slot of the second elongate body. The medial and lateral cutting wire arcs can then be used to cut, by pushing the first and second elongate bodies in an alternating motion in the desired direction of cutting.

In the second embodiment, as shown in FIGS. 1, 2, 13, 14, and 19, the following applies.

There is a first wire guidance channel 408 provided in a spaced relationship with the distal end 407 and located within the first elongate body 401. The first wire guidance channel runs from an entrance 409 at the first elongate edge to an exit 410 at the second elongate edge.

Either the outer face 405 (embodiments of FIGS. 1 and 2) or the inner face 404 (embodiments of FIGS. 13 and 14) includes a first mouth portion 411 to access the first wire guidance channel 408 and a first engagement protrusion 412 adjacent to the first mouth portion for engaging with a first part of a wire loop 413 and securing this part of the wire loop within the first wire guidance channel.

There is a second wire guidance channel 428 provided in a spaced relationship with the distal end 427 and located within the second elongate body. The second wire guidance channel runs from an entrance 429 at the first elongate edge to an exit 430 at the second elongate edge.

Either the outer face 425 (embodiments of FIGS. 1 and 2) or the inner face 424 (embodiments of FIGS. 13 and 14) includes a second mouth portion 431 to access the second wire guidance channel 428 and a second engagement protrusion 432 adjacent to the second mouth portion for engaging with a second part of the wire loop 413 and securing this part of a wire loop within the second wire guidance channel.

Figure 1D:
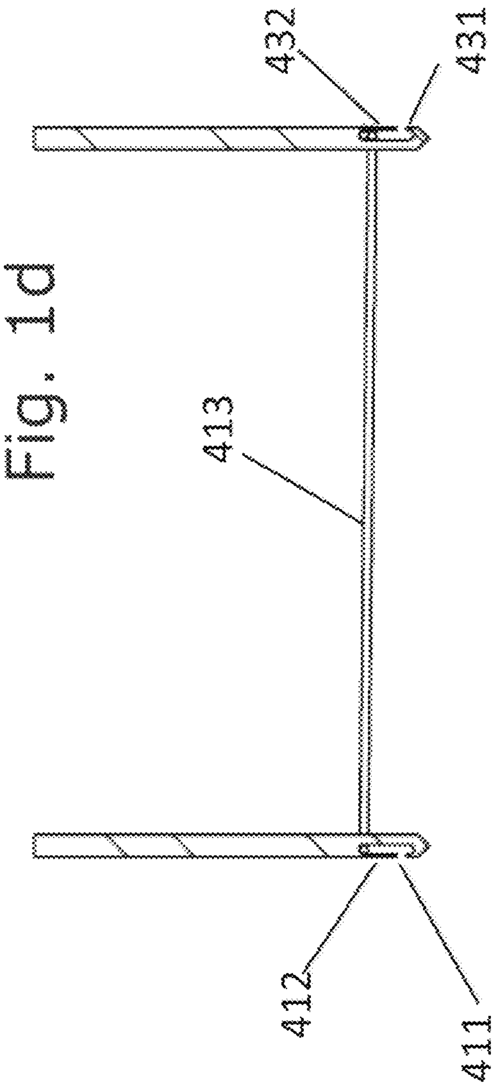
FIG. 1*d* is a cut through side view of the lower portion of the device shown in FIG. 1*a*
Figure 1C:
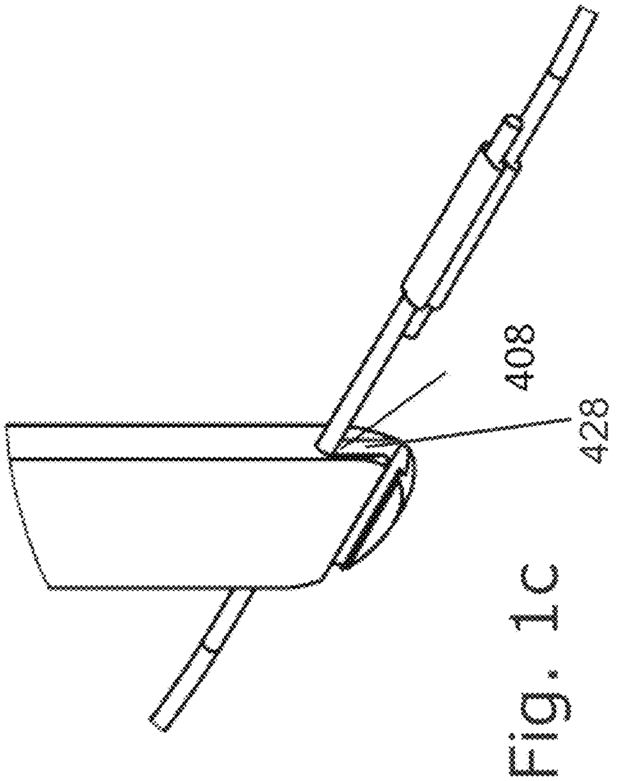
FIG. 1*c* is a close-up of the circled portion shown in FIG. 1*b*
Figures 13A, 13B:
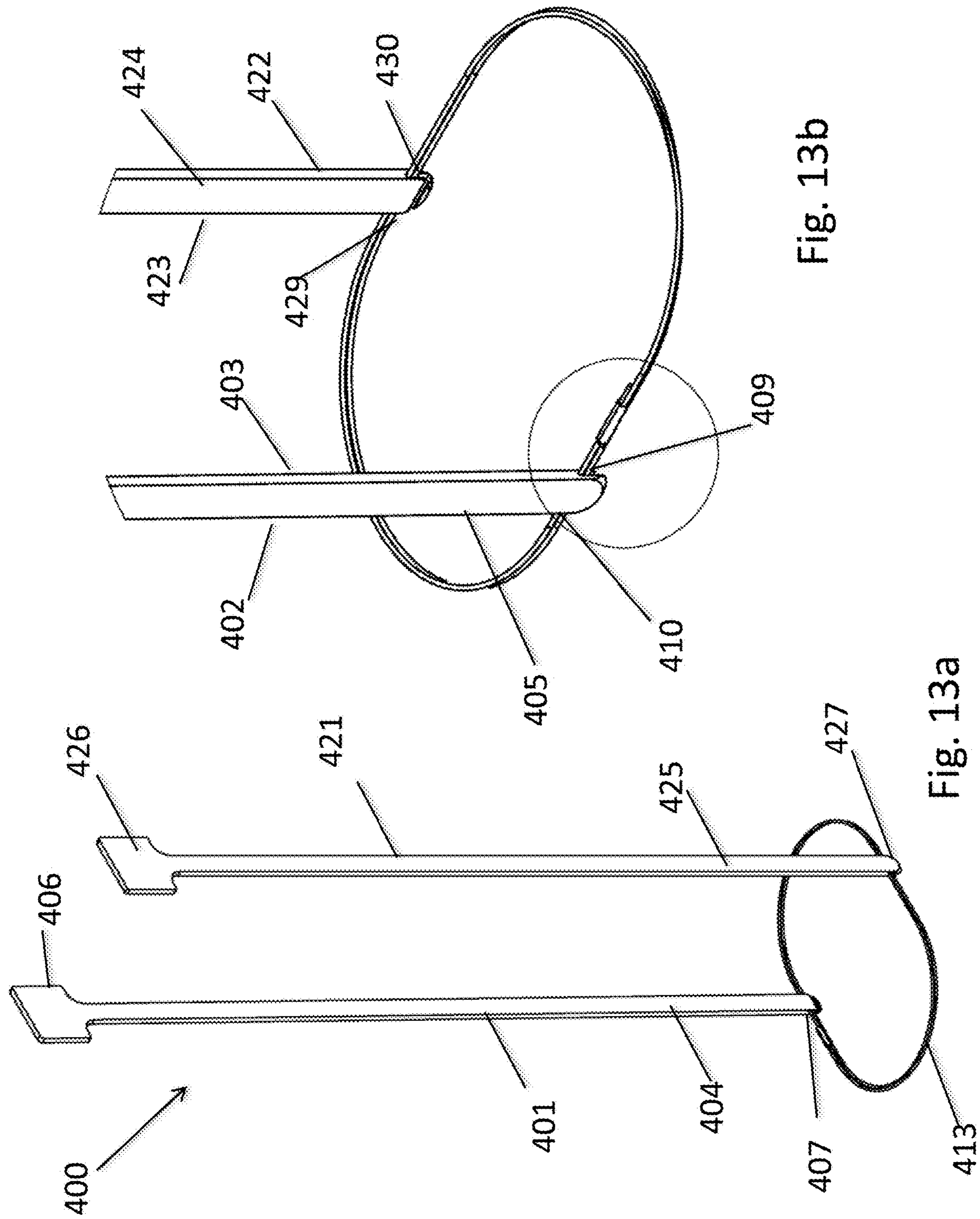
FIG. 13*a* is a perspective view of a wire delivery device of the invention
FIG. 13*b* is a close-up of the lower portion of the device shown in FIG. 13*a*
Figure 13D:
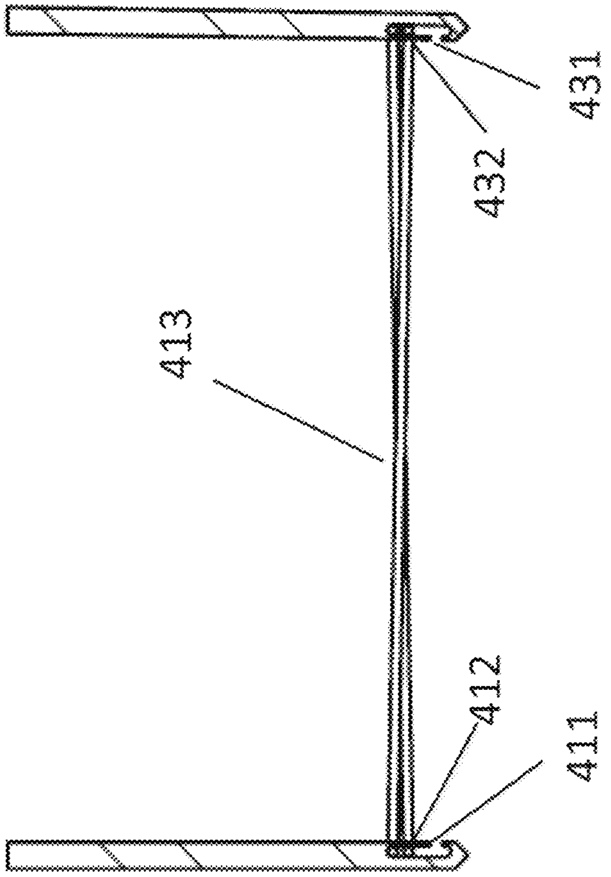
FIG. 13*d* is a cut through side view of the lower portion of the device shown in FIG. 13*a*
Figure 13C:
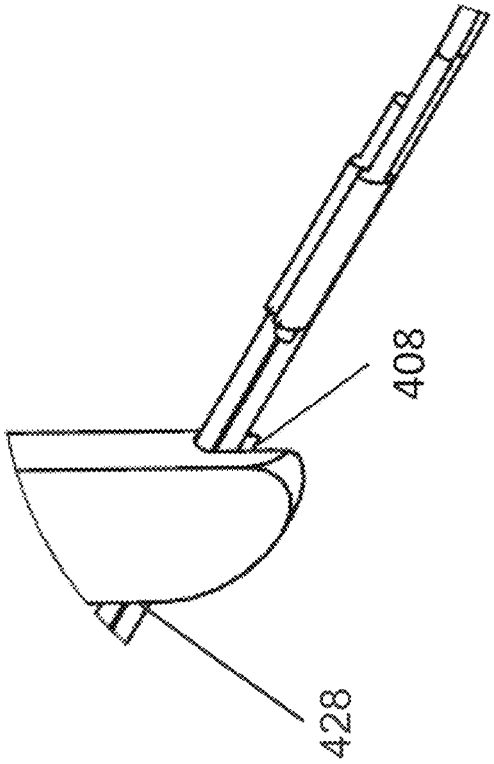
FIG. 13*c* is a close-up of the circled portion shown in FIG. 13*b*
Figure 14B:
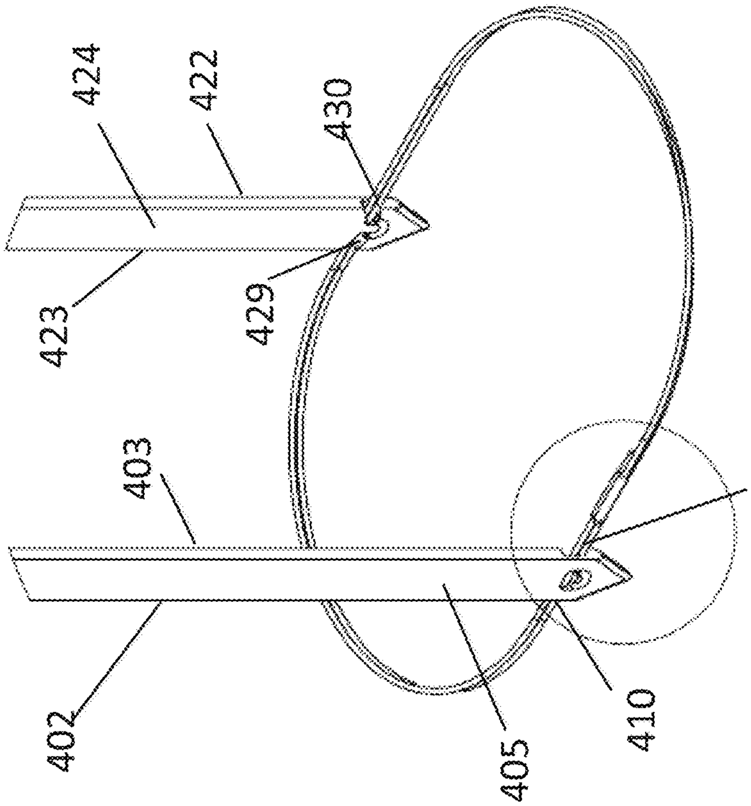
FIG. 14*b* is a close-up of the lower portion of the device shown in FIG. 14*a*
Figure 14A:
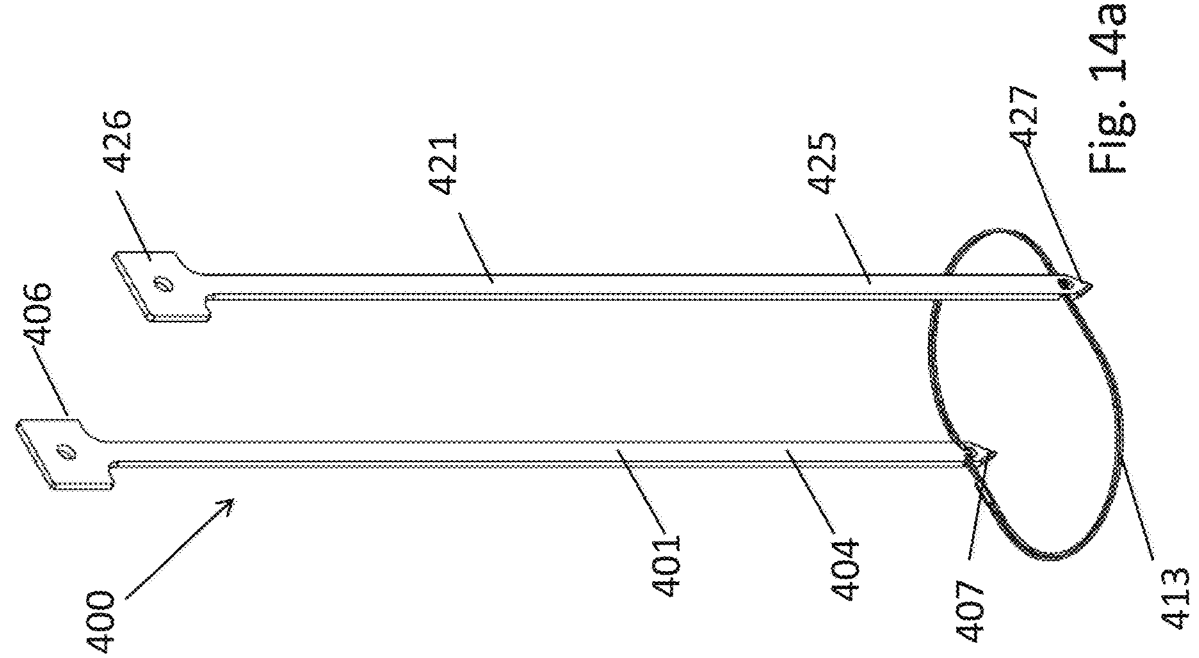
FIG. 14*a* is a perspective view of an alternative wire delivery device of the invention
Figure 14D:
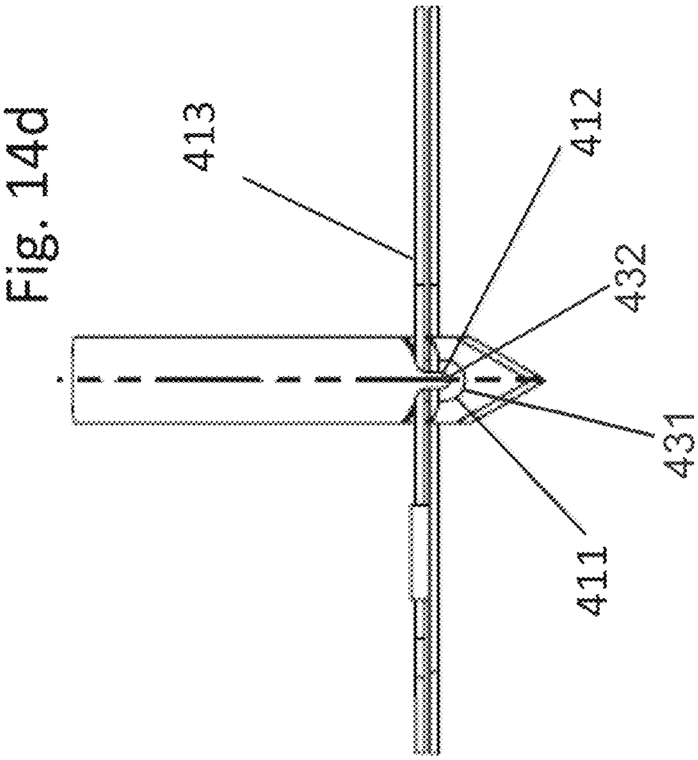
FIG. 14*d* is a face-on view of the inner face of the portion of the device shown in FIG. 14*c*
Figure 14C:
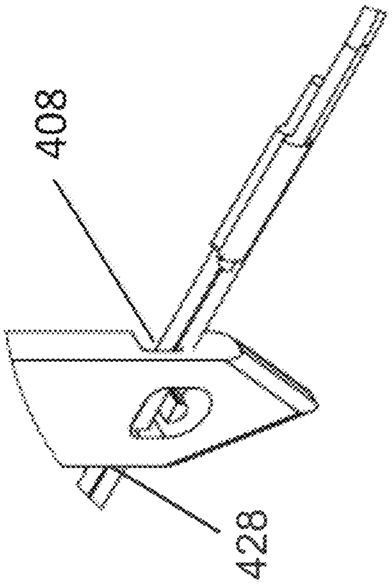
FIG. 14*c* is a close-up of the circled portion shown in FIG. 14*b*
Figure 15A:
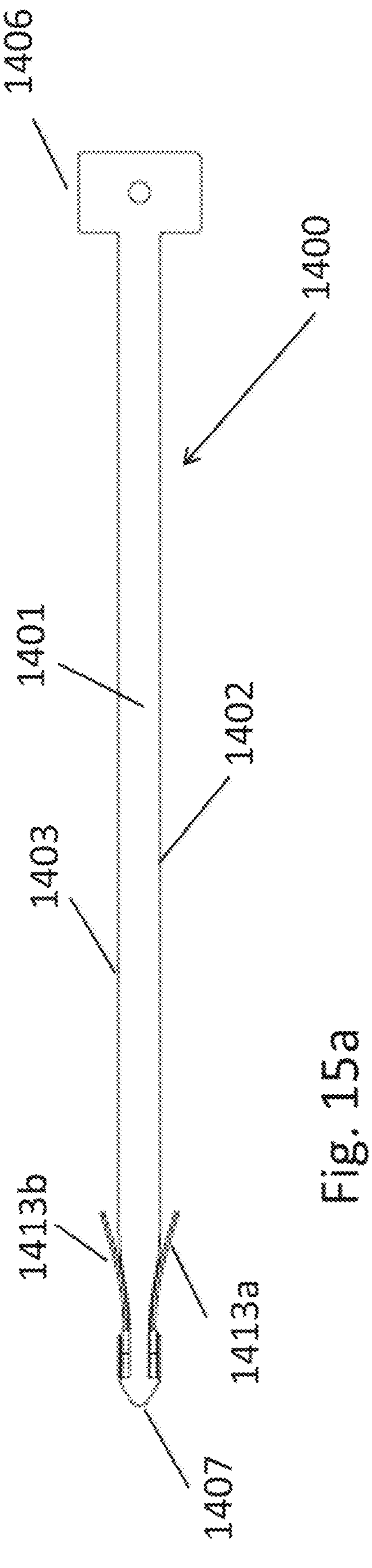
FIG. 15*a* is a plan view of an alternative wire delivery device of the invention
Figures 15B, 15C, 15D, 15E, 15F:
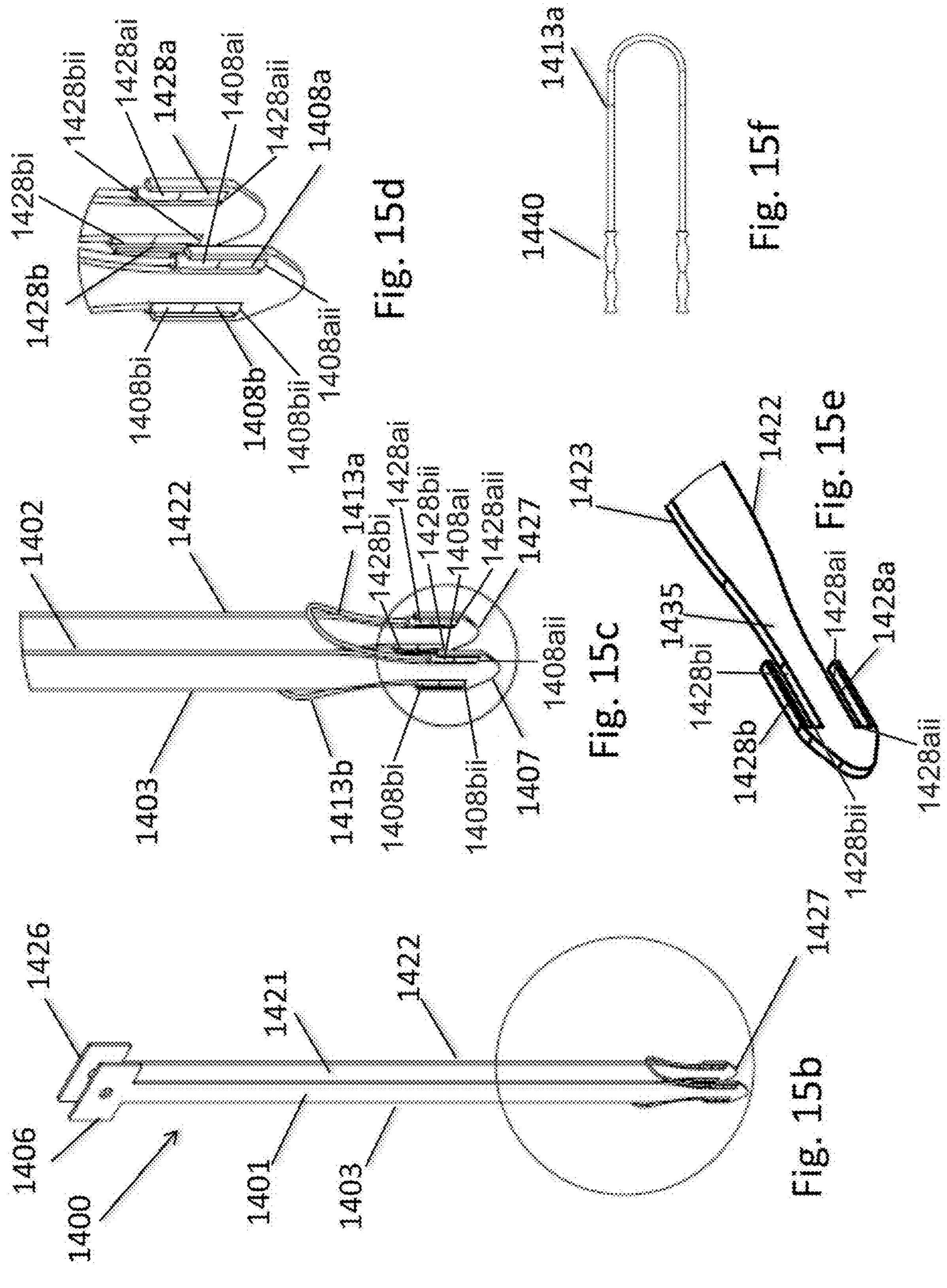
FIG. 15*b* is a perspective view of the device shown in FIG. 15*a*
FIG. 15*c* is a close-up of the lower portion of the device shown in FIG. 15*b*
FIG. 15*d* is a close-up of the circled portion shown in FIG. 15*c*
FIG. 15*e* is a close-up of the lower portion of the second elongate body of the device shown in FIGS. 15*a-d* but without the cutting wire present
FIG. 15*f* shows one of the cutting wire arcs used in the device shown in FIGS. 15*a-d*
Figure 15I:
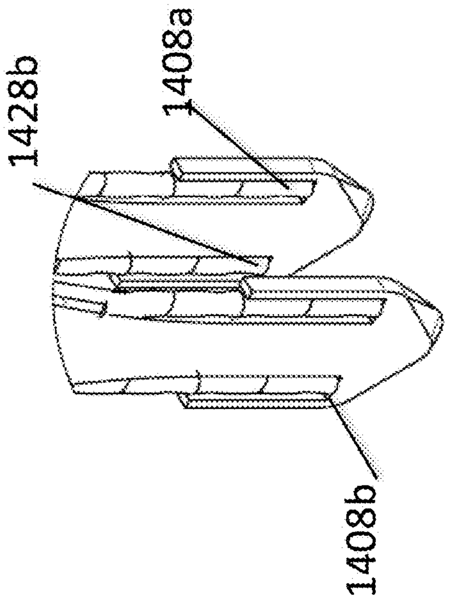
FIG. 15*i* is a close-up of the circled portion shown in FIG. 15*h*
Figure 15J:
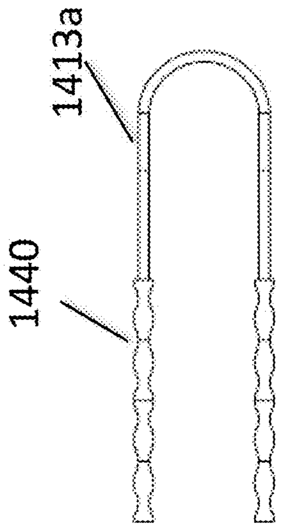
FIG. 15*j* shows one of the cutting wire arcs used in the device shown in FIGS. 15*g-i*
Figure 15H:
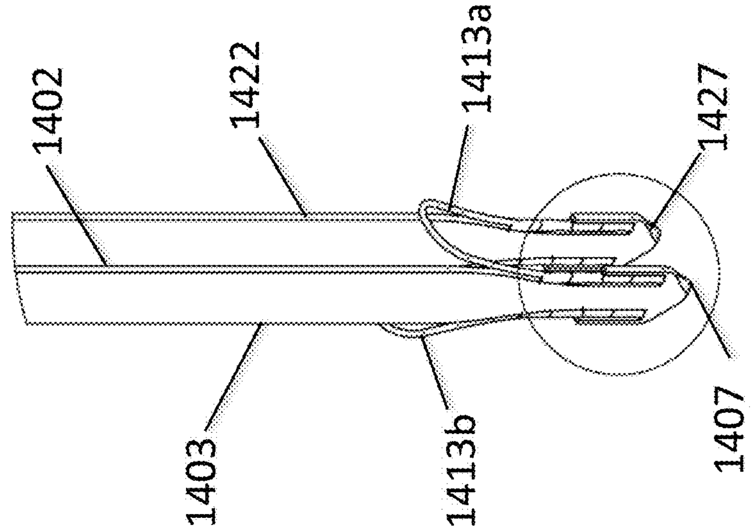
FIG. 15*h* is a close-up of the lower portion of the device shown in FIG. 15*g*
Figure 15G:
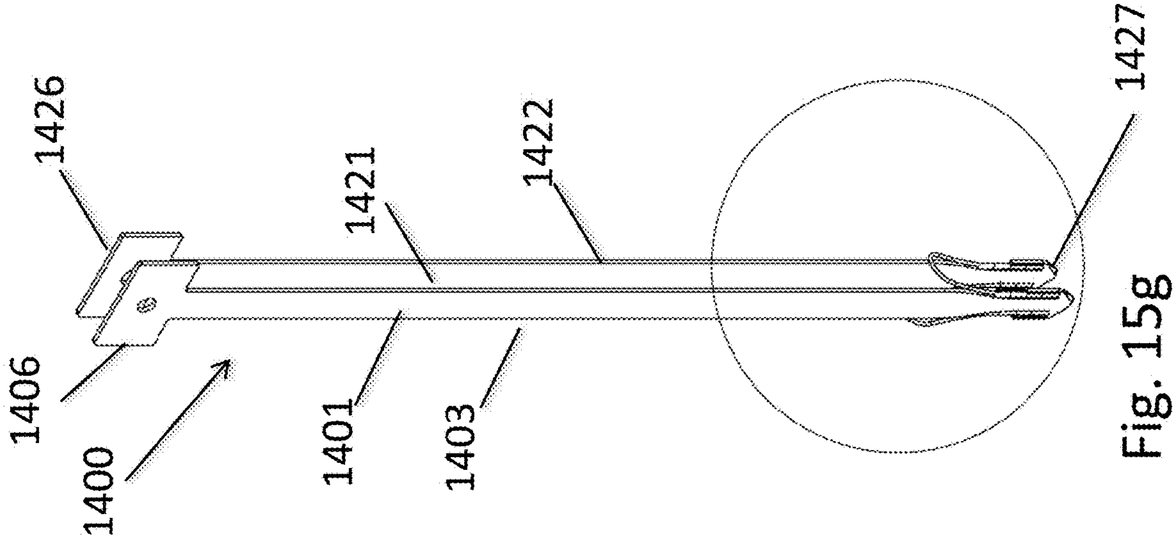
FIG. 15*g* is a perspective view of a variant on the device shown in FIGS. 15*a-d*, where there is a longer ferrule configuration and a chisel like end

The embodiment of FIGS. 1 and 13 has wire guidance channels 408, 428 that are straight and run perpendicular to the elongate axis of the elongate body. The mouth portions 411 and 431 are also straight and run substantially perpendicular to the elongate axis of the elongate body. Each mouth portion is rectangular in shape. Each corresponding engagement protrusion 412 and 432 is rectangular in shape and can be considered as a rectangular overhang. This extends across the full width of the elongate body.

Figures 2A, 2B:
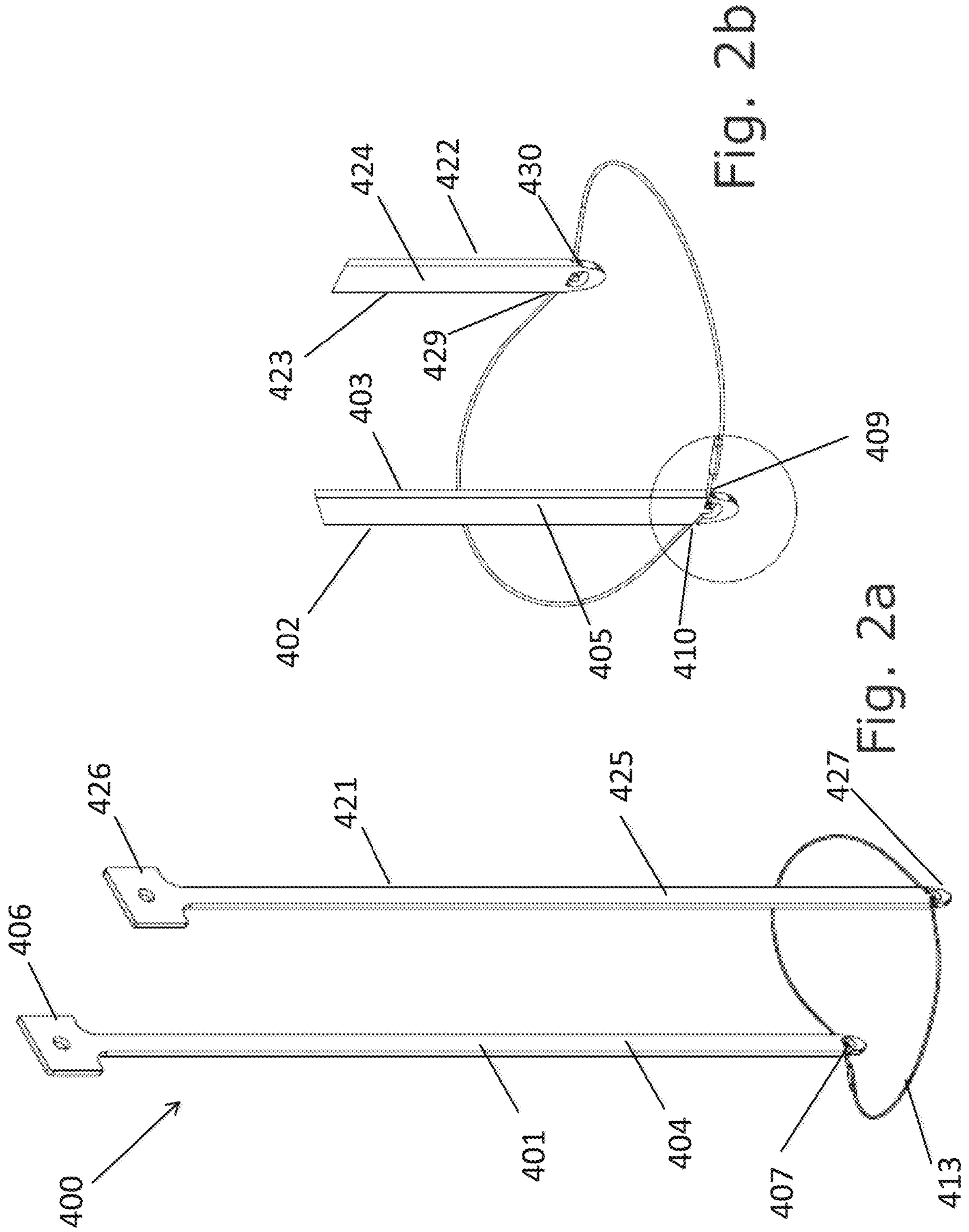
FIG. 2*a* is a perspective view of an alternative wire delivery device of the invention
FIG. 2*b* is a close-up of the lower portion of the device shown in FIG. 2*a*
Figure 2D:
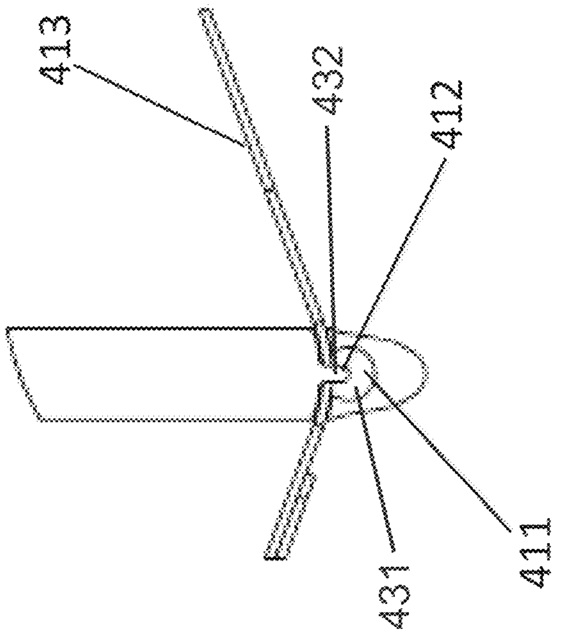
FIG. 2*d* is a face-on view of the outer face of the portion of the device shown in FIG. 2*c*
Figure 2C:
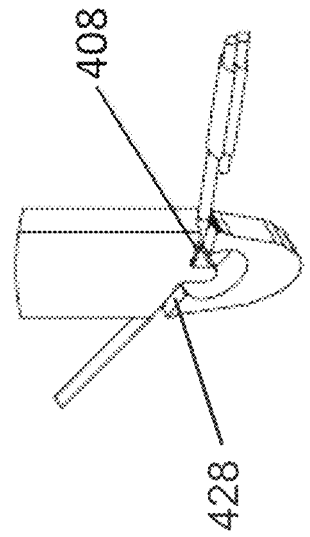
FIG. 2*c* is a close-up of the circled portion shown in FIG. 2*b*

The embodiment of FIGS. 2 and 14 has wire guidance channels 408, 428 that have a central curved portion and an angled portion on each side of the central curved portion. The mouth portions 411 and 431 each include a substantially central "U" shape and an angled portion on each side. Each corresponding engagement protrusion 412 and 432 is a tongue shaped overhang located substantially centrally between the first elongate edge and the second elongate edge.

In all the embodiments shown in FIGS. 1, 2, 13 and 14, the first part of the wire loop 413 can be fed into the first wire guidance channel via the first mouth portion and secured therein by engagement with the first engagement protrusion and the second part of the wire loop 413 can be fed into the second wire guidance channel via the second mouth portion and secured therein by engagement with the second engagement protrusion. The elongate bodies can be positioned in a spaced apart and opposite but aligned configuration, so that the wire loop provides a medial cutting wire arc from the exit of the first wire guidance channel to the entrance of the second wire guidance channel and provides a lateral cutting wire arc from the exit of the second wire guidance channel to the entrance of the first wire guidance channel. The wire loop can then be used to cut by pushing the first and second elongate bodies in an alternating motion in the desired direction of cutting.

Figure 19:
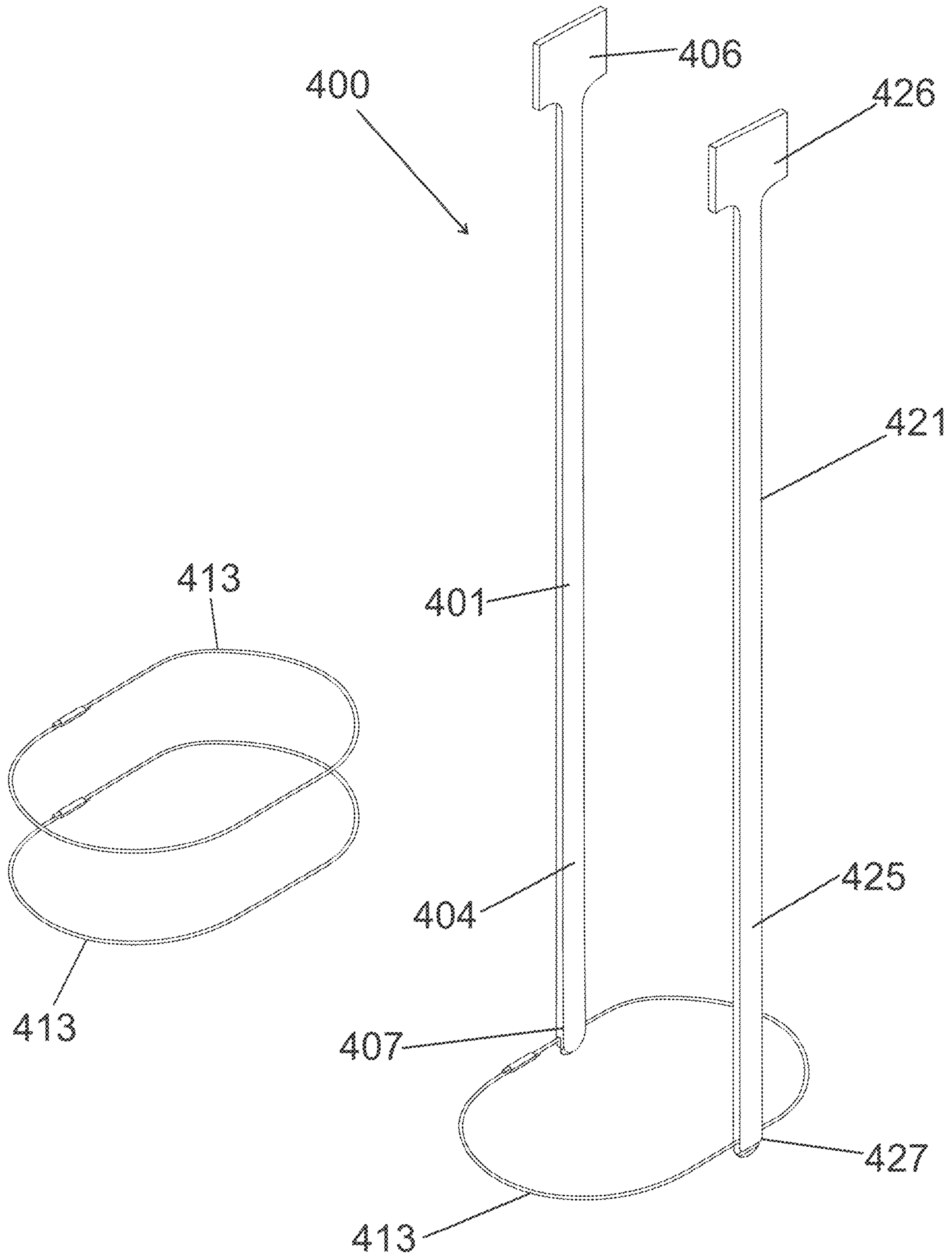
FIG. 19 is a perspective view of a wire delivery device of the invention in the form of a kit including three wire loops.

FIG. 19 depicts the wire delivery device 400 in the form of a kit including three wire loops 413.

Figure 3B:
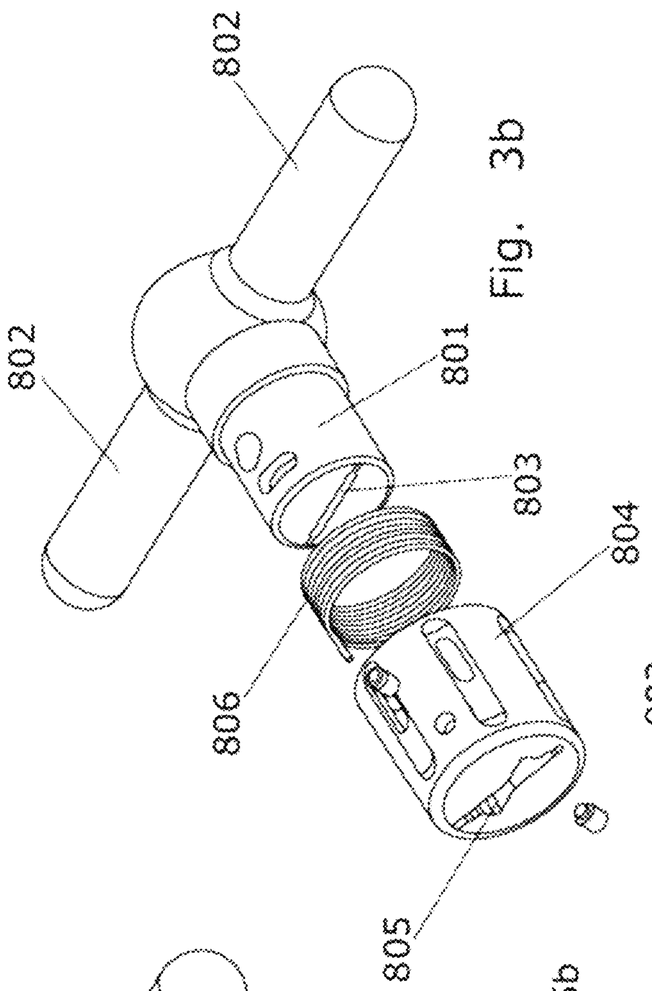
FIG. 3*b* is an exploded perspective view of a universal handle that can be used in the invention
Figure 3A:
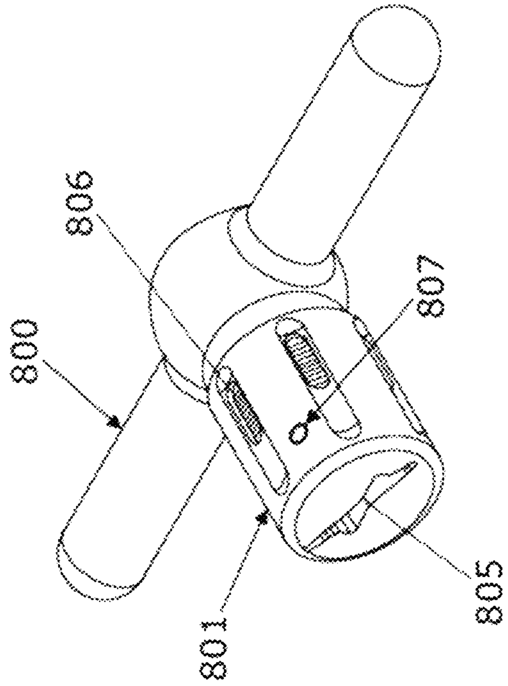
FIG. 3*a* is a perspective view of a universal handle that can be used in the invention
Figure 3C:
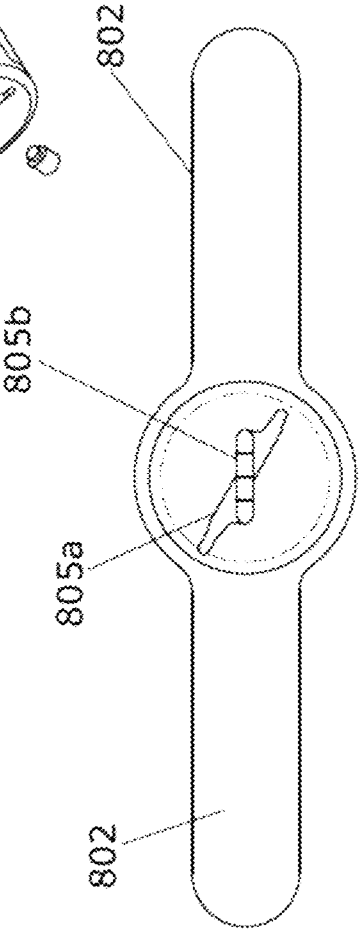
FIG. 3*c* is a top view of a universal handle that can be used in the invention

The universal handle 800 that can be used in the invention is shown in FIG. 3. The universal handle 800 can be used as a handle for two or more of the devices described above, except for the targeting device which it will be appreciated does not require a handle. The universal handle 800 comprises a body 801 having two grip portions 802 at its proximal end and an engagement recess 803 in the form of a slot, at its distal end. The engagement recess is sized and shaped to receive the proximal end (handle) of the devices described above, except for the targeting device. As shown in the drawings, the handle of the devices described above comprises a neck and an enlarged head.

The universal handle 800 is provided with a locking cap 804 which fits over the distal end of the body 801 and permits the enlarged head of the handle to be locked in place in the engagement recess 803. The locking cap 804 is provided with a dual slot 805, comprising a first elongate shaped slot 805*a* that can receive the enlarged head and allow it to pass therethrough, and a second elongate shaped slot 805*b* that can receive the neck and allow it to pass therethrough but that is too small to allow the enlarged head to pass therethrough. The first elongate shaped slot and the second elongate shaped slot overlap, with the elongate axis of the first elongate shaped slot being at an angle to the elongate axis of the second elongate shaped slot. Therefore the locking cap 804 can be placed over the distal end of the body with the first elongate shaped slot 805*a* aligned with the engagement recess and the enlarged head can pass through the first elongate shaped slot and into the engagement recess. Then the locking cap can be rotated such that the second elongate shaped slot 805*b* is aligned with the engagement recess, meaning that the enlarged head is locked into the engagement recess because it is too big to pass through the second elongate shaped slot. When it is desired to release the universal handle from the device, the locking cap can be rotated until the first elongate shaped slot is aligned with the engagement recess again.

The locking cap is spring loaded to assist with release. Therefore a torsion spring 806 is provided between the body 801 and the locking cap 804, which biases the locking cap away from the body.

The user can overcome that biasing force by pushing the locking cap onto the body. The locking cap can be held in place by the use of a securing means 807 (e.g. a locking pin and corresponding aperture) that connects the locking cap and the body.

The curette device that can be used in the invention is shown in FIG. 4.

The curette device of the invention comprises an elongate body 200 in the form of a flat plate that extends from a first elongate edge 201 to a second elongate edge 202 and having a proximal end 203 that can be provided with a handle 203*a* and having a distal end 204 that is blunt. The handle 203*a* can be understood to have an enlarged head portion extending from a neck.

The curette device of the invention also comprises a first cutting portion 205 located at or near the distal end 204. This extends outwardly from the first elongate edge 201 of the elongate body. The cutting portion has a blunt edge 206 and a cutting edge 207 which meet at an angled cutting point 208. The blunt edge extends from a first location on the elongate body to the cutting point and the cutting edge extends from a second location on the elongate body to the cutting point, wherein the first location is closer to the distal end than the second location. Furthermore, the cutting edge is at an angle to the elongate axis of the curette device of from 50 to 85 degrees.

The curette device further comprises a second cutting portion 209, located between the second elongate edge 202 and the distal end 204 of the elongate body. In the embodiment illustrated, the second cutting portion 209 is provided on a curved edge that extends between the second elongate edge 202 and the distal end 204 of the elongate body. The second cutting portion is shown as comprising teeth, but alternatively or additionally, the second cutting portion may comprise a sharp edge.

Thus the curette device can be located in an access tunnel, with its elongate axis substantially aligned with the central axis running along the length of the tunnel, and with the distal end located at or near the distal (closed) end of the access tunnel, and then can be moved such that its elongate axis is angled with respect to the central axis running along the length of the tunnel, until the cutting edge contacts bony ingrowth located between the implant and the femoral cortex, and such that the curette device can then be withdrawn from the access tunnel whilst being retained in an angled position, such that as the device is withdrawn the cutting edge cuts away bony ingrowth located between the implant and the femoral cortex.

Figures 4A, 4B, 4C, 4D:
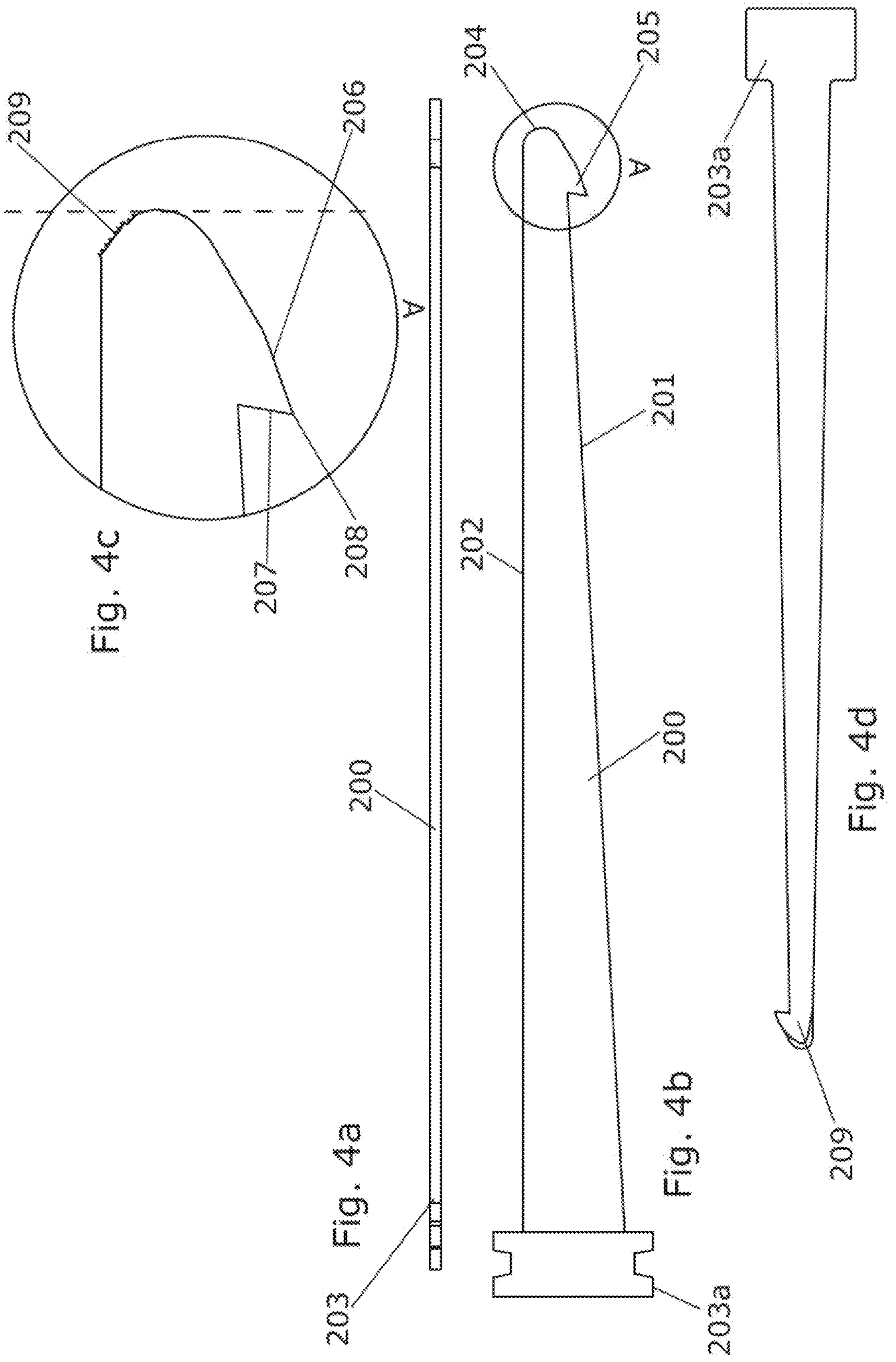
FIG. 4*a* is a side view of a curette device that can be used in the invention
FIG. 4*b* is a plan view of a curette device that can be used in the invention
FIG. 4*c* is a detailed view of the curette device shown in FIG. 4*b*
FIG. 4*d* is a plan view of an alternative curette device that can be used in the invention

FIG. 4*d* shows a different shape for the handle 203*a*. In this shape there are no indents in the side edges of the handle, as compared to the handle shape shown in FIG. 4*b*. The handle 203*a* is essentially a square or rectangular protrusion from the elongate body 200. It can be understood to have an enlarged head portion extending from a neck.

In the embodiment of FIG. 4*d* the second cutting portion 209 is shown as comprising a sharp edge. The end may be chisel like, e.g. with a 45 degree angled sharp end. This compares with the embodiment of FIG. 4*b* where the second cutting portion 209 is shown as comprising teeth.

FIG. 5 shows a chevron chisel that can be used in the invention. The chevron chisel comprises an elongate body 950 in the form of a flat plate having an upper face 950*a* and a lower face 950*b*. The elongate body 950 extends from a first elongate edge 951 to a second elongate edge 952.

The elongate body 950 has a proximal end 953 that can be provided with a handle 954. The handle 954 can be understood to have an enlarged head portion extending from a neck.

The elongate body 950 has a distal end 955. A cutting portion is located at the distal end 955. The cutting portion comprises a first cutting face 956 and a second cutting face 957 which meet at an angled cutting point 958. The angled cutting point is located substantially centrally between the first elongate edge and the second elongate edge.

The first cutting face 956 extends at an angle of about 30 or about 45 degrees or about 60 degrees from the first elongate edge 951 when measured with respect to the elongate axis of the elongate body, and the second cutting face 957 extends at an angle of about 30 or about 45 degrees or about 60 degrees from the second elongate edge 952 when measured with respect to the elongate axis of the elongate body. In addition, the first cutting face 956 extends at an angle of about 30 or about 45 degrees or about 60 degrees from the lower face to the upper face, and the second cutting face 957 extends at an angle of about 30 or about 45 degrees or about 60 degrees from the lower face to the upper face.

The chevron chisel may optionally have a depth (the lower face to the upper face) of from 0.5 to 3 mm, e.g. 1 to 2 mm; it may be about 1 mm deep. The chevron chisel may optionally have a width (first elongate edge to a second elongate edge) of from 4 to 10 mm, e.g. 5 to 9 mm; it may be about 7 to 8 mm wide.

Embodiments of the targeting device that can be used in the invention are shown in FIG. 6, FIG. 7, FIG. 8 and FIG. 9.

The targeting device comprises an anterior guide member 1. This comprises a first elongate body provided with a first angled channel 2 therein, running from an entrance 2*a* at the proximal end of the guide member to an exit 2*b* at the distal end of the guide member. The first angled channel is at an angle in the range of from 1 to 3 degrees to the elongate axis of the elongate body, ideally 2 degrees or 2.5 degrees or 3 degrees.

The first elongate body also has a first contact element in the form of a leg 3 at its distal end for contacting the shoulder of the femoral implant and for distancing the exit from the shoulder of the implant.

The targeting device also comprises a posterior guide member 4, which comprises a second elongate body provided with a second angled channel 5 therein, running from an entrance 5*a* at the proximal end of the guide member to an exit 5*b* at the distal end of the guide member. The second angled channel is at an angle in the range of from 1 to 3 degrees to the elongate axis of the elongate body, ideally 2 degrees or 2.5 degrees or 3 degrees.

The posterior elongate body also has a second contact element in the form of a leg 6 at its distal end for contacting the surface of the shoulder of the implant and for distancing the exit from the shoulder of the implant.

Figure 6A:
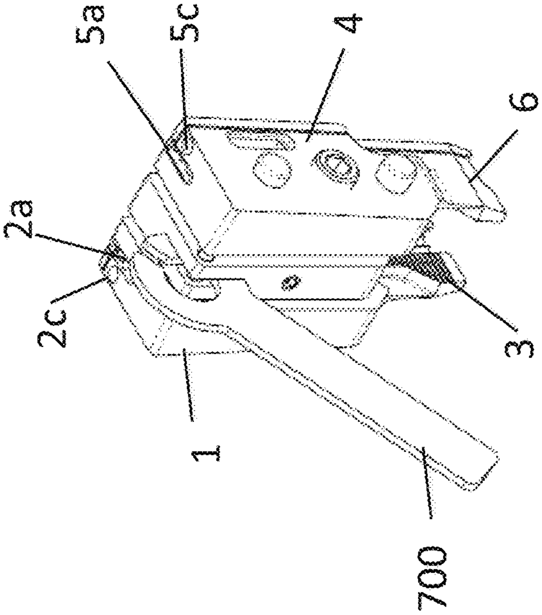
FIG. 6*a* is a perspective view of a targeting device that can be used in the invention, together with a medial targeting device
Figure 6B:
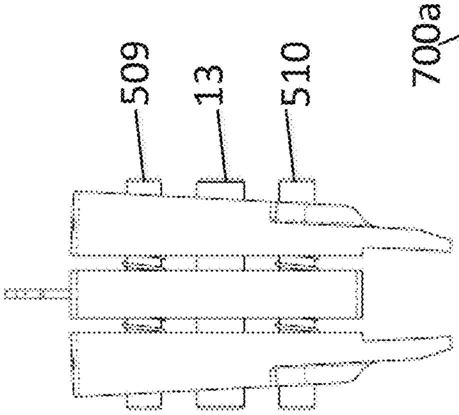
FIG. 6*b* is a side view of a targeting device that can be used in the invention
Figure 6C:
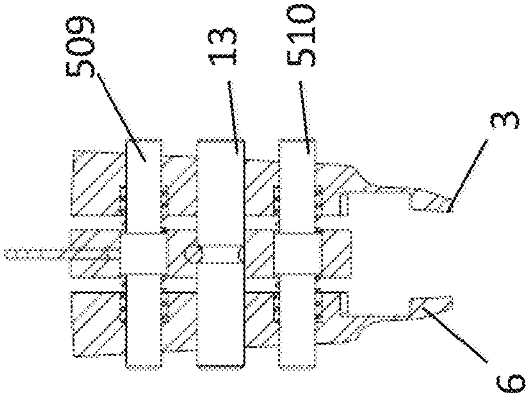
FIG. 6*c* is a cut through view of a targeting device that can be used in the invention
Figure 6D:
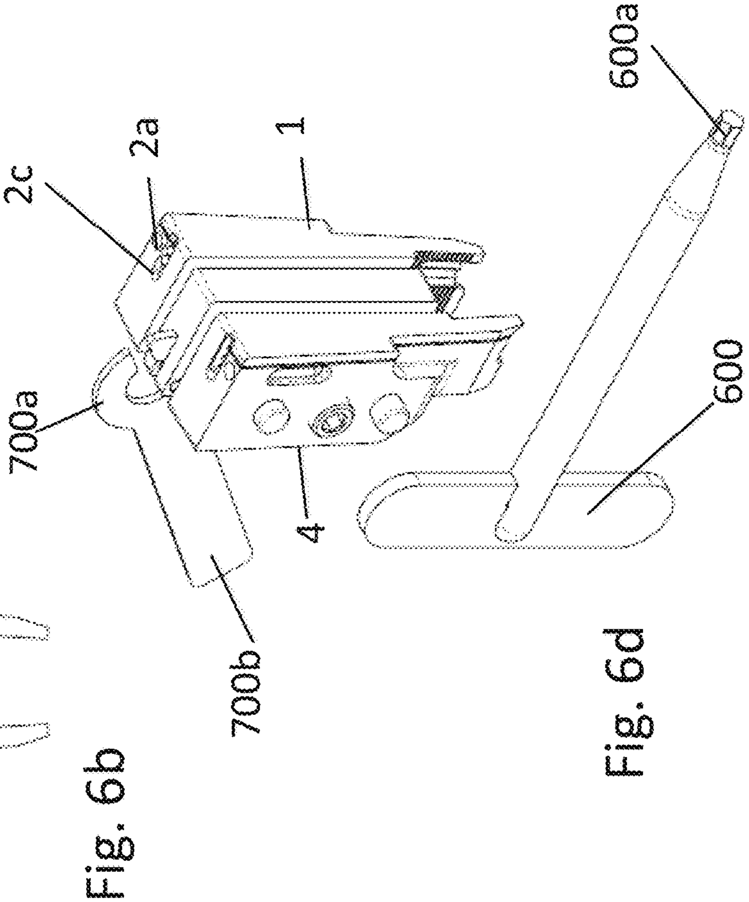
FIG. 6*d* is a perspective view of a targeting device that can be used in the invention, together with a medial targeting device and a key

In some embodiments, there is one angled channel 2 with entrance 2*a* in the anterior guide member and one angled channel 5 with entrance 5*a* in the posterior guide member. For example, the angled channels may each have a rectangular cross section. This is shown in FIGS. 6*a* and 6*d*.

Figure 9B:
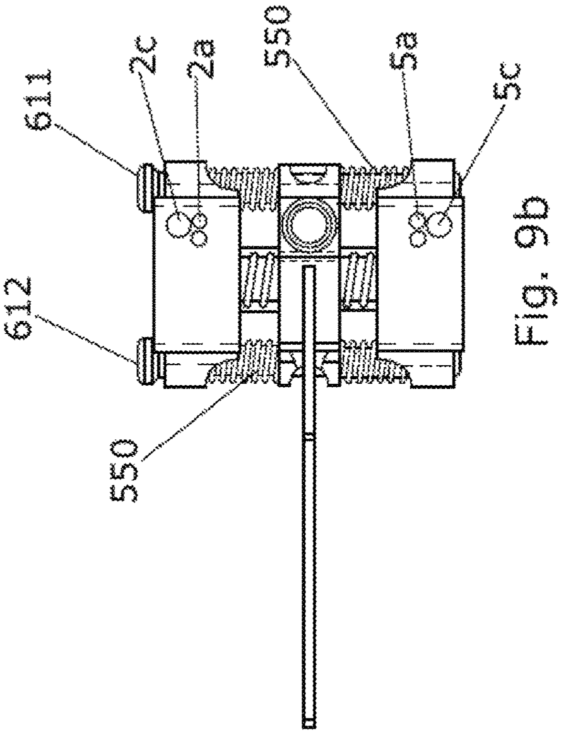
FIG. 9*b* is a top view of a targeting device that can be used in the invention, together with a medial targeting device

In some embodiments, there are two angled channels 2 with entrance 2*a* in the anterior guide member and two angled channels 5 with entrance 5*a* in the posterior guide member. For example, the angled channels may each have a circular cross section. The angled channels in the anterior guide member may be co-joined and the angled channels in the posterior guide member may be co-joined. This is shown in FIGS. 9*a* and 9*b*.

Figure 7A:
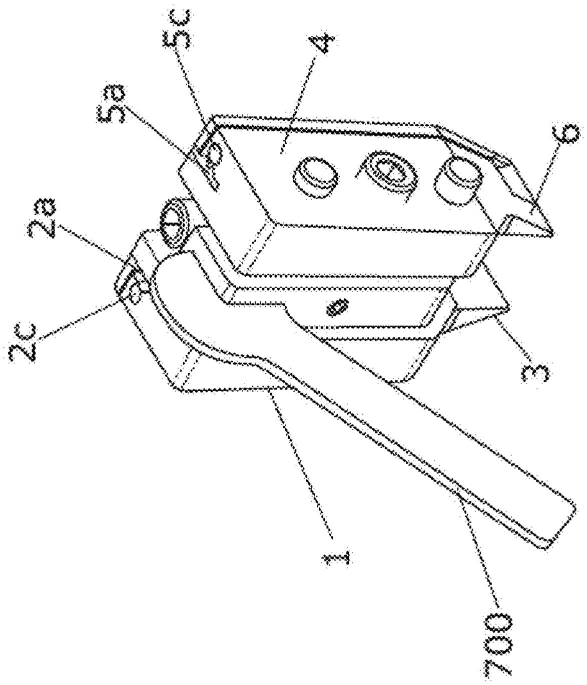
FIG. 7*a* is a perspective view of a targeting device that can be used in the invention, together with a medial targeting device
Figure 7B:
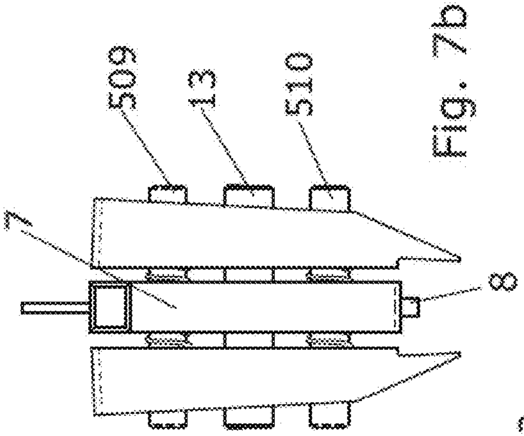
FIG. 7*b* is a side view of a targeting device that can be used in the invention
Figure 7C:
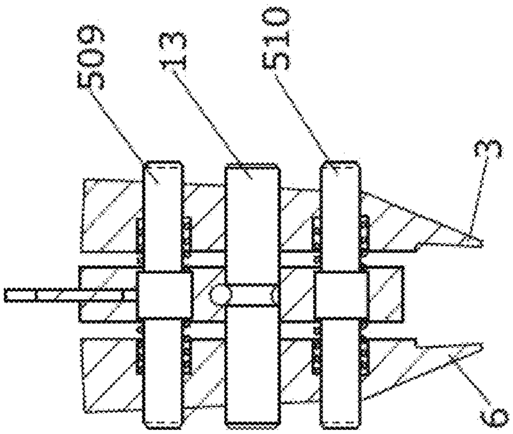
FIG. 7*c* is a cut through view of a targeting device that can be used in the invention
Figure 7D:
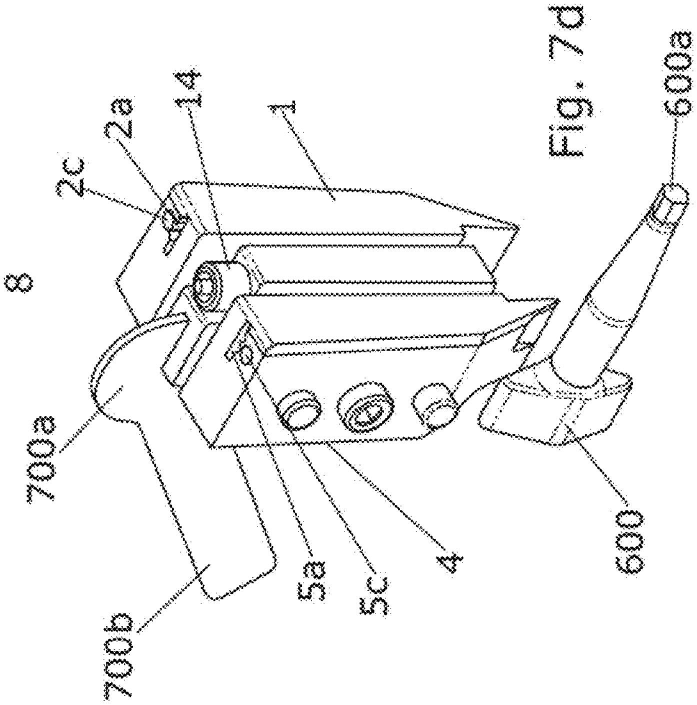
FIG. 7*d* is a perspective view of a targeting device that can be used in the invention, together with a medial targeting device and a key
Figure 8C:
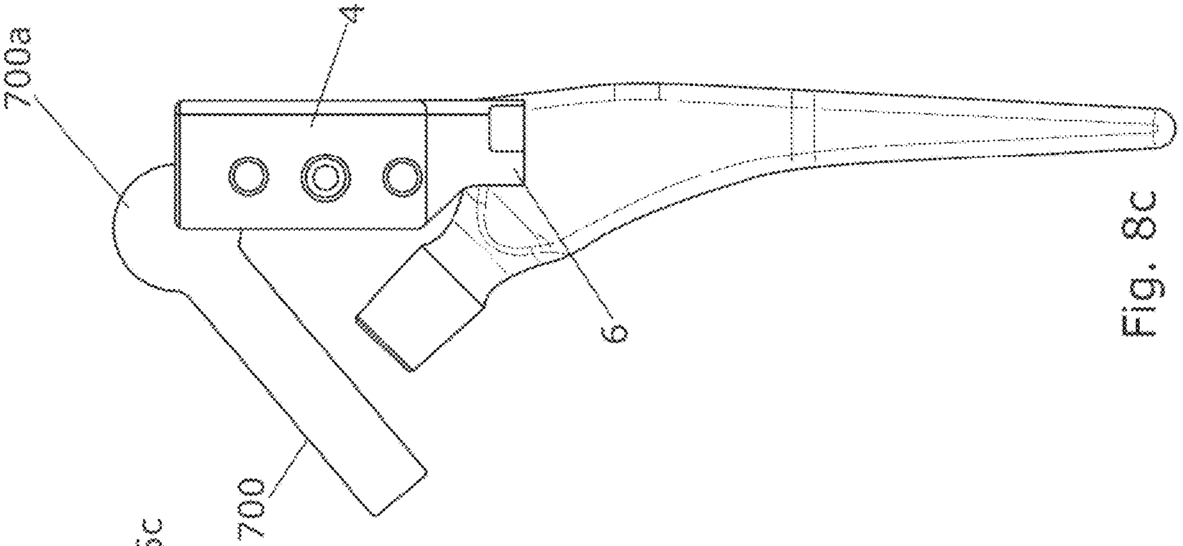
FIG. 8*c* is a front view of a targeting device that can be used in the invention, located on a femoral implant, and together with a medial targeting device
Figure 8B:
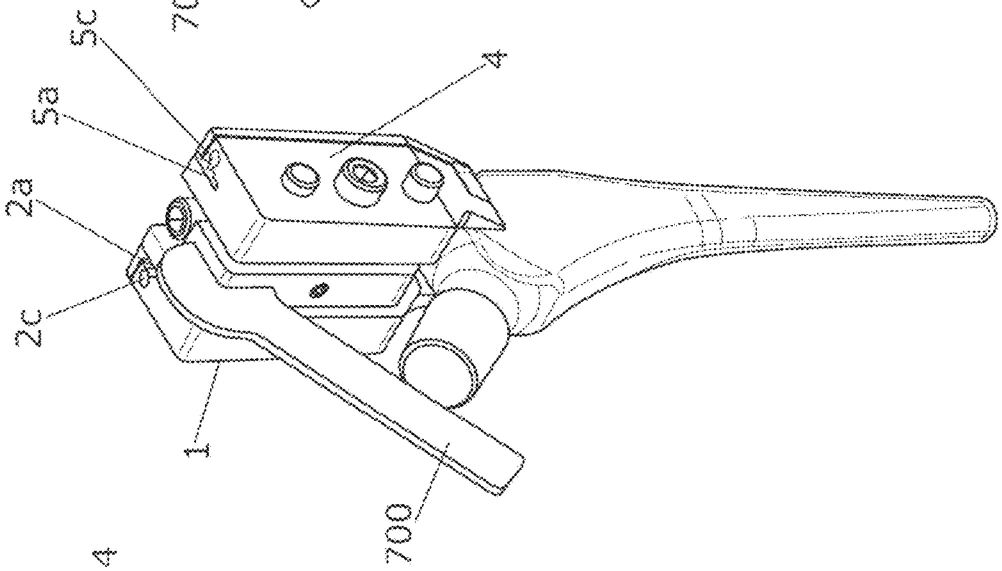
FIG. 8*b* is a perspective view of a targeting device that can be used in the invention, located on a femoral implant, and together with a medial targeting device
Figure 8A:
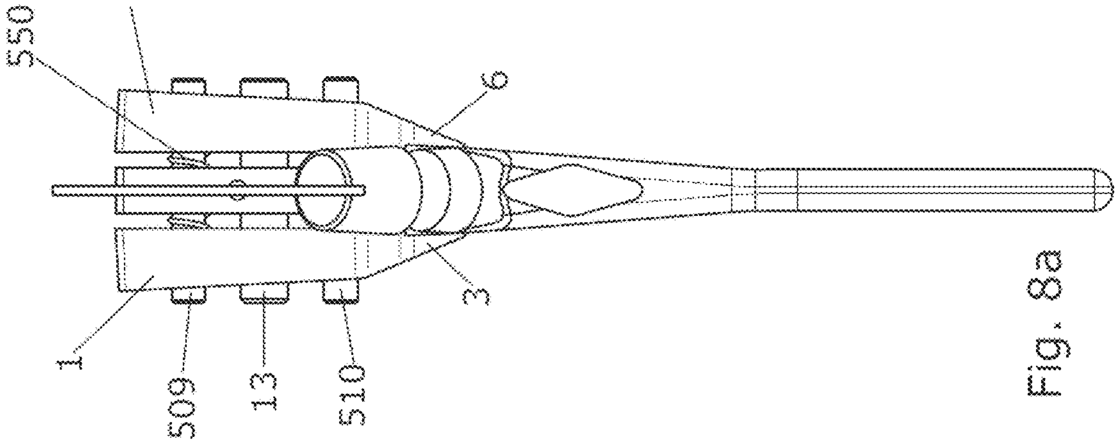
FIG. 8*a* is a side view of a targeting device that can be used in the invention, located on a femoral implant, and together with a medial targeting device

In some embodiments, there are three angled channels 2 with entrance 2*a* in the anterior guide member and three angled channels 5 with entrance 5*a* in the posterior guide member. For example, there may be one channel having a rectangular cross section and two having a circular cross section in each of the anterior guide member and the posterior guide member. The angled channels in the anterior guide member may be co-joined and the angled channels in the posterior guide member may be co-joined. This is shown in FIGS. 7*a*, 7*d* and 8*b*.

The targeting device may optionally also include receiving channels 2*c*, 5*c*, for receiving the anterior guide member interlocking component 705 and the posterior guide member interlocking component 706 of the external targeting device as shown in FIG. 10 and described below.

In this embodiment, the targeting device includes a first receiving channel 2*c* adjacent to the first angled channel 2 and aligned therewith and includes a second receiving channel 5*c* adjacent to the second angled channel 5 and aligned therewith. The anterior guide member interlocking component 705 and the posterior guide member interlocking component 706 are then received in these channels respectively. The first and second receiving channels 2*c*, 5*c* are shown as circular in cross section and these may each have a diameter of from 2 to 4 mm, such as about 3 mm. However, other shapes could be envisaged, e.g. they could have a square cross section, and likewise other sizes could be envisaged. The first and second receiving channels 2*c*, 5*c* may be blind channels and may, for example, extend for a depth of from 25 to 40 mm, such as about 30 mm.

The targeting device also comprises an engagement member 7 for locating and engaging the targeting device on the shoulder of the implant. This comprises an elongate body with an engagement protrusion 8 at its distal end. The engagement protrusion 8 can be received in a recess portion R on the shoulder of the implant. The elongate body of the engagement member can be located between and aligned with the elongate body of the anterior guide member 1 and the elongate body of the posterior guide member 4, such that the elongate axes of the elongate bodies are substantially aligned, and with the angled channels 2, 5 converging in the direction of the distal end, ideally at a convergence angle of 4 to 6 degrees, e.g. 4 degrees or 6 degrees.

The elongate body of the engagement member 7 may be substantially block-shaped. It may be that the block includes a rod 14 extending therethrough, with the distal end of the rod providing the engagement protrusion 8 (see FIGS. 7-9).

In one embodiment, the targeting device comprises a first pair of parallel connector rails 509, 510, which comprises one proximal rail 509 and one distal rail 510 (see FIGS. 6 and 7). The pair of parallel connector rails 509, 510 is located at or near the midpoint between the medial face of the guide members and the lateral face of the guide members.

The connector rails are slidably secured to the engagement member. Therefore the proximal connector rail 509 is received in proximal connection bores in the anterior guide member, in the engagement member, and in the posterior guide member, whilst the distal connector rail 510 is received in distal connection bores in the anterior guide member, in the engagement member, and in the posterior guide member (see FIGS. 6*b,c* and 7*b,c*).

In yet another embodiment, the targeting device comprises a first pair of parallel connector rails 609, 610, which comprises one proximal rail 609 and one distal rail 610, and a second pair of parallel connector rails 611, 612, which comprises one medial rail 611 and one lateral rail 612 (see FIG. 9).

The first pair of parallel connector rails 609, 610 is located at or near the midpoint between the medial face of the guide members and the lateral face of the guide members. The second pair of parallel connector rails 611, 612 is located at or near the midpoint between the proximal end of the guide members and the distal end of the guide members.

The connector rails are slidably secured to the engagement member. Therefore the proximal connector rail 609 is received in proximal connection bores in the anterior guide member, in the engagement member, and in the posterior guide member, whilst the distal connector rail 610 is received in distal connection bores in the anterior guide member, in the engagement member, and in the posterior guide member (see FIG. 9*c*). The medial connector rail 611 is received in medial connection bores provided on the anterior guide member, on the engagement member, and on the posterior guide member, whilst the lateral connector rail 612 is received in lateral connection bores provided on the anterior guide member, on the engagement member, and on the posterior guide member (see FIG. 9*a*, 9*b*).

As shown in FIGS. 6-9 each connector rail may be provided with a spring 550 around its outer circumference that serves to bias the anterior guide member 1 and the posterior guide member 4 into their release positions. The biasing force of the spring 550 can be overcome by use of the adjustment system 13 (as described further below) to move the anterior guide member and the posterior guide member into their holding positions.

The targeting device also comprises an adjustment system, which may be a double ended screw 13 that can adjust the distance between the elongate body of the anterior guide member 1 and the elongate body of the engagement member 7, so as to move the anterior guide member between a release position and a holding position and can simultaneously adjust the distance between the elongate body of the posterior guide member 4 and the elongate body of the engagement member 7, so as to move the posterior guide member between a release position and a holding position.

The double ended screw 13 can be received in a first engaging bore 13*a* in the anterior guide member, a second engaging bore 13*c* in the posterior guide member and a non-engaging bore 13*b* in the engagement member.

In the embodiment shown in FIGS. 6 and 7, this series of bores is parallel to the connection bores for the proximal rail 509 and the distal rail 510. Therefore in use the anterior guide member 1, the engagement member 7 and the posterior guide member 4 are connected and aligned using the proximal rail 509 and the distal rail 510 and the double ended screw 13, which are parallel to one another.

In the embodiment shown in FIG. 9, this series of bores is parallel to the connection bores for the proximal rail 609, the distal rail 610, the medial rail 611 and the lateral rail 612. Therefore in use the anterior guide member 1, the engagement member 7 and posterior guide member 4 are connected and aligned using the proximal rail 609, the distal rail 610, the medial rail 611 and the lateral rail 612, and the double ended screw 13.

The double ended screw 13 does not engage with the non-engaging bore 13*b* in the engagement member. The non-threaded section in the middle of the double ended screw will be located in the non-engaging bore. Therefore the double ended screw extends through the engagement member but is not attached to the engagement member.

The double ended screw 13 does engage with the engaging bore 13*a* in the posterior guide member and does engage with the engaging bore 13*c* in the anterior guide member. The threaded portions at the two ends of the double ended screw are received in and engage with these engaging bores 13*a*, 13*c*. Therefore in use the double ended screw is attached to the anterior guide member and to the posterior guide member.

A key 600 may be provided that has a distal end 600*a* which engages with and rotates the double ended screw 13 (see FIGS. 6*d*, 7*d* and 9*a*).

The use of a double ended screw means that the anterior guide member 1 and the posterior guide member 4 can be simultaneously moved closer to or away from the engagement member 7 by the same distance.

Therefore when the anterior guide member and the posterior guide member are connected by the connector rails, via the engagement member, the elongate axes of the elongate bodies are substantially aligned and the angled channels converge in the direction of the distal end, such that the engagement protrusion can be located in a recess portion on the shoulder of the implant, with the anterior guide member and the posterior guide member in their release positions, and then the adjustment member can be used to move the anterior guide member towards its holding position until the first contact element contacts the surface of the shoulder of the implant, with the exit of the first angled channel lying spaced from the implant, and to simultaneously move the posterior guide member towards its holding position until the second contact element contacts the surface of the shoulder of the implant, with the exit of the second angled channel lying spaced from the implant.

The angled channel in the anterior guide member may be an integral part of the guide member. In other words, the angled channel is fixed within the anterior guide member. Likewise, the angled channel in the posterior guide member may be an integral part of the guide member. In other words, the angled channel is fixed within the posterior guide member.

The targeting device may be used in combination with a medial targeting device 700, as shown in FIGS. 6, 7 and 8. This device can be used to double check the alignment of the targeting kit in the antero-posterior plane before the tunnels are drilled.

Figure 9D:
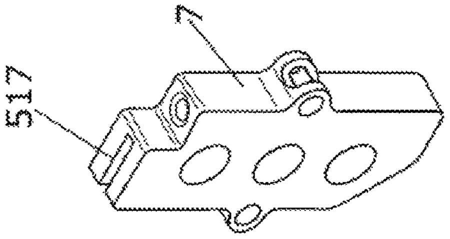
FIG. 9*d* is a perspective view of the engagement member of a targeting device that can be used in the invention
Figure 9C:
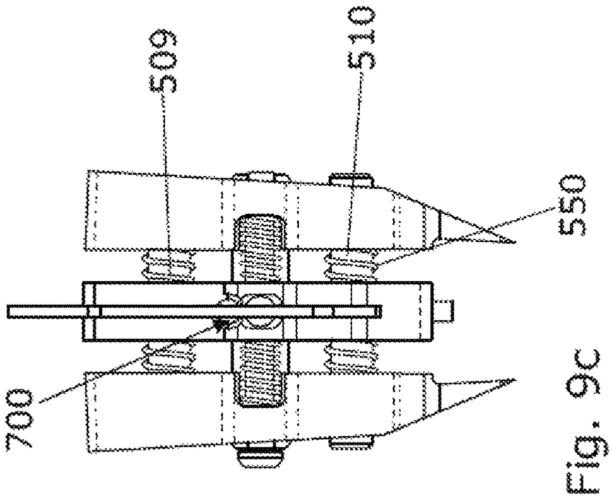
FIG. 9*c* is a side view of a targeting device that can be used in the invention
Figure 9A:
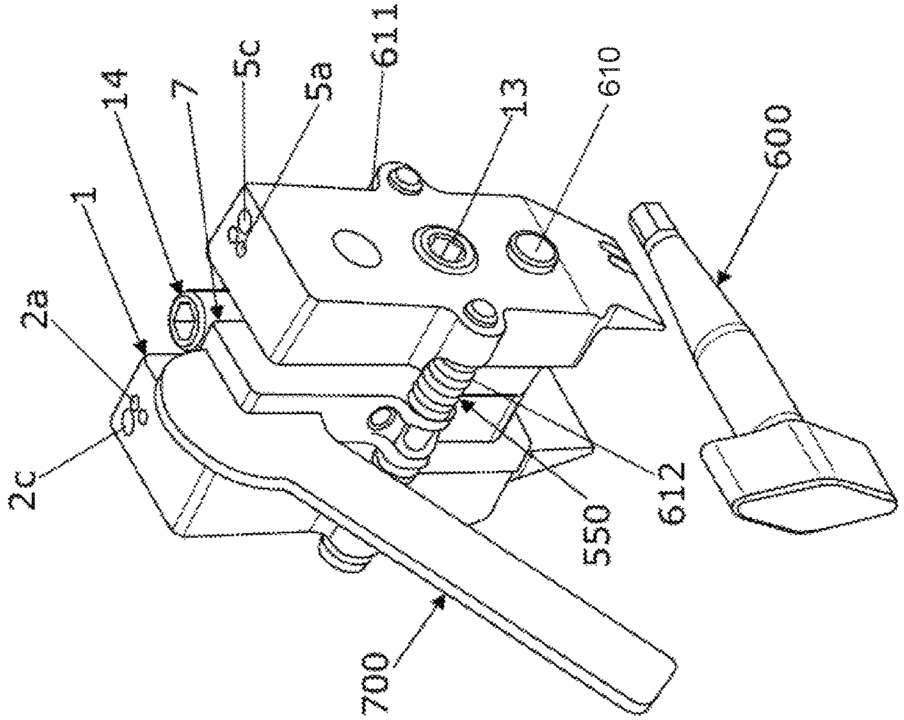
FIG. 9*a* is a perspective view of a targeting device that can be used in the invention, together with a medial targeting device and a key

When a medial targeting device 700 is used, the targeting device is provided with an alignment slot 517 located at the proximal end of the engagement member 7 (See FIG. 9*d*). This alignment slot is in longitudinal alignment with the engagement protrusion 8 of the engagement member 7.

The medial targeting device 700 is in the form of a plate, which has an enlarged head 700*a* at the proximal end and an elongate body 700*b* that extends to the distal end. The enlarged head 700*a* is circular and is sized and shaped to be received in the alignment slot 517 of the engagement member 7 (see FIGS. 6*a*, 6*d*, 7*a*, 7*d*). The elongate body 700*b* has a length greater than the distance from the alignment slot 517 to the engagement protrusion of the engagement member.

In use (see FIGS. 8*a*, 8*b*, 8*c*), the enlarged head 700*a* is received in the alignment slot 517 of the engagement member and the elongate body 700*b* of the medial targeting device is then pivoted until it contacts the proximal end of the neck 120 of the femoral implant. An assessment can be made as to whether the elongate plate is bisecting the neck centrally in the antero-posterior plane. If it is not, the location of the targeting device can be adjusted until the elongate plate of the medial targeting device does bisect the neck centrally in the antero-posterior plane.

Figure 8F:
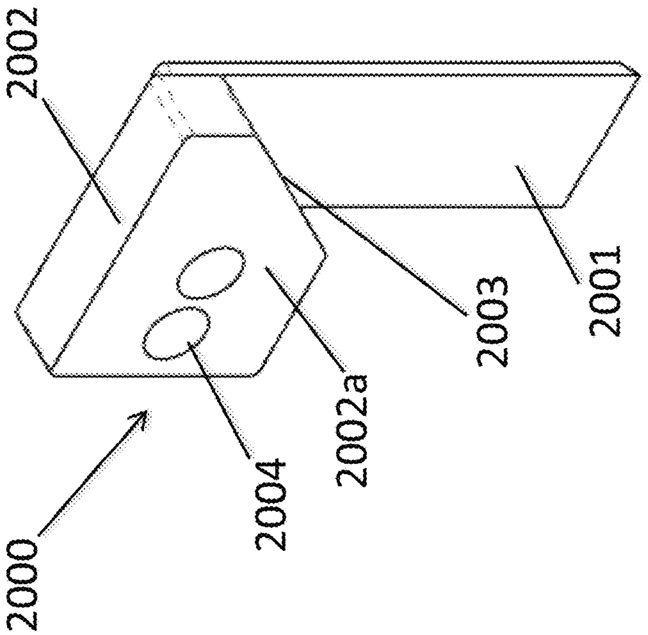
FIG. 8*f* is a perspective view of a side extender device as used in FIGS. 8*d* and 8*c*
Figure 8E:
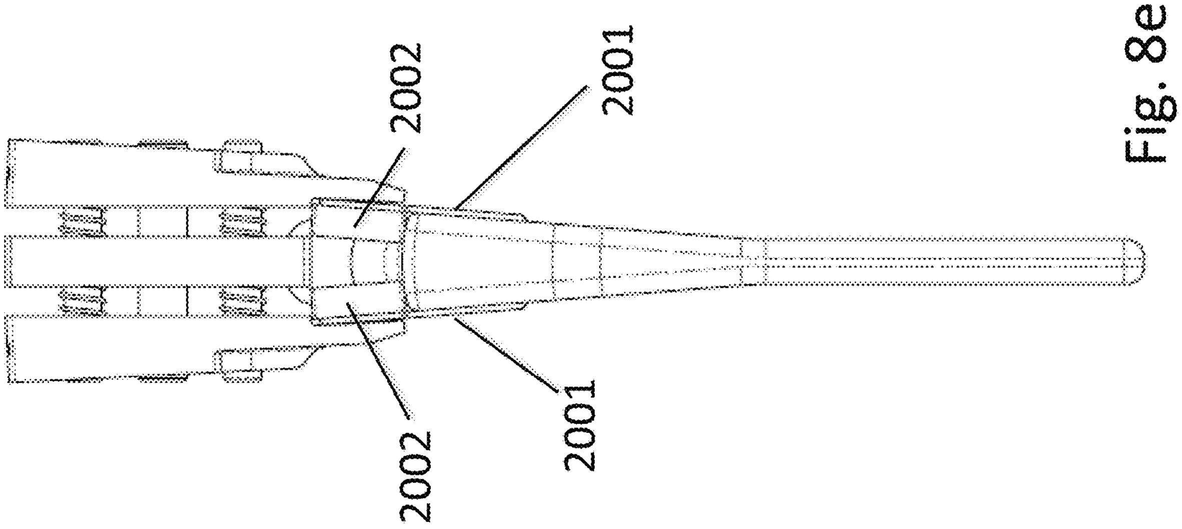
FIG. 8*e* is a side view of the targeting device and side extender devices as shown in FIG. 8*d*
Figure 8D:
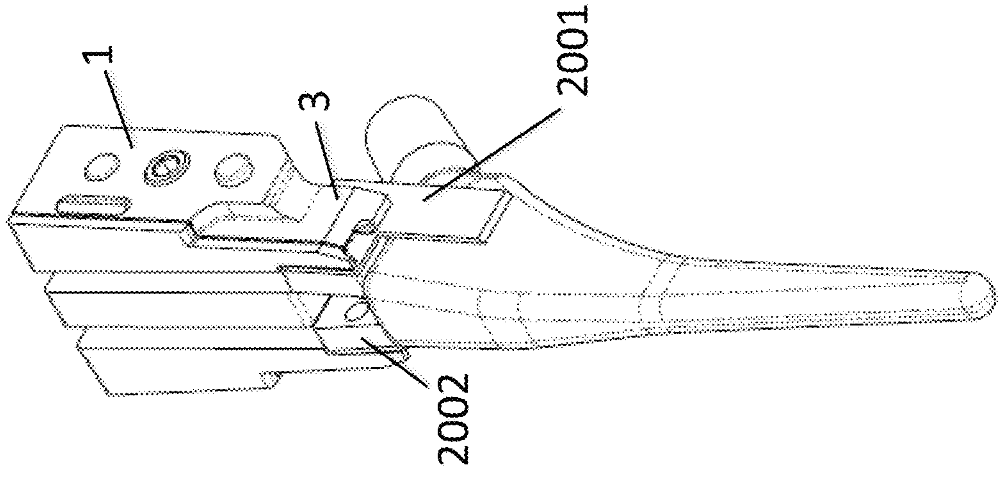
FIG. 8*d* is a perspective view of a targeting device that can be used in the invention, located on a femoral implant, and mounted using a right-handed side extender device and left-handed side extender device

FIGS. 8*d*, 8*e* and 8*f* show how side extension devices 2000 can be used in situations where the femoral implant has sunk significantly distally in relation to the femur.

The side extension device 2000 can be formed from a side plate 2001 (e.g., 1 mm thick 420 hardened stainless steel) which is welded to a block 2002 (e.g., 5 mm thick 420 hardened stainless steel). The side plate 2001 suitably extends 20 mm beyond the welded block 2002.

The block 2002 includes an angled cut out 2003, so as to provide a 45-degree angled surface.

The block 2002 optionally also includes two holes 2004 on its inner face 2002*a*. As described below, these are required if the side extension device 2000 is to be used in combination with a central extension device. The holes 2004 are inclined 6 degrees distally.

The side extension device 2000 is available in a right-handed and a left-handed configuration.

Both the right-handed and left-handed side extension devices 2000 can be hammered into the femur at the bone implant interface at the shoulder of the implant, such that the side plates 2001 rest on the anterior and posterior aspects of the top of the shoulder of the implant respectively.

The targeting device can then be placed on top of the right-handed and left-handed side extension devices 2000, so that it is still positioned on the femur, but in an elevated manner due to the extra height provided by the two blocks 2002.

The cut out 2003 is positioned lateral to the implant, such that angled channel of the targeting device is lying in line with it.

The targeting device is then clamped tight onto the side extension devices 2000.

As noted above, the side plates 2001 rest on the anterior and posterior aspects of the top of the shoulder of the implant respectively. Thus, it will be appreciated that when a pair of right-handed and left-handed side extension devices 2000 are used, these create a width between their respective side plates 2001 that is determined by the dimensions of the implant below. The targeting device must be able to be positioned onto the side extension devices 2000 and therefore the width between their respective side plates 2001 cannot exceed the maximum opening dimension between the contact elements (legs 3 and 6) on the targeting device (20 mm).

Figure 8I:
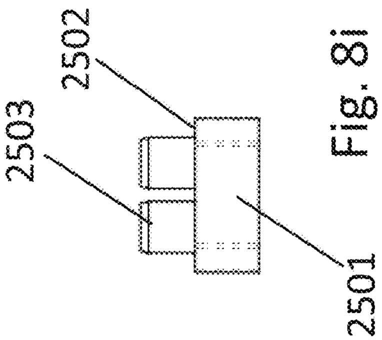
FIG. 8*i* is a top view of the central extender device shown in FIG. 8*h*
Figure 8H:
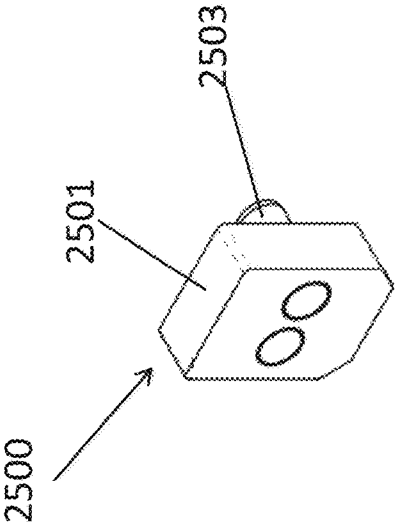
FIG. 8*h* is a perspective view of the central extender device as used in FIG. 8*g*
Figure 8G:
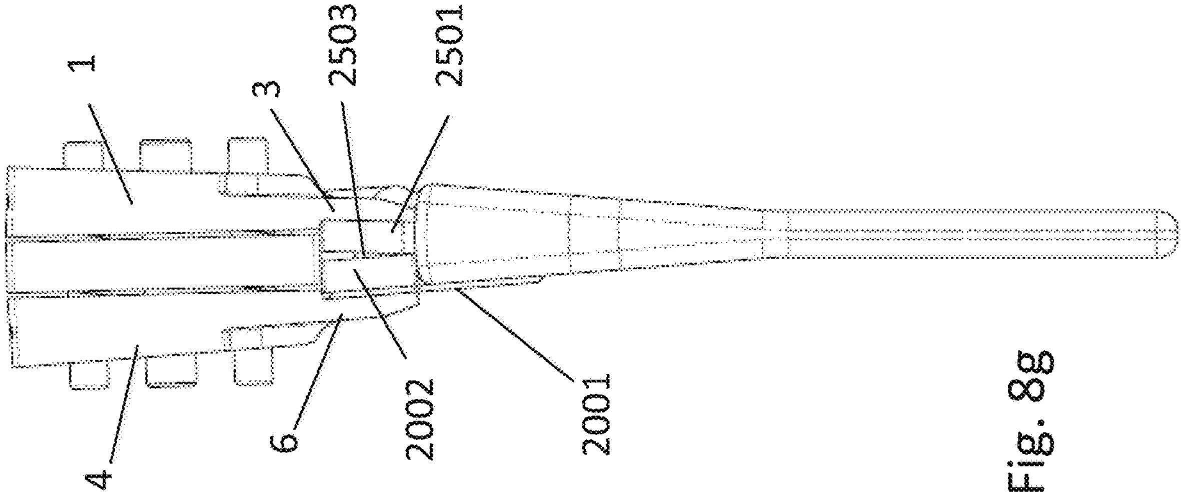
FIG. 8*g* is a side view of targeting device that can be used in the invention, located on a femoral implant, and mounted using one side extender device and one central extender device

Therefore, for larger implants, a different solution is used. In this regard, a central extension device 2500 is used in combination with one of the side extension devices 2000. The central extension device 2500 is shown in FIGS. 8*g*, 8*h* and 8*i*.

The central extension device 2500 comprises a block 2501 having a side face 2502 from which two lugs 2503 project. The two lugs 2503 are shaped and sized so that they can be received in the respective two holes 2004 on the side extension device 2000.

The central extension device 2500 can therefore be attached to a side extension device 2000 by insertion of the two lugs 2503 into the two holes 2004 in the side extension device.

The side extension device 2000 should be chosen as being left-handed or right-handed based on which side of the implant is most easily accessible.

The side extension device 2000 plus attached central extension device 2500 can be positioned by inserting the side plate 2001 on the most accessible side, by hammering into the femur at the bone implant interface at the shoulder of the implant, as before.

Due to the holes 2004 in the side extension device 2000 being inclined 6 degrees distally, when the side extension device 2000 and central extension device 2500 are attached together, the anterior surface of the side extension device 2000 and the posterior surface of the central extension device 2500 will converge by 6 degrees. In other words, the holes 2004 will be pointing downwards by 6 degrees and thus when the two lugs 2503 of the central extension device 2500 are engaged into the holes 2004 a 6 degree convergence can be achieved.

The targeting device can then be placed on top of the side extension device 2000 and the central extension device 2500, so that it is still positioned on the femur, but in an elevated manner due to the extra height provided by the block 2002 and the block 2501.

The targeting device is then clamped tight onto the side extension device 2000 and the central extension device 2500.

The medial targeting device 700 (FIGS. 6, 7 and 8) can be used and the external targeting device (FIG. 10) can be used to make certain the targeting is correct in the coronal and sagittal planes.

An external targeting device of the invention is shown in FIG. 10. This can be used with the targeting device. The external targeting device comprises a targeting device interlocking portion 701, an alignment portion 702, and a holding arrangement 703 for holding and pivoting the alignment portion 702 relative to the targeting device interlocking portion 701.

The targeting device interlocking portion 701 comprises a planar support body 704 provided with an anterior guide member interlocking component 705 and a posterior guide member interlocking component 706.

The anterior guide member interlocking component 705 comprises a first locking pin that extends from the planar support body in the same plane and can be received in the first angled channel. The posterior guide member interlocking component 706 comprises a second locking pin that extends from the planar support body in the same plane and can be received in the second angled channel. The location of the posterior guide member interlocking component 706 is fixed. A channel 707 is provided in the planar support body and the anterior guide member interlocking component 705 is provided with an engaging pin 708 that engages with and can slideably move along the channel and can be secured at any location therein. Thus the distance between the anterior guide member interlocking component 705 and the posterior guide member interlocking component 706 can be varied.

The alignment portion 702 comprises a planar elongate body 702*a* having an angled tip 702*b* at the distal end. The holding arrangement comprises a pivot nut, a pivot washer, and a locking screw that can be rotated from an open position where pivoting can occur to a locked position where pivoting is prevented. The holding arrangement therefore holds the planar elongate body and the planar support body in the same plane, but permits the pivotal movement of the planar elongate body relative to the planar support body within that plane.

In use, the first locking pin can be received in the first angled channel of the targeting device, and the second locking pin can be received in second angled channel of the targeting device, such that the planar support body is aligned with the anterior-posterior plane in which the first and second angled channels lie, and such that the planar elongate body is consequently also aligned with the anterior-posterior plane in which the first and second angled channels lie, such that the planar elongate body can be pivoted relative to the planar support body until the angled tip is alongside the implant and the plane of the angled tip can be compared to the centreline in the anterior-posterior plane, as determined via x-ray.

If the plane of the angled tip is not aligned with the centreline in the anterior-posterior plane, the location of the targeting device can be adjusted until the angled tip does align with the centreline in the anterior-posterior plane.

Figure 10B:
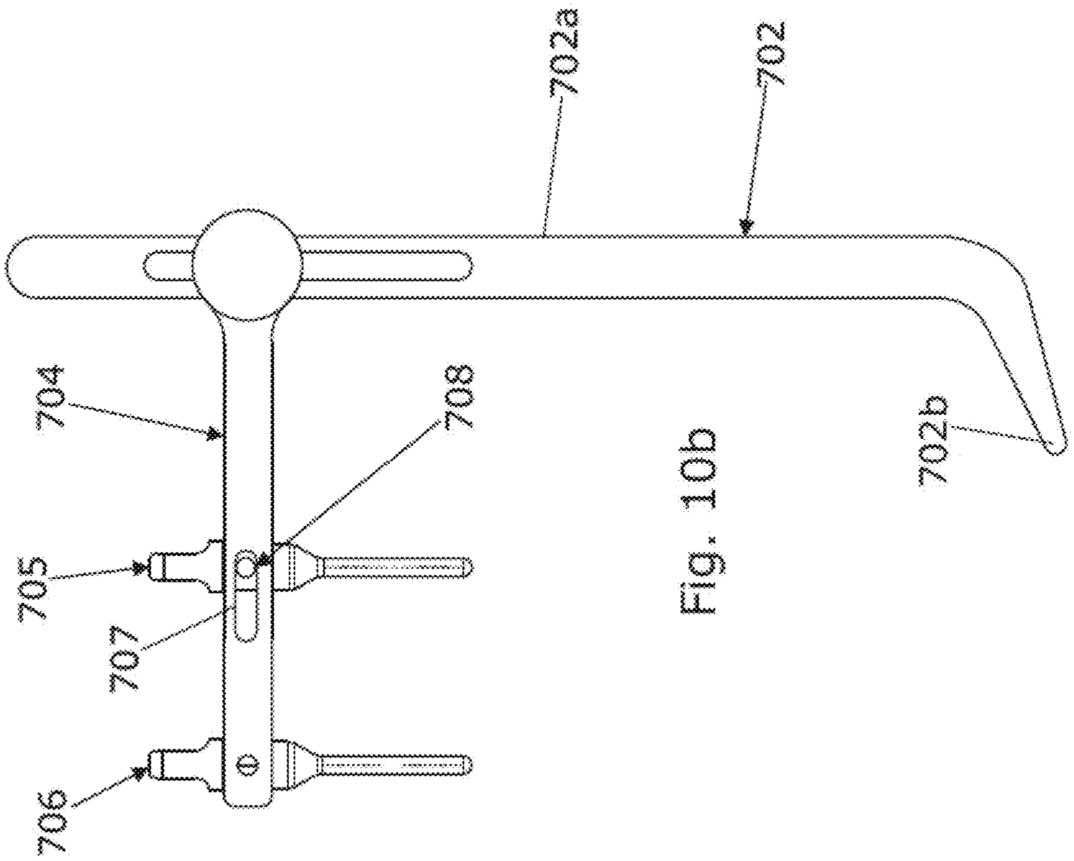
FIG. 10*b* is a side view of an external targeting device that can be used in the invention
Figure 10A:
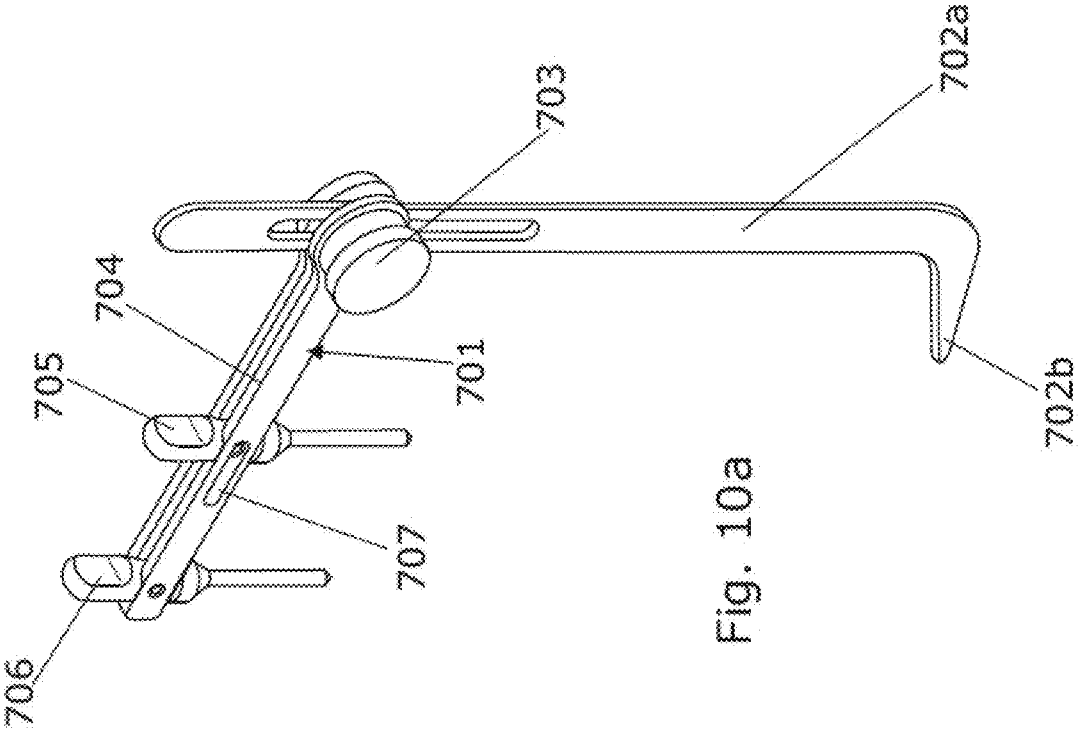
FIG. 10*a* is a perspective view of an external targeting device that can be used in the invention
Figures 10C, 10D, 10E:
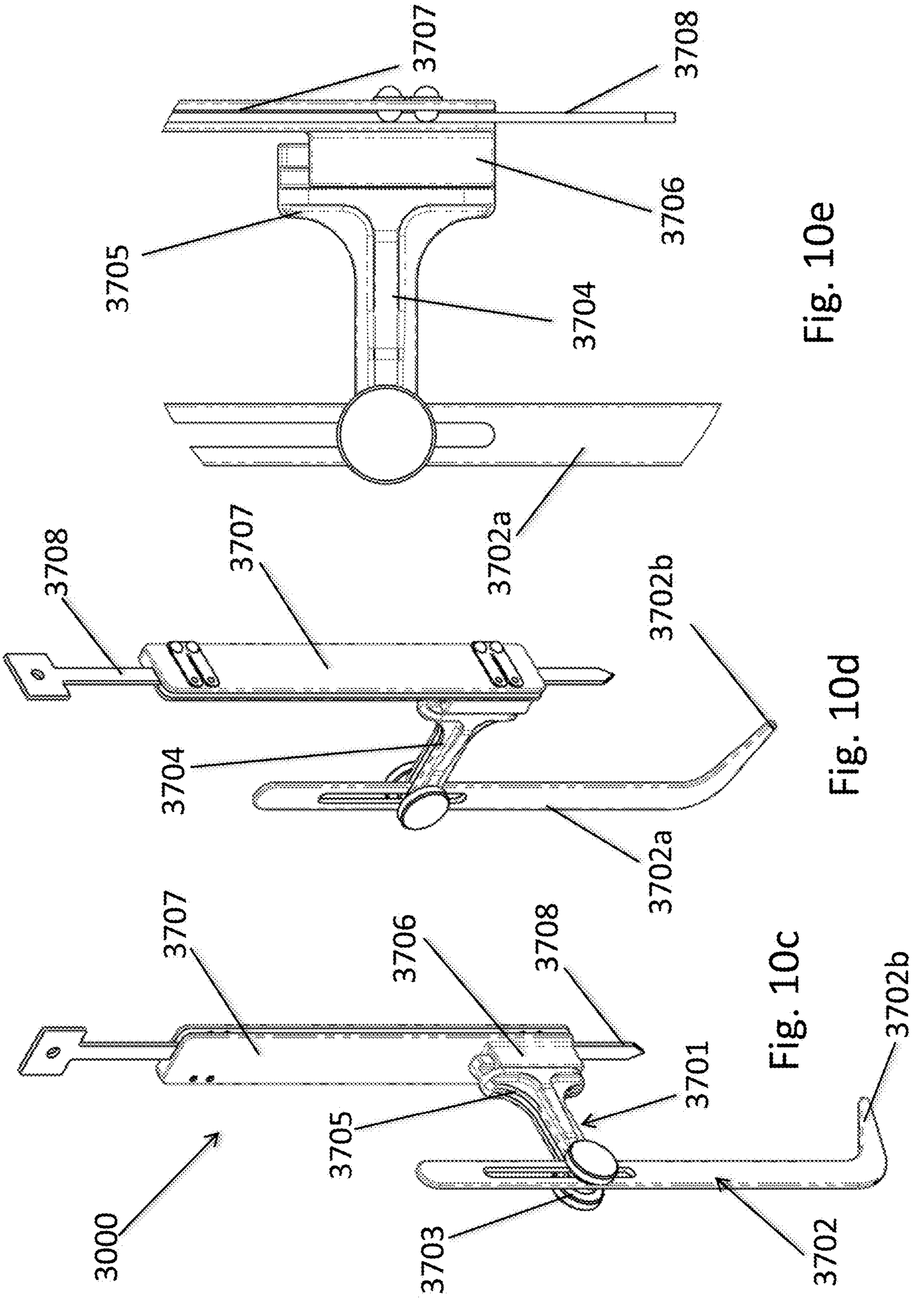
FIG. 10*c* is a perspective view of a brace targeting device, which is a modified version of the external targeting device that can be used in the invention
FIG. 10*d* is a different perspective view of the brace targeting device shown in FIG. 10*c*
FIG. 10*e* is a close-up of the box connection section of the brace targeting device shown in FIGS. 10*c* and 10*d*

FIGS. 10*c* to 10*e* show the brace targeting device 3000, which is a modified version of the external targeting device of FIGS. 10*a* and 10*b*.

The brace targeting device 3000 provides an alternative way to create access tunnels anteriorly and posteriorly, using a chevron chisel 3708 (such as the chevron chisel shown in FIGS. 5*a*-5*c*) whilst ensuring that the tunnels are correctly aligned. Thus, the brace targeting device 3000 could be used instead of a targeting device as shown in FIG. 6, FIG. 7, FIG. 8 or FIG. 9.

The brace targeting device 3000 comprises a targeting device interlocking portion 3701, an alignment portion 3702, and a holding arrangement 3703 for holding and pivoting the alignment portion 3702 relative to the targeting device interlocking portion 3701. A brace sleeve 3707 is releasably connected to the targeting device interlocking portion 3701.

The targeting device interlocking portion 3701 comprises a planar support body 3704 provided at its distal end with an interlocking component 3705.

The interlocking component 3705 engages and locks with engagement component 3706. The engagement component 3706 is fixedly attached to brace sleeve 3707. The interlocking component 3705 and the engagement component 3706 provide the releasable connection between the brace sleeve 3707 and the targeting device interlocking portion 3701.

The alignment portion 3702 comprises a planar elongate body 3702*a* having an angled tip 3702*b* at the distal end.

The holding arrangement 3703 comprises a pivot nut, a pivot washer, and a locking screw that can be rotated from an open position where pivoting can occur to a locked position where pivoting is prevented. The holding arrangement 3703 therefore holds the planar elongate body and the planar support body in the same plane, but permits the pivotal movement of the planar elongate body relative to the planar support body within that plane.

The brace sleeve 3707 is suitably a spring-loaded brace sleeve as described in relation to FIGS. 17*a*-17*c*. Thus ball bearings (e.g. four ball bearings) are provided under a flat spring (e.g. a flat steel spring). This provides a spring-loaded effect, such that when an elongate body is placed inside the elongate cavity of the brace sleeve 3707, it is clamped in place.

The elongate cavity of the brace sleeve 3707 is slightly wider than width of the chevron chisel that it is intended to be used with. The elongate cavity of the brace sleeve 3707 may suitably have a depth of 1.2 mm to 1.5 mm to allow easy passage of the chevron chisel whilst stopping distortion of the chevron chisel.

The engagement component 3706 is fixedly attached to the brace sleeve 3707, e.g. by welding. The engagement component is suitably an open-ended box (e.g. 20 mm to 30 mm in length) that can slidably receive the interlocking component 3705. The engagement component 3706 has an elongate axis that is aligned with the elongate axis of the cavity of the brace sleeve 3707.

The interlocking component 3705 is suitably a rectangular cross section solid bar that is slightly smaller in cross-section than the open-ended box engagement component 3706. Thus the solid bar interlocking component 3705 can be slid into the open-ended box engagement component 3706 and pushed until there is secure engagement.

In use, a chisel or osteotome is used (ideally 1 mm thickness) to clear a 1 mm to 2 mm deep space at the bone-implant interface from the shoulder of the implant, along the central sagittal axis of the implant.

Figure 5A:
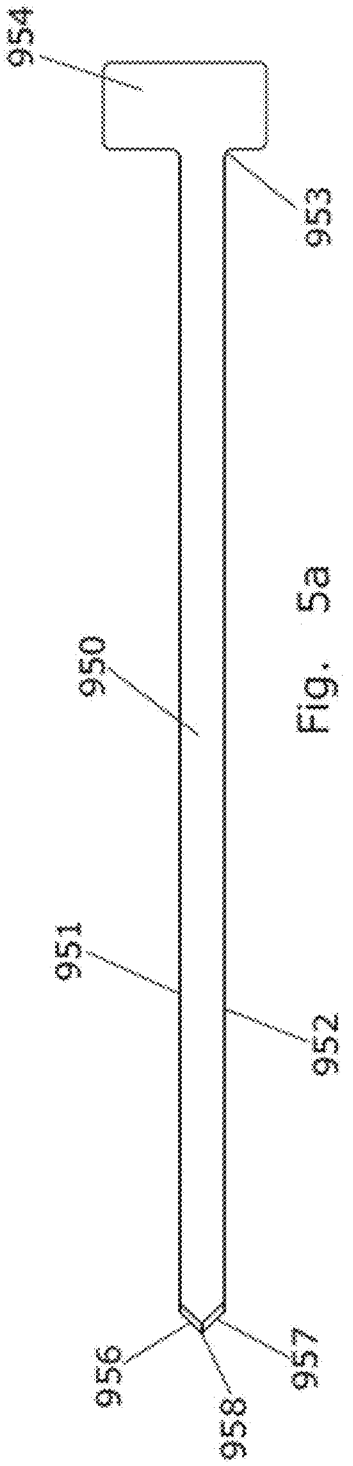
FIG. 5*a* is a plan view of a chevron chisel that can be used in the invention
Figure 5B:
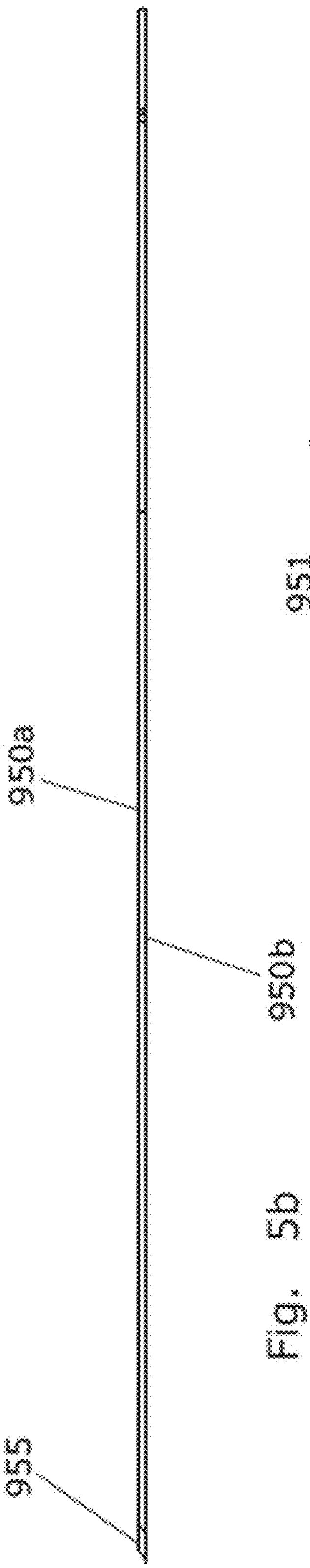
FIG. 5*b* is a side view of a chevron chisel that can be used in the invention
Figure 5C:
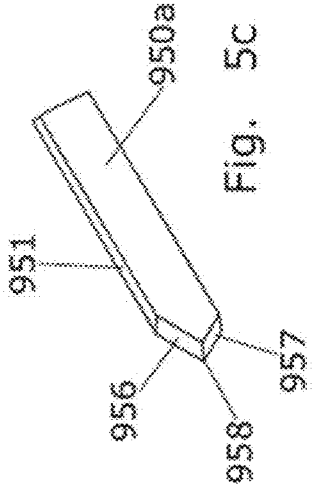
FIG. 5*c* is a perspective view of the distal end of a chevron chisel that can be used in the invention.

The brace sleeve 3707 is provided in a form where it has been released from the targeting device interlocking portion 3701. A chevron chisel 3708, such as the chevron chisel shown in FIGS. 5*a*-5*c*, is inserted into brace sleeve 3707 and secured therein by the spring-loading mechanism. The chevron chisel is positioned such that 2 mm of the chevron chisel protrudes beyond the distal end of the brace sleeve 3707, with the sharp end of the chevron chisel adjacent to the implant.

The chevron chisel is then engaged into the space that has already been created between the implant and femur. The chevron chisel is aligned in the sagittal axis of the femur.

The brace sleeve 3707 is then secured to the targeting device interlocking portion 3701 of the brace targeting device 3000 by sliding the solid bar interlocking component 3705 into the open-ended box engagement component 3706 and pushing until there is secure engagement.

The planar elongate body 3702*a* having an angled tip 3702*b* is used to align the trajectory of the chevron chisel in the brace sleeve. In this regard, the chevron chisel is hammered distally into the bone implant interface, keeping the trajectory true by making sure the angled tip 3702*b* always remains in the middle of the medio-lateral diameter of the femur.

The chevron chisel is advanced to just beyond the distal tip of the implant, thus creating an access tunnel. The chevron chisel is left in situ and the brace targeting device 3000, including the brace sleeve 3707, is removed.

A second chevron chisel can then be inserted into brace sleeve 3707 and secured therein by the spring-loading mechanism, as before.

Using the chevron chisel already in situ as a line of sight, the second chevron chisel is hammered in on the other side of the implant to create a second access tunnel.

Both the chevron chisels are then removed, and the surgical procedure is carried out further as described previously, with use of the hook curette, medial-lateral clearance device (optional) and wire delivery device.

It will be appreciated from the above discussion in the context of using the brace targeting device 3000 to provide and position a chevron chisel (which has an elongate body) that any other device with a similar size elongate body could also be provided and positioned using the brace targeting device.

In particular, it is envisaged that the brace targeting device 3000 can be used with a wire delivery device of the invention, e.g., a device 1400 according to the first embodiment as shown in FIG. 15. In this regard, either the first elongate body 1401 or the second elongate body 1421 can be placed inside the elongate cavity of the brace sleeve 3707 and clamped in place.

The planar elongate body 3702*a* of the targeting device, having angled tip 3702*b*, can be used to align the trajectory of the elongate body 1401, 1421, in the brace sleeve. In this regard, the elongate body can be hammered distally, keeping the trajectory true by making sure the angled tip 3702*b* always remains in the middle of the medio-lateral diameter of the femur.

It will be appreciated that only one of the two elongate bodies of the wire delivery device needs to be secured inside the elongate cavity of the brace sleeve 3707; the second elongate body is attached to the first elongate body via the medial and lateral cutting wire arcs and can be positioned using the first elongate body as a line of sight.

The medial-lateral clearance device that can be used in the invention is shown in FIG. 11.

The medial-lateral clearance device comprises an elongate body 300 having a proximal end 301 that can be provided with a handle 301*a* and having a distal end 302 that is blunt or may be sharp. If it is sharp, it may for example be a chevron shape. The elongate body is in the shape of a flat plate that extends from a first elongate edge 303 to a second elongate edge 304. The handle 301*a* can be understood to have an enlarged head portion extending from a neck.

In the embodiment of FIG. 11 the distal end 302 is shown as sharp. The end may be chisel like, e.g. with a 45 degree or 60 degree angled sharp end.

The medial-lateral clearance device of the invention also comprises a cutting portion 305 extending outwardly from the elongate body and located at or near the distal end 302. The cutting portion has an inner surface 306 that is flat and which connects with the first elongate edge of the elongate body at a substantially 90 degree angle. In FIG. 11 the angle is 100 degrees. The cutting portion may be formed integrally or may be attached to the elongate body, e.g. by welding.

The cutting portion has an outer surface 307 that comprises an angled cutting face 308 that is located towards the distal end of the elongate body. The inner surface meets the angled cutting face at a cutting edge 309, at an angle of from 20 to 70 degrees. This provides a sharp and chisel shaped end.

Thus the distal end of the flat plate elongate body can be located in a space at the bone-implant interface, at or near to the shoulder portion of the implant, with the flat plate being parallel to either the anterior surface or the posterior surface, and with the flat inner surface of the cutting portion aligned with either the medial or lateral surface of the implant, such that the medial-lateral clearance device can then be pushed in the direction of the distal end of the implant, with the flat plate elongate body remaining alongside the respective anterior or posterior surface, in the space at the bone-implant interface, whilst the angled cutting face cuts away bony ingrowth located at said medial or lateral surface of the implant as the device is pushed towards the distal end of the implant.

It will be appreciated that a pair of such medial-lateral clearance devices should be provided: one where the flat plate cutting portion is 90 to 110 degrees clockwise from the flat plate elongate body and one where the flat plate cutting portion is 90 to 100 degrees anticlockwise from the flat plate elongate body.

In addition, for both the "left handed" version and the "right handed" version, two or more different sizes may be provided.

Figures 11A, 11B, 11C, 11D, 12:
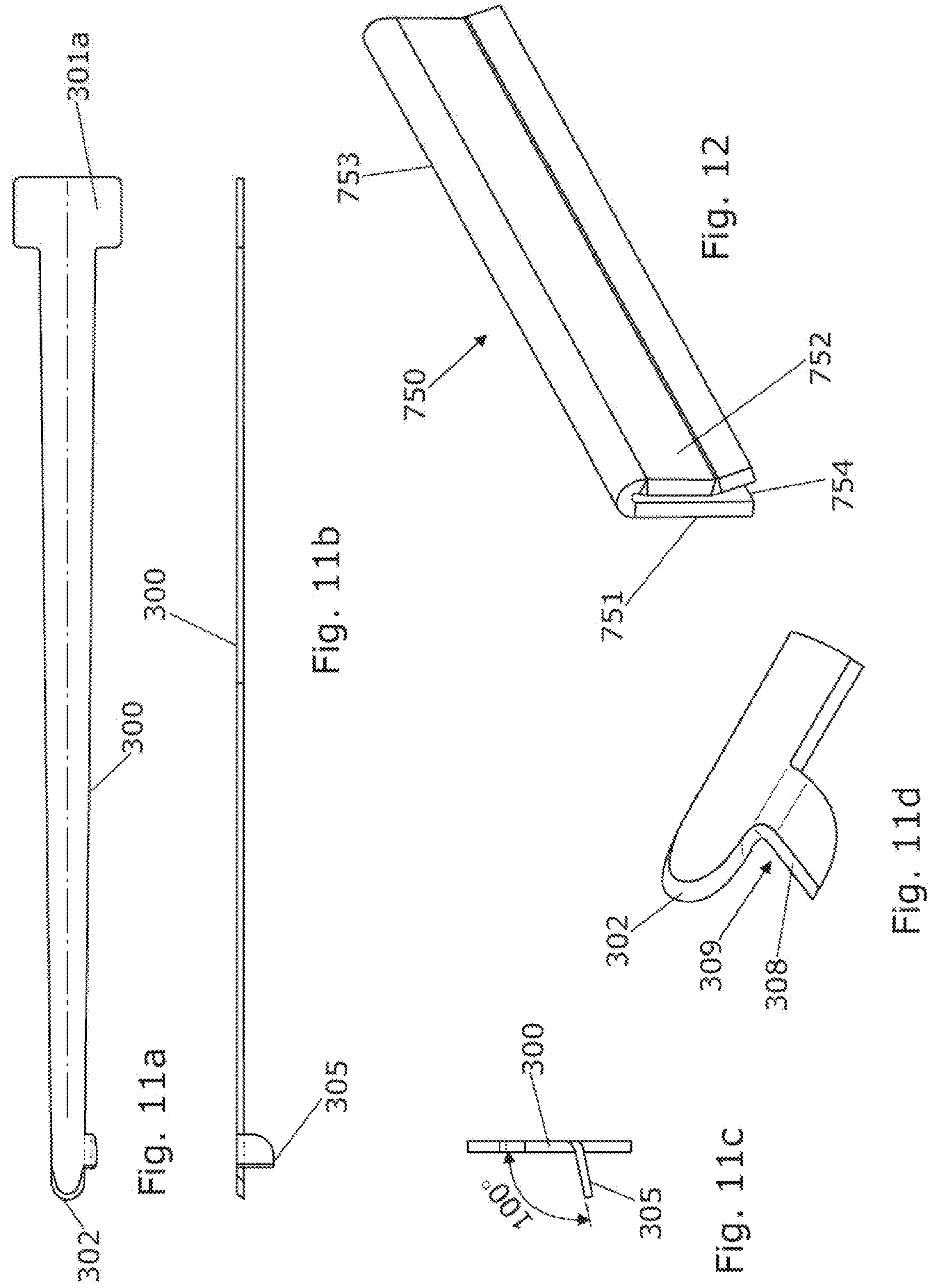
FIG. 11*a* is a plan view of a medial-lateral clearance device that can be used in the invention
FIG. 11*b* is a side view of the medial-lateral clearance device that can be used in the invention
FIG. 11*c* is a cross sectional view of the distal end of the medial-lateral clearance device as shown in FIG. 11*b*
FIG. 11*d* is a perspective view of the distal end medial-lateral clearance device
FIG. 12 is a perspective view of a brace sleeve that can be used in the invention

A brace sleeve 750 that can be used in the invention is shown in FIG. 12. The brace sleeve 750 can be used to provide structural support for the elongate body of any of the devices described above and shown in the preceding drawings, except for the targeting device which it will be appreciated does not have an elongate body. The brace sleeve can also be used to provide support for the handle of any of the devices described above and shown in the preceding drawings, except for the targeting device which it will be appreciated does not have a handle.

The brace sleeve 750 comprises two elongate faces 751, 752 which are joined at one elongate edge 753 and are open at the opposite elongate edge and at both the two ends, so as to create an elongate cavity between the two faces within which an elongate body can be slidably received. The brace sleeve can slide onto and over an elongate body to provide additional strength and resistance to bending during use. The brace sleeve can cover some, most or all of the length of an elongate body of any of the devices described above.

The two elongate faces may be flat and parallel to one another. However, in the illustrated embodiment, one of the elongate faces 752 flares outwardly towards the open elongate edge. This can assist with ease of placing the brace sleeve onto the elongate body, because it means that the open "mouth" of the brace sleeve is larger than the closed edge.

Figure 16A:
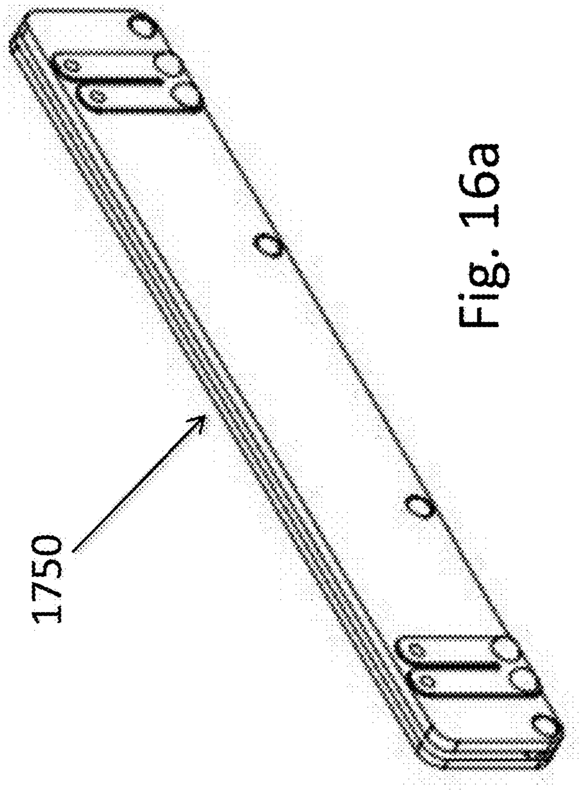
FIG. 16*a* is a perspective view of spring-loaded brace sleeve that can be used in the invention
Figure 16B:
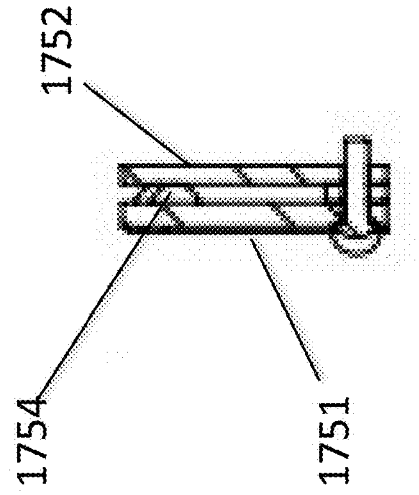
FIG. 16*b* is a first end view of the spring-loaded brace sleeve shown in FIG. 16*a*
Figure 16C:
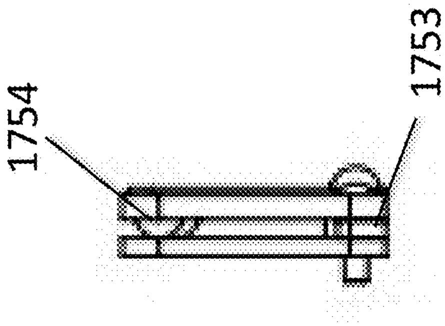
FIG. 16*c* is a second end view of the spring-loaded brace sleeve shown in FIG. 16*a*.

FIGS. 16*a-c* show an alternative embodiment of a brace sleeve 1750 that can be used in the invention. The brace sleeve 1750 can be used to provide structural support for the elongate body of any of the devices described above and shown in the preceding drawings, except for the targeting device which it will be appreciated does not have an elongate body. The brace sleeve can also be used to provide support for the handle of any of the devices described above and shown in the preceding drawings, except for the targeting device which it will be appreciated does not have a handle.

The brace sleeve 1750 comprises two elongate faces 1751, 1752 which are joined at one elongate edge 1753 and are open at the opposite elongate edge and at both the two ends, so as to create an elongate cavity between the two faces within which an elongate body can be slidably received. The brace sleeve can slide onto and over an elongate body to provide additional strength and resistance to bending during use. The brace sleeve can cover some, most or all of the length of an elongate body of any of the devices described above.

The two elongate faces may be flat and parallel to one another, as illustrated.

The brace sleeve 1750 is provided with a securing system in which ball bearings 1754 (e.g. four ball bearings) are provided under a flat spring (e.g. a flat steel spring). This provides a spring-loaded effect, such that when an elongate body is placed inside the elongate cavity, it is clamped in place.

The brace sleeve 1750 may be provided in different lengths, e.g. there may be an 80 mm length and a 140 mm length version.

The width of the cavity may, for example, be from 1.3 mm to 1.9 mm, e.g. 1.5 mm; this can be chosen to suit the thickness of the elongate body to be received.

The ball bearings may have a diameter of 3 mm to 5 mm, e.g., about 4 mm. The flat spring may, for example, be about 0.5 mm thick.

The ball bearing and spring arrangement holds the elongate body, e.g. the elongate body of a chevron chisel inside the brace sleeve, and stops the brace sleeve coming away from the device when the brace is not held by the surgeon.

Figure 17:
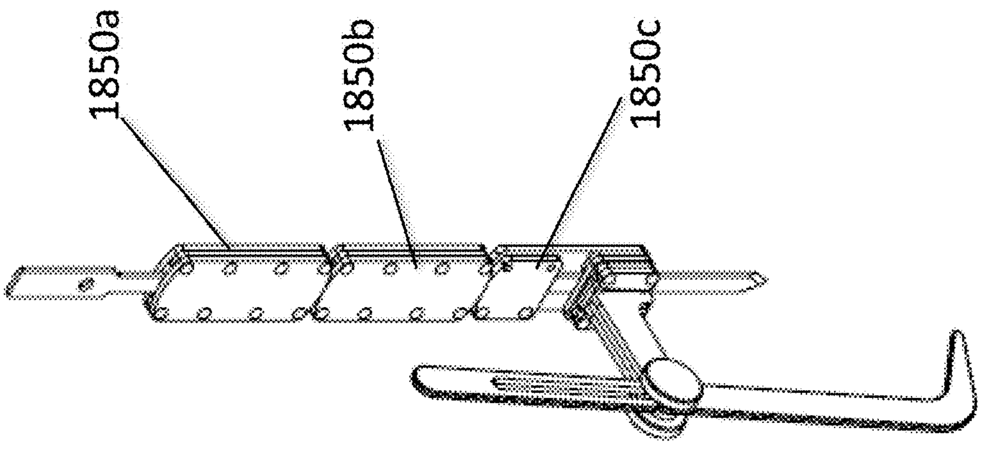
FIG. 17 is a perspective view of a brace targeting device, which is a modified version of the brace targeting device shown in FIGS. 10*c*-10*e* and has three brace sections

A brace sleeve 1850 may alternatively be provided in multiple sections, e.g. two or three or four sections, as shown in FIG. 17. Again, this brace sleeve 1850 can be used to provide structural support for the elongate body of any of the devices described above and shown in the preceding drawings, except for the targeting device which it will be appreciated does not have an elongate body. It could also be used to support a handle.

In this illustrated embodiment there are three brace sections 1850*a*, 1850*b* and 1850*c*, each of which may be, e.g. about 50 mm long. They each have an internal space sized for receiving an elongate body, such as the elongate body of a chevron chisel, inside the brace sleeve. For example, the internal space may measure about 1.4 mm×8.5 mm.

One or more of the brace sections 1850*a* may be provided with a spring locking mechanism, e.g. as shown and described in FIG. 17.

In one embodiment, one of the brace sections 1850*c* may be provided adjacent to a brace targeting device, e.g. as shown and described in FIGS. 10*c-e*.

All of the brace sections 1850*a*, 1850*b* and 1850*c* can be slid off the elongate body of any of the devices described above and shown in the preceding drawings, in a proximal direction. This can, for example, be carried out as the device is advanced into the bone-implant interface. Any universal handle would of course need to be removed before sliding the brace section off the elongate body.

A moulded brace support is also provided by the present invention. This brace support can be injection molded, which facilitates the use of medical grade plastics. The moulded brace support can be made from any suitable medical grade plastic. It will be appreciated that the plastic should be soft enough that it can form a foldable hinge.

The moulded brace support is designed to provide structural support for (a) the elongate body of any of the devices described above and shown in the preceding drawings, except for the targeting device which it will be appreciated does not have an elongate body; and (b) a brace targeting device, e.g. as shown and described in FIGS. 10*c-e*.

The moulded brace support is shown in FIGS. 18*a-d*. The moulded brace support 1950 comprises three adjoined portions 1951, 1952, 1953 which in the unfolded configuration lie in the same plane but can fold together via hinges 1954 and 1955 to form the folded configuration of the moulded brace support 1950.

Figure 18B:
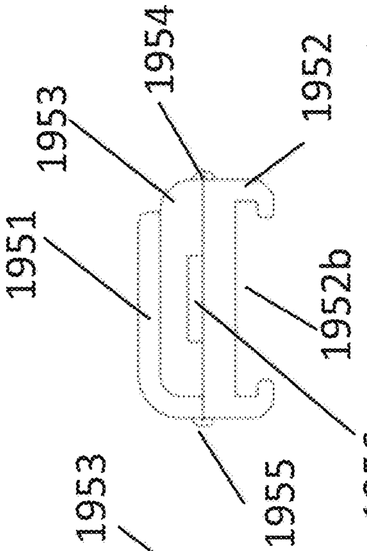
FIG. 18*b* is a cross sectional view of the moulded brace device of FIG. 18*a* in a closed (folded) configuration
Figure 18A:
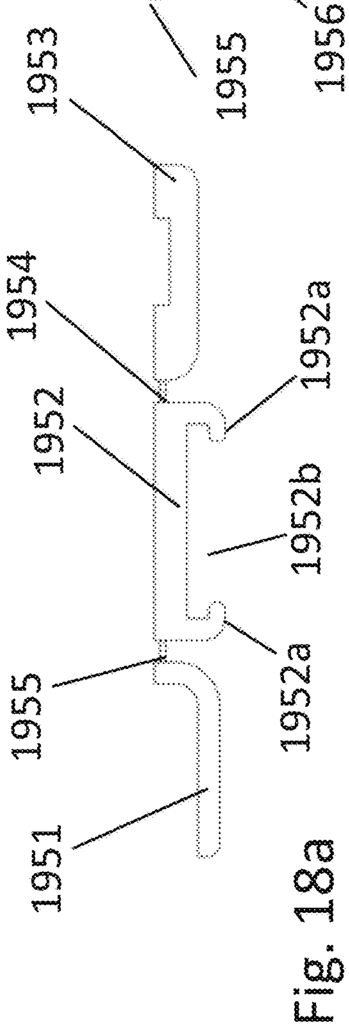
FIG. 18*a* is a cross sectional view of a moulded brace device in an open configuration
Figure 18D:
FIG. 18*d* is a plan view of the moulded brace device of FIG. 18*a* in the closed (folded) configuration
Figure 18C:
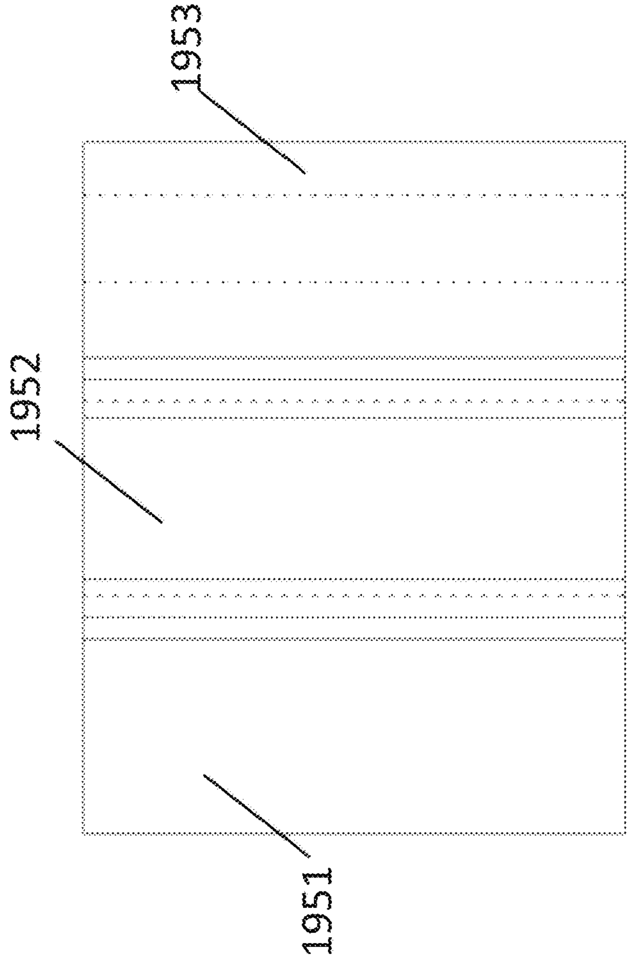
FIG. 18*c* is a plan view of the moulded brace device of FIG. 18*a* in the open configuration

The base portion 1952 is located centrally in the unfolded configuration as shown in FIGS. 18*a* and 18*c*. The cavity-defining portion 1953 is attached to one side of the base portion 1952 via a hinge 1954, and the locking portion 1951 is attached to the opposite side of the base portion 1952 via a hinge 1955.

The base portion 1952 is provided with a pair of arms 1952*a* which together define a receiving portion 1952*b* in which a portion of the brace targeting device can be received. The cavity-defining portion 1953 is provided with a cut-out cavity 1956 within which an elongate body can be slidably received.

When the moulded brace support 1950 is in its folded configuration, as shown in FIGS. 18*b* and 18*d*, it is ready for use as a supporting brace.

In the folded configuration, the cavity-defining portion 1953 is folded on top of the base portion 1952 using hinge 1954, and the locking portion 1951 is folded on top of cavity-defining portion 1953 using hinge 1955. The cavity 1956 is then located and defined between the cavity-defining portion 1953 and the base portion 1952. This cavity 1956 is an elongate cavity within which an elongate body, such as the elongate body of a chevron chisel, can be slidably received. The pair of arms 1952*a* define the receiving portion 1952*b* in which an upright portion of the brace targeting device can be slidably received.

The moulded brace support 1950 can therefore be folded and locked in place over an elongate body, as the elongate body of a chevron chisel, to provide additional strength and resistance to bending during use. The moulded brace support can cover some, most or all of the length of an elongate body of any of the devices described above. The moulded brace support also receives and supports the brace targeting device.

It will be appreciated that the brace targeting device may also have some of its component parts injection moulded; for example, the alignment portion 3702 (comprising planar elongate body 3702*a* having an angled tip 3702*b* at the distal end) can be injection moulded, e.g. from medical grade plastics. However, it is also envisaged that the brace targeting device is made entirely from metal, e.g. stainless steel.

The invention claimed is:

1. A wire delivery device suitable for use in removing bony ingrowth from an implant or a femoral implant, the device comprising:

a first elongate body that extends from a first elongate edge to a second elongate edge and that has an inner face and an outer face, the first elongate body having a proximal end that can be provided with a handle and a distal end, wherein the first elongate body comprises a first wire receiving slot and a second wire receiving slot, wherein each of the first and second wire receiving slots are provided in a spaced relationship with the distal end and run from an open entrance to a closed end, and the first wire receiving slot located towards the first elongate edge and the second wire receiving slot located towards the second elongate edge;

a second elongate body that extends from a first elongate edge to a second elongate edge and that has an inner face and an outer face, the second elongate body having a proximal end that can be provided with a handle and a distal end, wherein the second elongate body comprises a first wire receiving slot and a second wire receiving slot, wherein each of the first and second wire receiving slots are provided in a spaced relationship with the distal end and run from an open entrance to a closed end, the first wire receiving slot located towards the first elongate edge and the second wire receiving slot located towards the second elongate edge;

a first length of cutting wire extending from a first end to a second end, wherein the first end is secured in the first wire receiving slot of the first elongate body and the second end is secured in the first wire receiving slot of the second elongate body;

a second length of cutting wire extending from a first end to a second end, wherein the first end of the second length is secured in the second wire receiving slot of the first elongate body and the second end of the second length is secured in the second wire receiving slot of the second elongate body;

wherein, in use, the elongate bodies can be positioned in a spaced apart and opposite but aligned configuration, wherein the first length of cutting wire provides a medial cutting wire arc extending from the open entrance of the first wire receiving slot of the first elongate body to the open entrance of the first wire receiving slot of the second elongate body, and wherein the second length of cutting wire provides a lateral cutting wire arc extending from the open entrance of the second wire receiving slot of the first elongate body to the open entrance of the second wire receiving slot of the second elongate body, whereby the medial and lateral cutting wire arcs can then be used to cut by pushing the first and second elongate bodies in an alternating motion in a desired direction of cutting.

2. The device of claim 1, wherein the first elongate body and the second elongate body have the same size and shape.

3. The device of claim 1, wherein the first elongate body is in the form of a flat plate and the second elongate body is in the form of a flat plate.

4. The device of claim 1, wherein each of the first and second elongate bodies is provided with an integral handle at its proximal end or is provided with a handle at its proximal end in use.

5. The device of claim 1, wherein each of the first and second elongate bodies includes a tapered portion at or near to the location where the wire receiving slots are provided.

6. The device of claim 1, wherein for each of the first and second elongate bodies the first wire receiving slot is defined between a first elongate outer wall and the first elongate edge, and the second wire receiving slot is defined between a second elongate outer wall and the second elongate edge.

7. The device of claim 1, wherein each of the first wire receiving slots extends substantially parallel to an elongate axis of the respective elongate body and each of the second wire receiving slots extends substantially parallel to the elongate axis of the respective elongate body.

8. The device of claim 1, wherein the medial cutting wire and the lateral cutting wire is annealed cable rope wire formed from stainless steel or titanium or titanium alloy, or is Gigli wire.

9. The device of claim 8, wherein the medial cutting wire and lateral cutting wire are each Gigli wire with a diameter in the range from 0.8 mm to 1 mm.

10. The device of claim 1, wherein each end of the medial cutting wire and the lateral cutting wire is crimped in a ferrule, wherein the ferrule is welded, or laser welded, into a respective first or second receiving slot.

11. A kit suitable for use in removing an implant or a femoral implant, the kit comprising the device of claim 1 together with one or more of:

a) a chevron chisel;

b) a curette;

c) a medial-lateral clearance device;

d) a targeting device.

12. The device of claim 1, wherein the medial cutting wire arc has a length from 50 to 100 mm and the lateral cutting wire arc has a length from 50 to 100 mm.

13. The device of claim 1, wherein the distal end of the first elongate body and the distal end of the second elongate body each have a chevron shape.

14. A wire delivery device suitable for use in removing bony ingrowth from an implant or a femoral implant, wherein the device comprises:

a first elongate body that extends from a first elongate edge to a second elongate edge and that has an inner face and an outer face, the first elongate body having a proximal end that can be provided with a handle and a distal end, where there is a first wire guidance channel provided in a spaced relationship with the distal end and located within the first elongate body, wherein the first wire guidance channel runs from an entrance at the first elongate edge to an exit at the second elongate edge, and wherein either the inner face or the outer face includes a first mouth portion to access the first wire guidance channel and a first engagement protrusion adjacent to the first mouth portion for engaging with a first part of a wire loop and securing this part of the wire loop within the first wire guidance channel;

a second elongate body that extends from a first elongate edge to a second elongate edge and that has an inner face and an outer face, the second elongate body having a proximal end that can be provided with a handle and a distal end, where there is a second wire guidance channel provided in a spaced relationship with the distal end and located within the second elongate body, wherein the second wire guidance channel runs from an entrance at the first elongate edge to an exit at the second elongate edge, and wherein either the inner face or the outer face includes a second mouth portion to access the second wire guidance channel and a second engagement protrusion adjacent to the second mouth portion for engaging with a second part of the wire loop and securing this part of the wire loop within the second wire guidance channel;

wherein, in use, a first part of the wire loop can be fed into the first wire guidance channel via the first mouth portion and secured therein by engagement with the first engagement protrusion and a second part of the wire loop can be fed into the second wire guidance channel via the second mouth portion and secured therein by engagement with the second engagement protrusion, and the elongate bodies can be positioned in a spaced apart and opposite but aligned configuration, so that the wire loop provides a medial cutting wire arc from the exit of the first wire guidance channel to the entrance of the second wire guidance channel and provides a lateral cutting wire arc from the exit of the second wire guidance channel to the entrance of the first wire guidance channel, whereby the medial cutting wire arc and the lateral cutting wire arc can then be used to cut by pushing the first and second elongate bodies in an alternating motion in a desired direction of cutting.

15. The device of claim 14, wherein the first mouth portion is closer to the distal end of the first elongate body than the first engagement protrusion, and the second mouth portion is closer to the distal end of the second elongate body than the second engagement protrusion.

16. The device of claim 14 in the form of a kit, wherein the wire loop comprises a first wire loop and the kit comprises one or more additional wire loop(s), each of the one or more additional wire loop(s) being different sizes and/or different materials from each other and from the first wire loop.

17. The device of claim 16, wherein the first wire loop and the one or more additional wire loops comprise cable rope wire formed from stainless steel, or titanium, or titanium alloy, or is Gigli wire.

18. The device of claim 17, wherein the two or more wire loops are each Gigli wires, each with a diameter in the range from 0.8 mm to 1 mm.

19. The device of claim 14, wherein the wire loop has been formed by ferrule crimping.

20. The device of claim 14, wherein the medial cutting wire arc has a length from 50 to 100 mm and the lateral cutting wire arc has a length from 50 to 100 mm.

* * * * *